(12) United States Patent
Dixon et al.

(10) Patent No.: US 10,537,733 B2
(45) Date of Patent: Jan. 21, 2020

(54) FUNCTIONAL ELECTRICAL STIMULATION CYCLING DEVICE FOR PEOPLE WITH IMPAIRED MOBILITY

(71) Applicant: University of Florida Research Foundation, Incorporated, Gainesville, FL (US)

(72) Inventors: Warren Dixon, Gainesville, FL (US); Matthew J. Bellman, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 135 days.

(21) Appl. No.: 15/308,541

(22) PCT Filed: Jun. 5, 2015

(86) PCT No.: PCT/US2015/034562
§ 371 (c)(1),
(2) Date: Nov. 2, 2016

(87) PCT Pub. No.: WO2015/199956
PCT Pub. Date: Dec. 30, 2015

(65) Prior Publication Data
US 2017/0157396 A1    Jun. 8, 2017

Related U.S. Application Data

(60) Provisional application No. 62/008,402, filed on Jun. 5, 2014.

(51) Int. Cl.
*A61N 1/36* (2006.01)
*A61N 1/04* (2006.01)

(52) U.S. Cl.
CPC ....... *A61N 1/36003* (2013.01); *A61N 1/0452* (2013.01); *A61N 1/0484* (2013.01); *A61N 1/36014* (2013.01)

(58) Field of Classification Search
CPC .................... A61N 1/36003; A61N 1/0452
See application file for complete search history.

(56) References Cited

U.S. PATENT DOCUMENTS

| 5,121,747 A | 6/1992 | Andrews |
| 5,507,788 A | 4/1996 | Lieber |

(Continued)

FOREIGN PATENT DOCUMENTS

| CN | 2654173 Y | 11/2004 |
| CN | 101244753 A | 8/2008 |

(Continued)

OTHER PUBLICATIONS

Abbas J J, Triolo R J, Experimental Evaluation of an Adaptive Feedforward Controller for Use in Functional Neuromuscular Stimulation Systems, IEEE Trans Rehabil Eng. Mar. 1997; 5(1): 12-22.*

(Continued)

*Primary Examiner* — William J Levicky
(74) *Attorney, Agent, or Firm* — Wolf, Greenfield & Sacks, P.C.

(57) ABSTRACT

Functional electrical stimulation (FES) cycling devices and associated methods are generally described. An FES cycling device may comprise a crank, two or more pedals connected to the crank, one or more sensors adapted to measure position and/or velocity of the crank, and one or more electrodes configured to deliver electrical stimulation to a person associated with the cycling device. In some cases, the FES cycling device further comprises a controller configured to receive input signals from the one or more sensors and deliver output signals to the one or more electrodes. In (Continued)

certain cases, the controller may dynamically generate a control signal to deliver an amount of electrical stimulation to a muscle group (e.g., quadriceps femoris, gluteal muscles, hamstring muscles) based on the value of a determined torque transfer ratio between a joint of the person and the crank of the cycling device. The electrical stimulation may, in some cases, cause the person to pedal the cycling device.

21 Claims, 24 Drawing Sheets

(56) References Cited

U.S. PATENT DOCUMENTS

| | | | |
|---|---|---|---|
| 5,980,435 | A | 11/1999 | Joutras et al. |
| 7,190,141 | B1* | 3/2007 | Ashrafiuon ............ B25J 9/0006 318/568.12 |
| 7,280,871 | B2 | 10/2007 | Davis et al. |
| 7,497,806 | B2 | 3/2009 | Duncan et al. |
| 8,249,714 | B1 | 8/2012 | Hartman et al. |
| 8,620,438 | B1 | 12/2013 | Wijting et al. |
| 2003/0083596 | A1 | 5/2003 | Kramer et al. |
| 2003/0093012 | A1 | 5/2003 | Smyser et al. |
| 2004/0172097 | A1 | 9/2004 | Brodard et al. |
| 2006/0247095 | A1 | 11/2006 | Rummerfield |
| 2007/0208392 | A1* | 9/2007 | Kuschner ............ A61N 1/36003 607/48 |
| 2009/0018612 | A1* | 1/2009 | Duncan .............. A61N 1/36003 607/48 |
| 2013/0331911 | A1 | 12/2013 | King et al. |
| 2016/0310731 | A1 | 10/2016 | Dixon et al. |

FOREIGN PATENT DOCUMENTS

| | | |
|---|---|---|
| EP | 1 552 492 A2 | 7/2005 |
| JP | 2003-117006 A | 4/2003 |
| WO | WO 03/105744 A2 | 12/2003 |

OTHER PUBLICATIONS

Lin FJ, Wai WJ. Sliding-mode-controlled slider-crank mechanism with fuzzy neural network. IEEE T Ind Electron 2001; 48: 60-70.*

Extended European Search Report for European Application No. EP 15811103.9 dated Dec. 12, 2017.
International Search Report and Written Opinion for International Application No. PCT/US2014/071309 dated Apr. 17, 2015.
Invitation to Pay Additional Fees for International Application No. PCT/US2015/034562 dated Nov. 11, 2015.
International Search Report and Written Opinion for International Application No. PCT/US2015/034562 dated Feb. 1, 2016.
[No Author Listed], About Us. Restorative Therapies: The Leader in FES Powered Systems. http://www.restorative-therapies.com/about-us [last accessed Aug. 11, 2016]. 4 pages.
Andrews et al., Hybrid FES orthosis incorporating closed loop control and sensory feedback. J Biomed Eng. Apr. 1988;10(2):189-95.
Bellman et al., Automatic Control of Cycling Induced by Functional Electrical Stimulation with Electric Motor Assistance. IEEE Trans Aut Sci Eng. 2017;14(2):1225-34.
Bellman et al., Stationary Cycling Induced by Switched Functional Electrical Stimulation Control. arXiv:1309.7937v3. Mar. 13, 2014. 8 pages.
Bellman et al., Switched Control of Cadence During Stationary Cycling Induced by Functional Electrical Stimulation. IEEE Trans Neur Sys Rehab Eng. Nov. 13, 2015. [Epub ahead of print]. 11 pages.
Berkelmans et al., The development of a hybrid outdoor FES bike. 8th Annual Conference of the International FES Society. Maroochydore, Queensland. Jul. 2003 2 pages.
Bhatia et al., State of art: Functional Electrical Stimulation (FES). Int J Biomed Eng Tech. Feb. 8, 2011;5(1):77-99.
Dai et al., Application of tilt sensors in functional electrical stimulation. IEEE Trans Rehab Eng. Jun. 1996;4(2):63-72.
Sharma et al., Nonlinear Neuromuscular Electrical Stimulation Tracking Control of a Human Limb. IEEE Trans Neur Sys Rehab Eng. Dec. 2009;17(6):576-84.
Takahashi et al., FES Cycling Chair for the Lower Limbs Disabled People with Electric Motor Power Assist. 9th Annual Conference of the International FES Society. Bournemouth, UK. Sep. 2004 3 pages.
Willemsen et al., Real-time gait assessment utilizing a new way of accelerometry. J Biomech. 1990;23(8):859-63.
Yeom et al., Autogenic EMG-controlled functional electrical stimulation for ankle dorsiflexion.control. J Neurosci Meth. Oct. 30, 2010;193(1):118-25. doi:10.1016/j.jneumeth.2010.08.011. Epub Oct. 30, 2011. 17 pages.

* cited by examiner

FUNCTIONAL ELECTRICAL STIMULATION CYCLING DEVICE FOR PEOPLE WITH IMPAIRED MOBILITY

RELATED APPLICATIONS

The present application is the national stage of International Application No. PCT/US2015/034562, entitled "FUNCTIONAL ELECTRICAL STIMULATION CYCLING DEVICE FOR PEOPLE WITH IMPAIRED MOBILITY," filed on Jun. 5, 2015, which claims priority under 35 U.S.C. § 119(e) to U.S. Provisional Application Ser. No. 62/008,402, entitled "FUNCTIONAL ELECTRICAL STIMULATION CYCLING DEVICE FOR PEOPLE WITH IMPAIRED MOBILITY," filed Jun. 5, 2014, the entire disclosure of both applications are hereby incorporated by reference in their entirety for all purposes.

GOVERNMENT FUNDING

This invention was made with Government support under CMMI-1161260 awarded by the National Science Foundation and FA9550-11-C-0028 awarded by the Department of Defense, Air Force Office of Scientific Research. The Government has certain rights in this invention.

FIELD

The present invention generally relates to functional electrical stimulation devices and associated methods, and, in particular, to functional electrical stimulation cycling devices.

BACKGROUND

Upper motor neuron lesions (UMNL), which may be caused by neural disorders such as stroke, cerebrovascular accident, spinal cord injury, cerebral palsy, and/or traumatic brain injury, cause disability and paralysis in millions of people. Since the lower motor neuron system and muscles are generally intact in those with UMNL, muscle contractions may be evoked by directly applying electrical stimulus to the muscles via one or more electrodes. This technique, which may be used for rehabilitation and restoration of motor function, may be referred to as neuromuscular electrical stimulation (NMES). It may also be referred to as functional electrical stimulation (FES) when it is applied to produce a functional outcome, such as standing, cycling, and/or walking.

A number of challenges have been associated with development of NMES devices and methods, including the non-linear response of muscle to electrical stimulation, load changes during functional movement, unexpected muscle spasticity, time lag between electrical stimulation and muscle force output, uncertainties in muscle physiology (e.g., temperature, pH, and/or architecture), and muscle fatigue.

One particular application of FES is FES-induced cycling. Since the 1980s, FES-induced cycling has been investigated as a safe means of exercise and rehabilitation for people with lower-limb paresis or paralysis, and numerous physiological benefits (e.g., improved cardiovascular health, increased muscle mass and bone mineral density, decreased spasticity, lower limb function) and psychological benefits (e.g., improved self-image, independence, socialization) have been reported. However, despite the reported benefits, FES-induced cycling generally has been metabolically inefficient and has resulted in low power output compared to volitional cycling by able-bodied individuals.

Improved devices and methods for application of electrical stimulation to a human body to produce functional outcomes, such as cycling, would be desirable.

SUMMARY

Embodiments described herein generally relate to providing functional electrical stimulation. In some embodiments, a method comprises delivering a first amount of electrical stimulation to at least a portion of a first set of quadriceps femoris muscles on a first leg of the person, wherein the first amount of electrical stimulation is delivered when a first torque transfer ratio between a knee of the first leg and a crank of a cycling device is negative. In certain cases, the method comprises delivering a second amount of electrical stimulation to at least a portion of a second set of quadriceps femoris muscles on a second leg of a person, wherein the second amount of electrical stimulation is delivered when a second torque transfer ratio between a knee of the second leg and the crank is negative. In some cases, the electrical stimulation causes the person to pedal the cycling device.

In some embodiments, an exercise device comprises: a crank, configured for rotation by at least one limb of a human; at least one sensor adapted to measure position and velocity of the crank; and a controller, coupled to the at least one sensor. In certain cases, the controller is programmed to generate functional electrical stimulation to a person using the exercise device, by: for each of at least one human limb, determining a torque transfer ratio between a portion of the human limb and the crank based on position and velocity of the crank measured by the at least one sensor; and, for each of the at least one human limbs, dynamically generating a control signal to control delivery of electrical stimulation to the at least one human limb based on the determined torque transfer ratio.

In some embodiments, a method of providing functional electrical stimulation to a person comprises delivering a first amount of electrical stimulation to at least a portion of a first set of gluteal muscles on a first leg of the person, wherein the first amount of electrical stimulation is delivered when a first torque transfer ratio between the hip of the person and a crank of a cycling device is positive. In certain cases, the method further comprises delivering a second amount of electrical stimulation to at least a portion of a second set of gluteal muscles on a second leg of the person, wherein the second amount of electrical stimulation is delivered when a second torque transfer ratio between the hip of the person and the crank is positive. In some cases, the electrical stimulation causes the person to pedal the cycling device.

In certain embodiments, a method of providing functional electrical stimulation to a person comprises delivering a first amount of electrical stimulation to at least a portion of a first set of hamstring muscles on a first leg of the person, wherein the first amount of electrical stimulation is delivered when a first torque transfer ratio between a knee of the first leg and a crank of a cycling device is positive. In some cases, the method further comprises delivering a second amount of electrical stimulation to at least a portion of a second set of hamstring muscles on a second leg of the person, wherein the second amount of electrical stimulation is delivered when a second torque transfer ratio between a knee of the second leg and the crank is positive. In some cases, the electrical stimulation causes the person to pedal the cycling device.

According to some embodiments, a method of providing functional electrical stimulation to a person comprises delivering a first amount of electrical stimulation to at least a portion of a first set of muscles on a first leg of the person for a first amount of time. In certain cases, the method further comprises delivering a second amount of electrical stimulation to at least a portion of a second set of muscles on a second leg of the person for a second amount of time. In certain embodiments, the method further comprises providing an amount of power to a crank of a cycling device for a third amount of time. In some cases, the first amount of time is during a first part of a trajectory of the crank, the second amount of time is during a second part of the trajectory of the crank, and the third amount of time is during a third part of the trajectory of the crank. In certain cases, at least a portion of the first, second, and third parts of the trajectory of the crank do not overlap. In some embodiments, the electrical stimulation causes the person to pedal the cycling device.

The subject matter of the present invention involves, in some cases, interrelated products, alternative solutions to a particular problem, and/or a plurality of different uses of one or more systems and/or articles.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
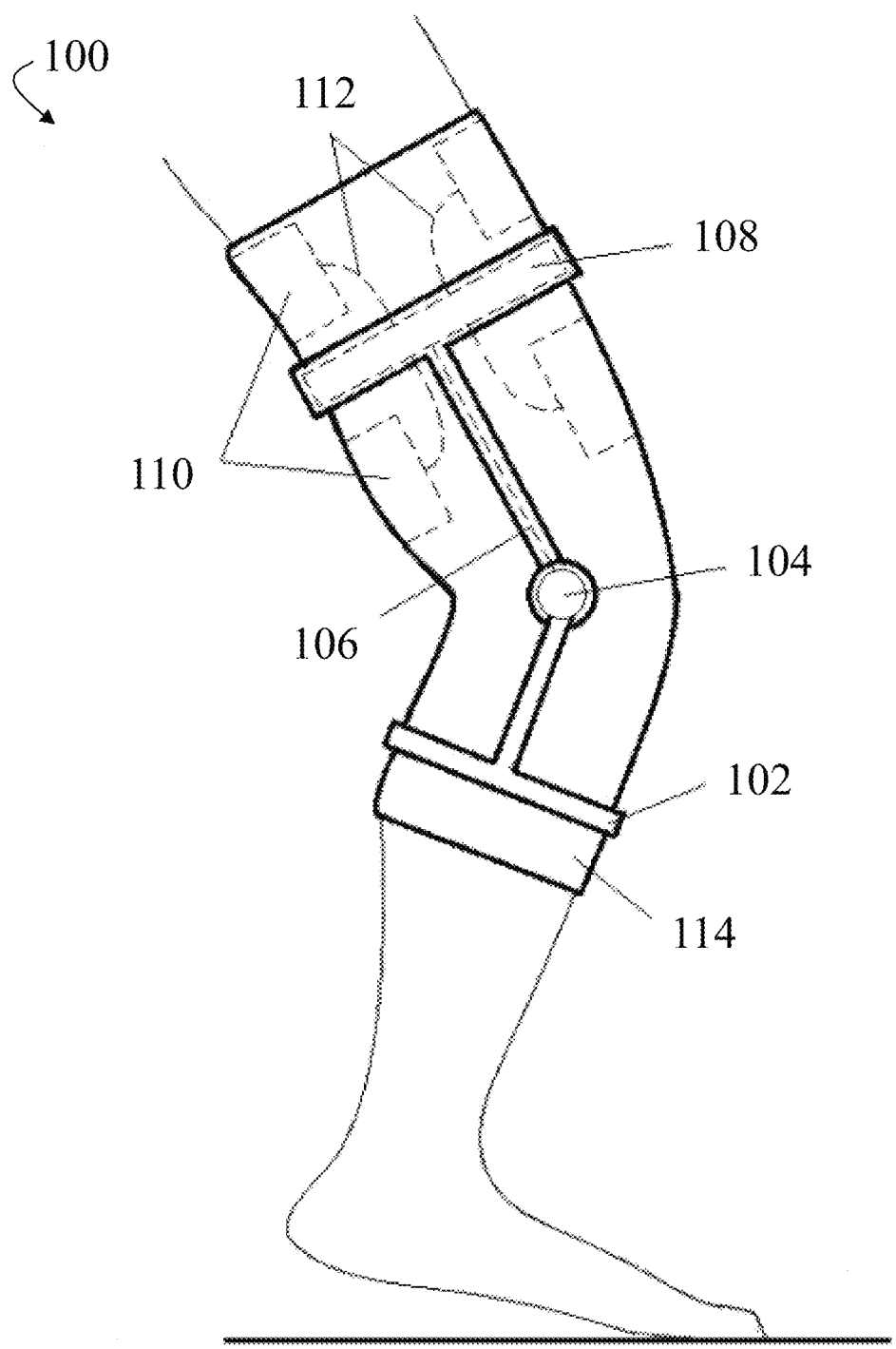
FIG. 1 shows an exemplary schematic illustration of a hybrid orthotic device comprising a knee brace, according to some embodiments.

Hybrid orthotic devices configured to apply electrical stimulation to one or more body parts of a person are generally described. Control of hybrid orthotic devices to provide exercise and rehabilitation of injured limbs is also described, as are control techniques suitable for controlling an orthotic device to aid a wearer perform an activity such as cycling.

Some aspects relate to functional electrical stimulation (FES) cycling devices and associated methods. An FES cycling device may comprise a crank, two or more pedals connected to the crank, one or more sensors adapted to measure position and/or velocity of the crank, and one or more electrodes configured to deliver electrical stimulation to a person associated with the cycling device. In some cases, the FES cycling device further comprises a controller configured to receive input signals from the one or more sensors and deliver output signals to the one or more electrodes. In certain cases, the controller may dynamically generate a control signal to deliver an amount of electrical stimulation to a muscle group (e.g., quadriceps femoris, gluteal muscles, hamstring muscles) based on the value of a determined torque transfer ratio between a joint of the person and the crank of the cycling device. The electrical stimulation may, in some cases, cause the person to pedal the cycling device.

In some embodiments, a hybrid orthotic device comprises one or more sensors, one or more electrodes, and a controller configured to receive input signals from the one or more sensors and deliver output signals to the one or more electrodes. In some embodiments, the controller may be nonlinear in that stimulus signals generated by the controller may be different in different contexts, even for the same inputs to the controller. In certain cases, the nonlinear controller may be configured to store one or more programs, which may, when executed, implement algorithms as described herein. The one or more programs may be associated, in some embodiments, with functional activities (e.g., standing, sitting, and/or walking), and the programs may be configured to enable one or more body parts of a wearer to track a desired trajectory. In some embodiments, a program may implement a Robust Integral of the Sign of the Error (RISE) control method, which will be discussed in more detail below. It may be desirable, in some cases, to implement a RISE-based control method, at least in part because such methods may achieve asymptotic stability, even in the presence of unknown, additive disturbances and parametric uncertainties in a nonlinear system. A RISE-based control method does not require knowledge of a muscle model. It may also be desirable to implement a RISE-based control method because such methods may be continuous. In some cases, a program may further implement control methods to compensate for electromechanical delay and/or muscle fatigue. In certain embodiments, a program may further implement adaptive learning methods, such as neural network (NN)-based methods.

In some embodiments, the hybrid orthotic device comprises one or more sensors. In certain cases, at least one of the sensors may be an electrogoniometer. Generally, an electrogoniometer refers to an instrument for measuring angles. In some cases, the electrogoniometer may be attached to the hybrid orthotic device so as to measure the angle between a first body part of a person and a second body part of a person, coupled at a joint, and to which the hybrid orthotic device may be attached. In certain embodiments, at least one of the sensors may be a pressure sensor. In some such embodiments, the pressure sensor may, for example, measure pressure applied by a body part (e.g., a foot) on a surface (e.g., the ground). In some embodiments, at least one of the sensors may be configured to measure velocity of a joint.

The hybrid orthotic device may comprise one or more electrodes. In some embodiments, at least one of the electrodes may be configured to apply electrical stimulation to one or more body parts of a person. For example, at least one of the electrodes may be configured to apply electrical stimulation to the skin of a person and to one or more underlying skeletal muscles. The stimulation may cause the muscles to contract, when above a level, or allow the muscle to relax when below a level. Non-limiting examples of skeletal muscles and muscle groups that may be stimulated, based on configuration of the hybrid orthotic device, include the quadriceps femoris, hamstrings, gluteal muscles, triceps surae, tibialis anterior, and biceps femoris. For example, it may be desirable to apply electrical stimulation to portions of the quadriceps femoris muscle group to induce extension of a knee as part of a functional activity, such as standing, sitting, and/or walking. In some embodiments, the electrodes may be bipolar electrodes. In certain cases, the electrodes may be self-adhesive electrodes, and may be rigidly coupled to structural members of the hybrid orthotic device and/or separately attached to a wearer of the device. In some cases, the orthotic device may comprise at least two electrodes.

The hybrid orthotic device may further comprise a controller. In some embodiments, the controller may be a nonlinear controller configured to receive input signals from one or more sensors and deliver output signals to one or more electrodes. The controller may, in certain cases, generate output signals as a nonlinear function of the input signals based at least in part on a determined parameter indicative of muscle fatigue. In some embodiments, the controller may be connected to one or more sensors via electrical leads. In some cases, the electrical leads may comprise power and/or data lines. For example, in certain embodiments, power may be transferred from the controller to the one or more sensors, and data may be transferred from the one or more sensors to the controller. In some embodiments, the controller may be connected to one or more electrodes via electrical leads. In certain cases, the electrical leads may be one-way leads. For example, in some cases, signals may be transferred from the controller to the one or more electrodes, but no data may be transferred from the electrodes to the controller. In some cases, the controller may be connected to at least two electrodes. The controller may be configured to deliver interleaved output signals to the at least two electrodes. In some embodiments, the controller may comprise inputs and outputs for connecting with a computer, for example for programming and/or data logging. The controller may, in some cases, be configured to record data from previous activities.

In some cases, the nonlinear controller may be configured to store one or more programs. The one or more programs may be associated, in some embodiments, with one or more functional activities, and the programs may be configured to enable one or more body parts of the person to track a desired trajectory. In some embodiments, a program may implement a closed-loop control method. A program may, in certain cases, implement a continuous feedback control method. In some cases, a program may implement a control method that yields asymptotic stability for a nonlinear system (e.g., muscle model) in the presence of bounded nonlinear disturbances (e.g., muscle spasticity, electromechanical delays, muscle fatigue). In some embodiments, the program may implement a control method that tracks the time-varying trajectory of at least one body part of the person. The program may, in certain cases, implement a RISE-based control method. In some cases, a program may further implement control methods to compensate for electromechanical delay and/or muscle fatigue. For example, the control method may comprise a predictor-type method to compensate for electromechanical delay. In certain embodiments, a program may further implement adaptive learning methods. For example, a program may implement a control method comprising an adaptive feedforward method. In some embodiments, the adaptive learning methods may comprise neural network (NN)-based methods.

The programs, when executed, may cause the controller to receive and process outputs of one or more sensors and, based on those outputs and/or other data, derive one or more stimulus signals to apply to one or more electrodes. The stimulus signals may have one or more characteristics that change over time, such that the stimulus applied to muscles of a wearer is modulated. In some cases, the program may implement a voltage modulation scheme (e.g., with a fixed frequency and a fixed pulse width) and/or a pulse width modulation scheme (e.g., with a fixed voltage and a fixed frequency). In some cases, the program may implement a frequency modulation scheme (e.g., with a fixed voltage and a fixed pulse width).

One problem that may arise during NMES is rapid onset of muscle fatigue during repeated contractions. The onset of muscle fatigue may be correlated with stimulation parameters such as intensity, frequency, and pattern of stimulation, with higher stimulation frequencies causing muscle to fatigue faster. The controller may be configured to generate stimulus signals based on passage of time or indicators of fatigue. In some embodiments, the program may implement a scheme comprising feedback-based frequency modulation to reduce fatigue. In certain cases, the program may implement a modulation scheme that adjusts frequency to maintain body part position tracking error within a specified range. For example, in some cases, the stimulation frequency may be progressively increased or decreased. Starting with a low frequency and changing to a high frequency when muscle output dictates higher demands may more closely mimic biological approaches than constant frequency schemes. In some cases, the program may implement a control method that increases and/or decreases the amplitude and/or frequency of the output signals according to a predefined rule. In certain embodiments, the program may implement a control method that modulates the amplitude and/or frequency of the output signals based at least in part on a value of a parameters indicative of muscle fatigue.

The hybrid orthotic device may comprise a bracing element configured to attach to a limb of a person. In some embodiments, the bracing element comprises one or more cuffs. In some embodiments, the bracing element may comprise a first cuff configured to attach to a first body part of a person and a second cuff configured to attach to a second body part of a person, where the first body part and second body part are coupled at a joint (e.g., knee, ankle, elbow, shoulder, wrist, hip). The cuffs may be adjustable and may be tightened or loosened (e.g., such that the cuff fits around a limb, such as a leg). In some cases, the cuffs may be substantially flexible (e.g., resilient), semi-rigid, or substantially rigid (e.g., non-resilient). The cuffs may comprise materials including, but not limited to, fabric (e.g., polyester, nylon, neoprene), plastic, and/or metal (e.g., aluminum). The cuffs may be fastened by any suitable fastener, including those now known in the art. For example, the cuffs may be fastened by one or more Velcro fasteners, buckles, and/or hook fasteners. In some embodiments, the bracing element may further comprise a sleeve. The sleeve may be substantially flexible (e.g., such that it can conform to the limb and/or joint). In certain embodiments, the sleeve may comprise a fabric. The bracing element may, in some cases, allow hinged movement of the joint (e.g., may not inhibit flexion and/or extension of the joint). In some embodiments, the bracing element may advantageously provide lateral and/or rotational stability to the joint. For example, the bracing element may prevent hyperextension and/or excessive rotation of the joint.

In some embodiments, the hybrid orthotic device may further comprise one or more elastic resistance elements. The elastic resistance element may comprise a first end secured to a first location on the bracing element and a second end secured to a second location on the bracing element. In certain cases, the elastic resistance element may comprise a spring and/or an elastic band. It may be desirable, in some cases, for the orthotic device to comprise an elastic resistance element for use in exercising one or more parts of the body.

FIG. 1 shows an exemplary schematic illustration of a hybrid orthotic device, according to some embodiments of the invention. In FIG. 1, hybrid orthotic device 100 comprises bracing element 102, which is configured to be worn on a leg. In some embodiments, the bracing element may comprise one or more cuffs. For example, in FIG. 1, bracing element 102 comprises two cuffs: one that can be positioned around the lower leg, and one that can be positioned around the thigh. In some embodiments, one or more sensors and their associated electrical leads may be embedded in the bracing element. For example, in FIG. 1, sensor 104 and electrical leads 106 are embedded in bracing element 102, with sensor 104 located at a hinge of bracing element 102 located between the two cuffs. Sensor 104 may, in some cases, be an electrogoniometer configured to measure joint angle. Electrical leads 106 may connect sensor 104 to a controller 108, which may also be attached to bracing element 102. The controller may comprise a portable power supply (e.g., batteries) and inputs and outputs for interfacing with sensors, electrodes, and/or external computers. For example, controller 108 may be configured to send power to and receive data (e.g., data about the joint angle) from sensor 104 via electrical leads 106. Controller 108 may also be configured to receive and store programs from and send data to an external computer. Additionally, controller 108 may also be configured to send output stimulation signals to electrodes 110 via electrical leads 112 to cause contractions of the muscles of the wearer to induce a desired joint motion. In some embodiments, leads 112 may be one-way leads (e.g., data may not be transmitted from electrodes 110 to controller 108). In FIG. 1, electrodes 110 and leads 112 are embedded in a sleeve 114. Sleeve 114, which may comprise a flexible material and conform to the joint and leg, may be positioned under bracing element 102. In some embodiments, electrodes 110 may be configured to be in contact with the skin of a person and to transmit electrical stimulation to underlying muscle. In some embodiments, electrodes 110 may be used to activate different muscle groups at the same time.

Figure 2:
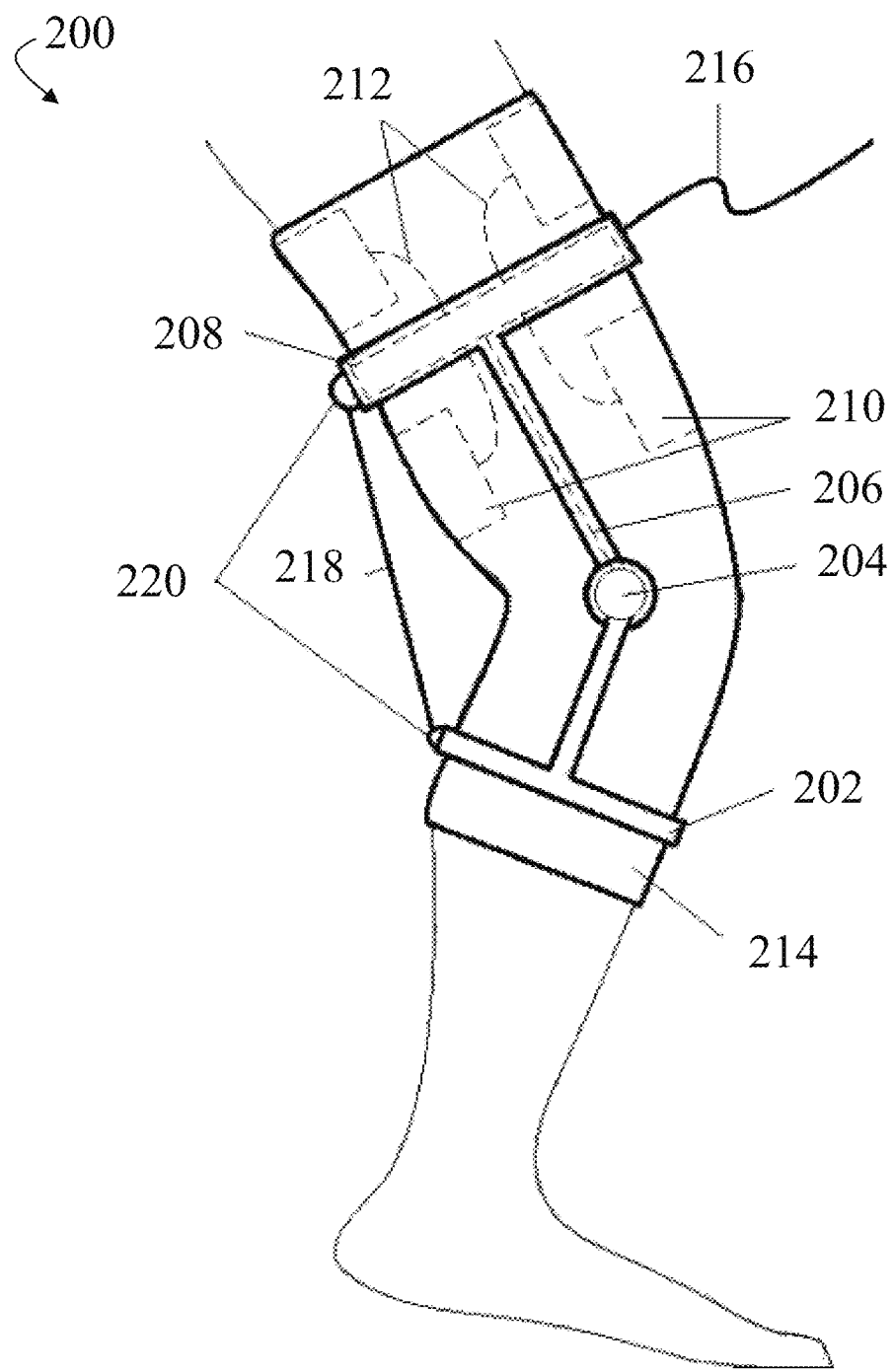
FIG. 2 shows, according to some embodiments, an exemplary schematic illustration of a hybrid orthotic device comprising a knee brace and elastic resistance elements.

An exemplary schematic illustration of a hybrid orthotic device comprising elastic resistance elements is shown in FIG. 2. Like orthotic device 100 in FIG. 1, orthotic device 200 in FIG. 2 comprises a bracing element 202 and a sensor 204, which is connected to controller 208 via electrical leads 206. Sensor 204, electrical leads 206, and controller 208 are embedded in bracing element 202. In FIG. 2, controller 208 is connected to a cable 216. Controller 208 may be configured to receive power from an external power source via cable 216. Controller 208 may also be configured to communicate with an external computer in real time (e.g., for data logging and/or visualization) via cable 216. Additionally, controller 208 is connected to electrodes 210 via electrical leads 212. Electrodes 210 and electrical leads 212 are embedded in a sleeve 214. Orthotic device 200 also comprises elastic resistance element 218, which is attached to bracing element 202 via anchors 220. Elastic resistance element 218 may be a tension or compression element. In some cases, it may be desirable for an orthotic device to comprise one or more elastic resistance elements for exercising a joint. Anchors 220 may allow elastic resistance element 218 to be easily removed and replaced, facilitating exercise that calls for progressive increase and/or decrease of resistance.

Figure 3:
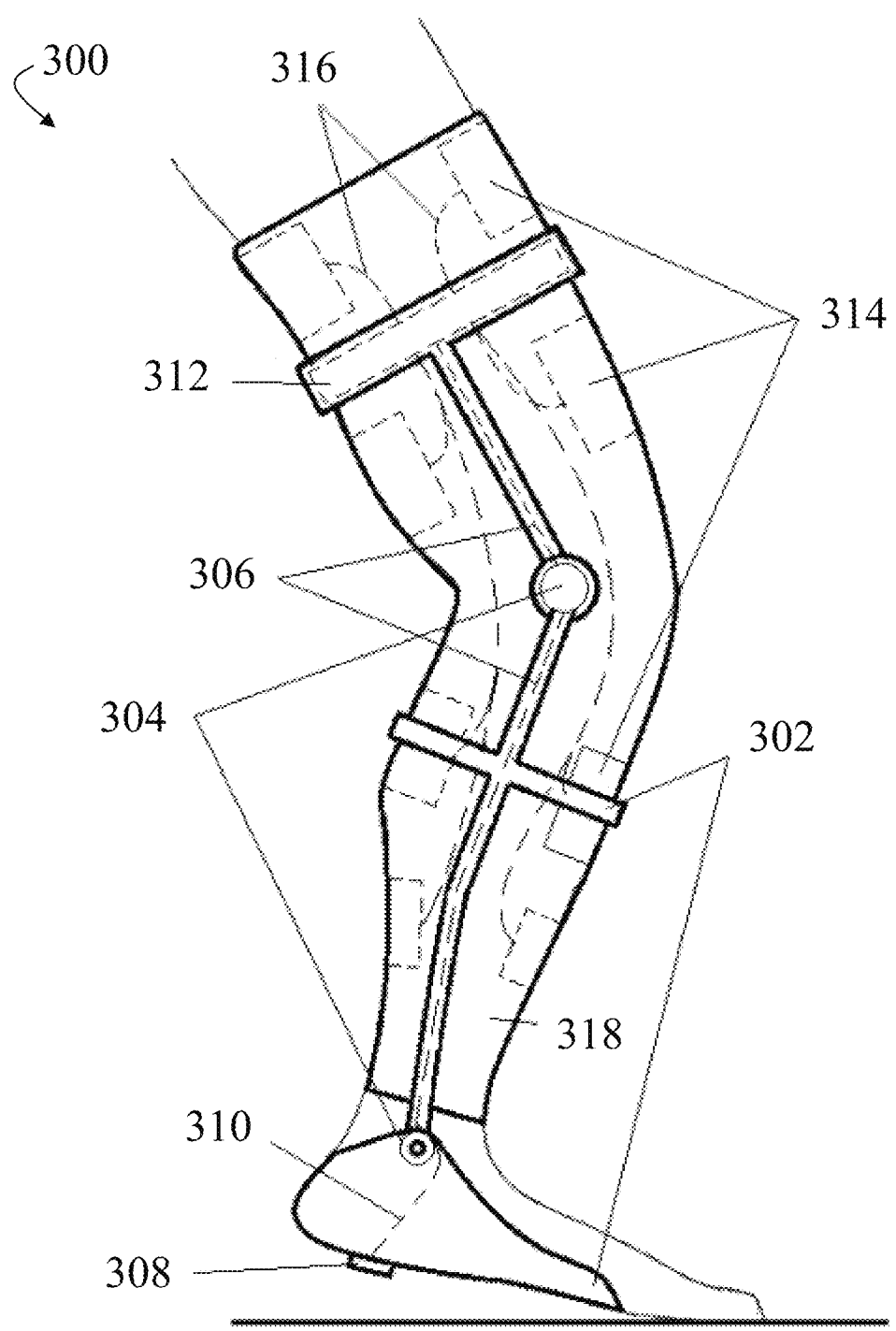
FIG. 3 shows an exemplary schematic illustration of a hybrid orthotic device comprising a knee and ankle brace, according to some embodiments.

FIG. 3 shows an exemplary schematic illustration of a hybrid orthotic device configured to induce movement about the knee and/or ankle joints, according to some embodiments. In FIG. 3, orthotic device 300, which is a knee-ankle-foot orthosis, comprises bracing element 302. Bracing element 302 may comprise one or more hinges and may be substantially flexible, semi-rigid, or rigid. In FIG. 3, bracing element 302 comprises a first adjustable cuff configured to attach to a lower leg and a second adjustable cuff configured to attach to a thigh. Bracing element 302 further comprises a foot piece designed to fit inside a shoe for a foot. A pressure sensor 308 may be in direct contact with the foot piece. Pressure sensor 308 may be configured to collect data relating to contact between the foot and an external surface (e.g., the ground) and to transmit the data to a controller 312 via electrical lead 310. In FIG. 3, additional sensors 304 are embedded in bracing element 302. In some embodiments, at least one of sensors 304 is an electrogoniometer. The electrogoniometer may measure, for example, knee and/or ankle angle. Sensors 304 may be configured to transmit data to controller 312 via electrical leads 306. In some cases, electrical leads 306 and 310 may comprise power and data lines. In FIG. 3, controller 312 is also connected to electrodes 314 via electrical leads 316. Electrodes 314 and electrical leads 316 may be embedded in sleeve 318. In some embodiments, electrodes 314 may be configured to apply stimulation to induce flexion, extension, or rotation of the knee and/or ankle.

Figure 4:
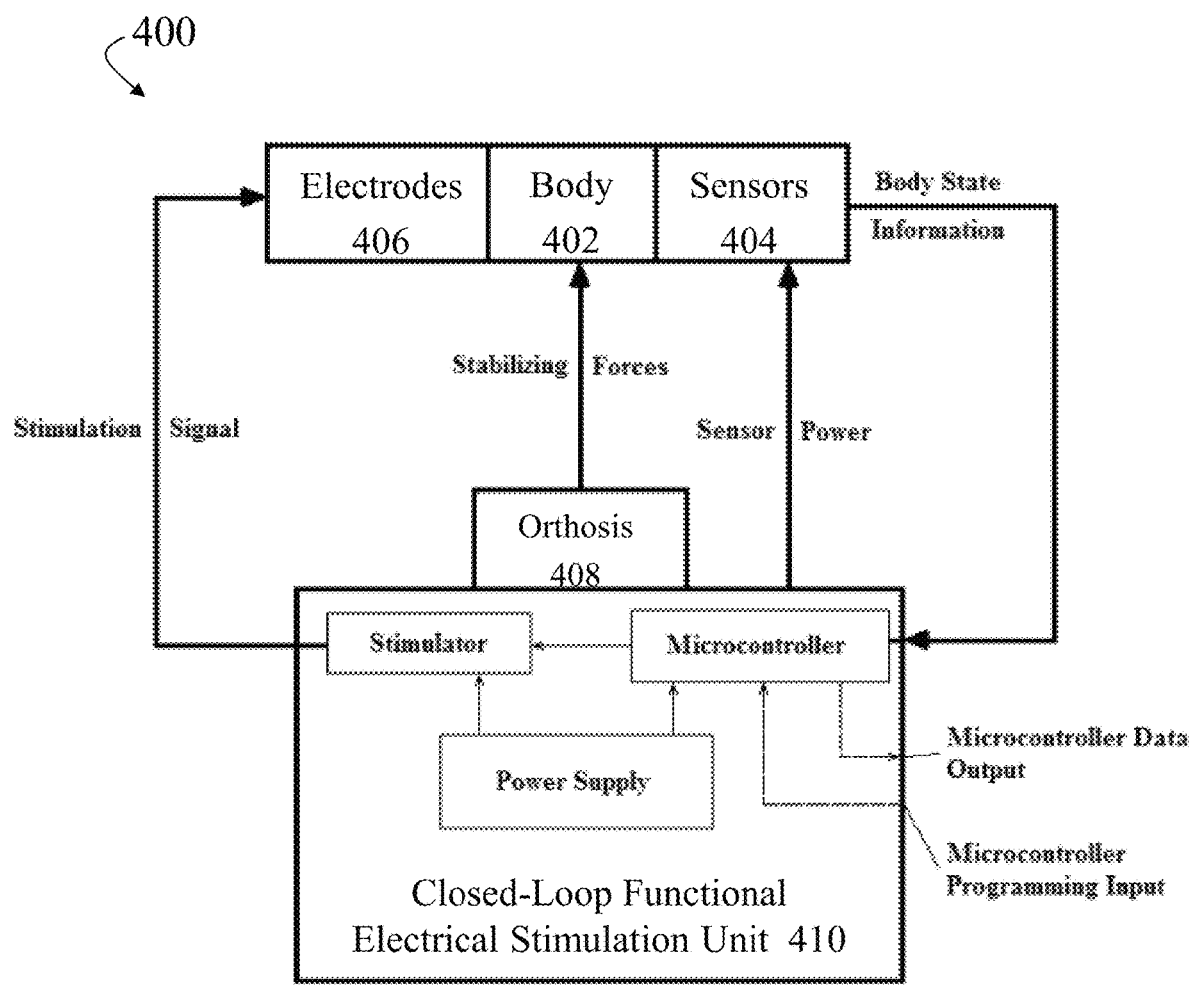
FIG. 4 shows an exemplary block diagram of a system comprising a portable closed-loop functional electrical stimulation unit, according to some embodiments.

FIG. 4 displays an exemplary schematic block diagram illustrating the interactions between components of a system comprising a hybrid orthotic device, according to some embodiments. It should be appreciated that FIG. 4 is a functional block diagram and the components represented in that block diagram may be configured and positioned in any suitable way, including as illustrated in any of FIGS. 1-3. In FIG. 4, system 400 comprises a body 402, sensors 404, electrodes 406, orthosis 408, and a closed-loop functional electrical stimulation (CL-FES) unit 410. Sensors 404 are in direct contact with body 402, and they transmit body state information to CL-FES unit 410. CL-FES unit 410 comprises a microcontroller, a stimulator, and a power supply. The power supply may supply power to the microcontroller and the stimulator, and may additionally supply power to sensors 404. The microcontroller receives body state information from sensors 404. Additionally, the microcontroller is configured to receive programming input from an external computer and to transmit data to the external computer. Though, in some embodiments, a connection to an external computer may be active while the device is in operation to enable the external computer to perform some or all of the control functions. The microcontroller can also send information to the stimulator, which transmits a stimulation signal to electrodes 406. Electrodes 406 are in direct contact with body 402, and the electrical stimulation may induce movement of body 402 such that a functional activity may be performed. CL-FES unit 410 is also in direct contact with an orthosis 408, which may provide stabilizing forces to body 402.

Figure 5:
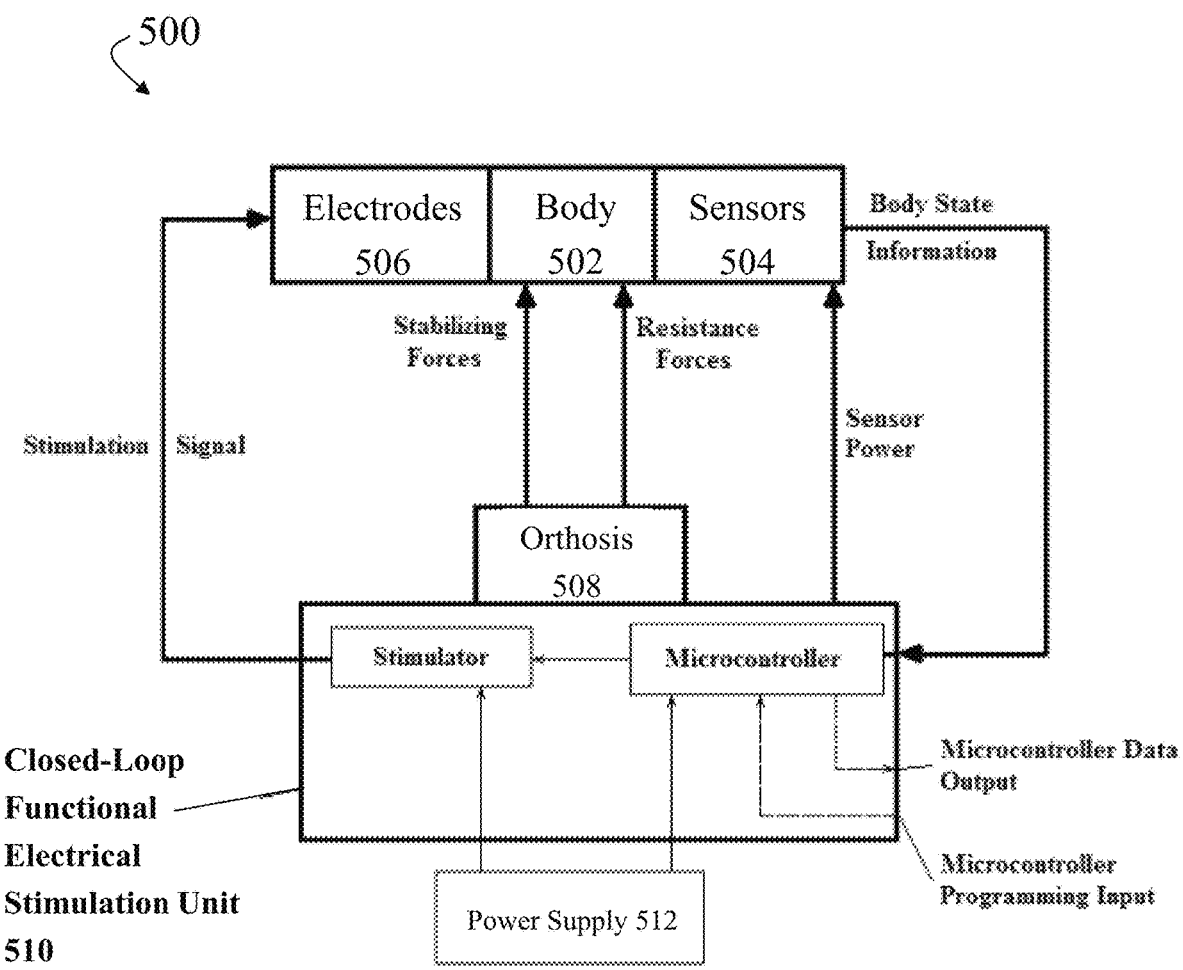
FIG. 5 shows, according to some embodiments, an exemplary block diagram of a system comprising an externally-powered closed-loop functional electrical stimulation unit.

An exemplary schematic block diagram illustrating the interactions between components of a system 500 comprising an externally-powered hybrid orthotic device, according to some embodiments, is shown in FIG. 5. In FIG. 5, system 500 comprises a body 502, sensors 504, electrodes 506, and orthosis 508. In FIG. 5, CL-FES unit 510 comprises a stimulator and microcontroller, like CL-FES unit 410. However, unlike CL-FES unit 410, CL-FES unit 510 does not comprise a power source. Rather, power is supplied from external power supply 512. Additionally, in FIG. 5, CL-FES unit 510 is in direct contact with orthosis 508, which comprises one or more elastic resistance units. Orthosis 508 is therefore configured to provide not only stabilizing forces but also resistance forces to body 502.

Figure 6:
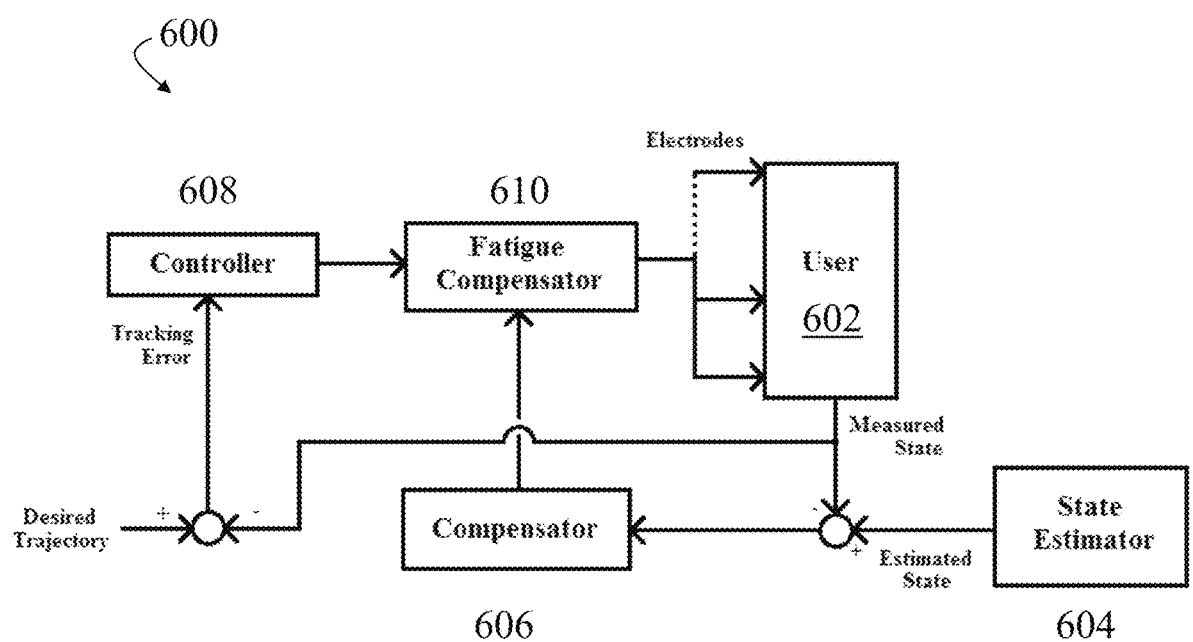
FIG. 6 shows an exemplary block diagram of a system comprising a controller for an orthotic device, according to some embodiments.

FIG. 6 displays an exemplary schematic block diagram illustrating the interactions between components of a controller in a system 600, according to some embodiments. In FIG. 6, a state of user 602 is measured. The state may be represented in whole or in part by sensor outputs and may include, for example, joint angle. The measured state may then be compared to the state estimated by state estimator 604. The difference between the measured state and the estimated state may be sent to compensator 606, which utilizes a compensating method to compensate for differences between the measured and estimated states. The measured state may also be compared to the desired trajectory, and the tracking error may be sent to controller 608. Controller 608 utilizes a control method to minimize the tracking error and calculate the amplitude, frequency, and pulse width of output signals (which may serve as stimulus signals input to electrodes) to enable user 602 to most closely follow the desired trajectory. Output from compensator 606 and controller 608 may be sent to fatigue compensator 610, which compensates for muscle fatigue induced by electrical stimulation. Compensation, for example, may increase stimulation as increased fatigue is measured. The output signals may then be sent to electrodes to apply electrical stimulation to user 602.

Some embodiments relate to methods of providing functional electrical stimulation to a person. For example, a method may comprise the step of receiving signals from at least one sensor. Additionally, the method may comprise the steps of calculating an amount of electrical stimulation to apply to at least one body part of the person and delivering electrical stimulation to the at least one body part of the person.

In some embodiments, delivering electrical stimulation to at least one body part of a person assists the person in interacting with an external device. For example, functional electrical stimulation may be used to assist a person in pedaling a cycling device (e.g., a stationary bicycle, a mobile bicycle, a mobile tricycle). A cycling device may, in some cases, comprise a crank and two pedals, where each pedal is connected to an end of the crank. In some embodiments, the cycling device further comprises at least one wheel (e.g., two wheels, three wheels, four wheels). The cycling device may, in some cases, further comprise one or more sensors. In some cases, at least one sensor is configured to measure position and/or velocity of the crank of the cycling device. In some cases, at least one sensor is an electrogoniometer. According to certain embodiments, the cycling device optionally comprises a motor (e.g., an electric motor) connected to the crank (e.g., such that the motor may provide power to the crank). A person may be associated with the cycling device such that a first lower limb (e.g., a foot) of a person is in contact with a first pedal of the cycling device. In some cases, a second lower limb (e.g., a foot) of the person is in contact with a second pedal of the cycling device.

In certain embodiments, electrical stimulation is delivered to a first leg of a person via at least one electrode (e.g., two electrodes, three electrodes, four electrodes, or more), inducing pedaling of a cycling device. In some cases, the pedaling is forward pedaling. In some cases, the pedaling is backward pedaling. In certain embodiments, electrical stimulation is delivered to a second, different leg of the person via at least one electrode (e.g., two electrodes, three electrodes, four electrodes, or more), inducing pedaling (e.g., forward pedaling and/or backward pedaling) of the cycling device. In some cases, the pedaling may be substantially continuous for an amount of time. In some embodiments, substantially continuous pedaling occurs for a period of at least about 1 minute, at least about 5 minutes, at least about 10 minutes, at least about 15 minutes, at least about 20 minutes, at least about 30 minutes, at least about 60 minutes, or at least about 90 minutes. Substantially continuous pedaling may occur for a period ranging from about 1 minute to about 5 minutes, about 5 minutes to about 15 minutes, about 5 minutes to about 20 minutes, about 5 minutes to about 30 minutes, about 5 minutes to about 60 minutes, about 5 minutes to about 90 minutes, about 10 minutes to about 30 minutes, about 10 minutes to about 60 minutes, about 10 minutes to about 90 minutes, about 30 minutes to about 60 minutes, about 30 minutes to about 90 minutes, or about 60 minutes to about 90 minutes.

In some embodiments, a method comprises delivering a first amount of electrical stimulation to a first leg of a person for a first amount of time. In some embodiments, the first amount of electrical stimulation is applied during a first portion of a crank trajectory cycle. In certain cases, the electrical stimulation activates at least a portion of the quadriceps femoris muscles of the first leg. In some embodiments, the electrical stimulation activates at least a portion of the gluteal muscles, hamstring muscles, and/or calf muscles of the first leg. In certain embodiments, electrical stimulation is applied to two or more muscle groups of the first leg during the first amount of time. The same or different amounts of electrical stimulation may be applied to the two or more muscle groups of the first leg during the first amount of time.

According to some embodiments, the first amount of electrical stimulation is applied to a muscle group (e.g., quadriceps femoris, gluteal muscles, hamstring muscles, calf muscles) when a torque transfer ratio for the muscle group has a certain sign (e.g., positive, negative). For example, in some cases, forward pedaling about a crank of a cycling device (e.g., clockwise in FIGS. 7 and 13) may be desirable, and a muscle group may be activated when it yields a forward torque about the crank. A muscle group may yield a forward torque when the torque transfer ratio is positive or negative, depending on the muscle group. In certain embodiments, the first amount of electrical stimulation is applied when a torque transfer ratio between the hip or the knee of the first leg and the crank of the cycling device is negative. In some cases, the first amount of electrical stimulation is applied to at least a portion of the quadriceps femoris when the torque transfer ratio for the quadriceps femoris is negative. In certain embodiments, the first amount of electrical stimulation is applied when a torque transfer ratio between the hip or the knee of the first leg and the crank of the cycling device is positive. In some embodiments, the first amount of electrical stimulation is applied to at least a portion of the gluteal muscles when the torque transfer ratio for the gluteal muscles is positive. In some embodiments, the first amount of electrical stimulation is applied to at least a portion of the hamstring muscles when the torque transfer ratio for the hamstring muscles is positive.

In certain embodiments, the first amount of electrical stimulation is applied to a muscle group when the magnitude of the torque transfer ratio for the muscle group is above a certain threshold (e.g., at least about 0.1). In some cases, electrical stimulation of a muscle group only when its torque transfer ratio is above a certain threshold may enhance efficiency by avoiding stimulation that would result in relatively low power output at the crank of the cycling device.

In some embodiments, a method comprises delivering a second amount of electrical stimulation to a second, different leg for a second amount of time. In some embodiments, the second amount of electrical stimulation is applied during a second portion of a crank trajectory cycle. In certain cases, the electrical stimulation activates at least a portion of the quadriceps femoris muscles of the second leg. In some embodiments, the electrical stimulation activates at least a portion of the gluteal muscles, hamstring muscles, and/or calf muscles of the second leg. In certain embodiments, electrical stimulation is applied to two or more muscle groups of the second leg during the second amount of time. The same or different amounts of electrical stimulation may be applied to the two or more muscle groups of the second leg during the second amount of time.

In some embodiments, the second amount of electrical stimulation is applied to a muscle group (e.g., quadriceps femoris, gluteal muscles, hamstring muscles, calf muscles) when a torque transfer ratio for the muscle group has a certain sign (e.g., positive, negative). In certain embodiments, the second amount of electrical stimulation is applied when a torque transfer ratio between the knee of the second leg and the crank is negative. In some cases, the second amount of electrical stimulation is applied to at least a portion of the quadriceps femoris when the torque transfer ratio for the quadriceps femoris is negative. In certain embodiments, the second amount of electrical stimulation is applied when a torque transfer ratio between the hip or the knee of the first leg and the crank of the cycling device is positive. In some embodiments, the second amount of electrical stimulation is applied to at least a portion of the gluteal muscles when the torque transfer ratio for the gluteal muscles is positive. In some embodiments, the second amount of electrical stimulation is applied to at least a portion of the hamstring muscles when the torque transfer ratio for the hamstring muscles is positive.

In certain embodiments, the second amount of electrical stimulation is applied to a muscle group when the magnitude of the torque transfer ratio for the muscle group is above a certain threshold (e.g., at least about 0.1).

In some cases, the first amount of electrical stimulation and second amount of electrical stimulation are substantially the same. In some cases, the first amount of electrical stimulation and second amount of electrical stimulation are different. In certain embodiments, the first amount of time and second amount of time are substantially the same. In some embodiments, the first amount of time and second amount of time are different. In some embodiments, electrical stimulation is not applied to the first leg and the second leg at the same time (e.g., electrical stimulation is alternately applied to a first leg, then a second leg, then the first leg, etc.). In some embodiments, the first portion of the crank trajectory cycle and the second portion of the crank trajectory cycle do not overlap.

According to some embodiments, a motor (e.g., an electric motor) provides power to the crank of the cycling device during at least a portion of the crank trajectory cycle. In some cases, a motor may advantageously supplement the ability of a person's muscles to provide power to the crank. In certain embodiments, the motor may promote stability. However, in order to promote efficiency, it may be desirable for the motor to provide assistance only during certain portions of the crank trajectory cycle. For example, it may be advantageous, in some cases, for the motor to provide power to the crank when the kinematic effectiveness of one or more stimulated muscle groups is relatively low. In some cases, during a first portion of a crank trajectory cycle, only motor input may be received (e.g., power is generated by the motor and no electrical stimulation is applied to the person's muscles). In some cases, during a second portion of the crank trajectory cycle, only functional electrical stimulation (FES) input may be received (e.g., electrical stimulation is applied to one or more muscle groups of the person and no power is generated by the motor). In certain embodiments, during a third portion of the crank trajectory cycle, both motor and FES input may be received. A crank trajectory may comprise any combination of the first, second, and third portions described above. In some embodiments, at least one sensor and/or at least one electrode is connected (e.g., electrically connected) to a controller. In some cases, the controller is adapted to receive an input signal from at least one sensor and deliver an output signal to at least one electrode. In some cases, the first amount of electrical stimulation, second amount of electrical stimulation, first amount of time, second amount of time, first portion of the crank trajectory cycle, and/or second portion of the crank trajectory cycle are calculated using a control method. In certain cases, the controller may dynamically generate a signal to control delivery of electrical stimulation based on a torque transfer ratio between a joint of the person and the crank of the cycling device. The control method may, in some cases, be a nonlinear control method. The control method may be discontinuous or continuous. In some cases, the control method is exponentially stable. In certain embodiments, the control method is a switched sliding mode control method.

In some embodiments, electrical stimulation of one or more muscle groups of a person induces cycling at a relatively high cadence (e.g., pedal velocity). In some embodiments, the mean pedal cadence is at least about 5 revolutions per minute (rpm), at least about 10 rpm, at least about 15 rpm, at least about 20 rpm, at least about 30 rpm, at least about 50 rpm, at least about 70 rpm, or at least about 100 rpm. In some cases, the mean pedal cadence is in the range of about 5 rpm to about 10 rpm, about 5 rpm to about 20 rpm, about 5 rpm to about 50 rpm, about 5 rpm to about 100 rpm, about 10 rpm to about 20 rpm, about 10 rpm to about 50 rpm, about 10 rpm to about 100 rpm, about 20 rpm to about 50 rpm, about 20 rpm to about 100 rpm, or about 50 rpm to about 100 rpm.

In some embodiments, the mean cadence tracking error (e.g., the numerical average of the differences between desired cadence and actual cadence achieved) is relatively small. In some cases, the mean cadence tracking error is about 10 rpm or less, about 5 rpm or less, about 2 rpm or less, about 1 rpm or less, about 0.5 rpm or less, about 0.4 rpm or less, about 0.3 rpm or less, about 0.2 rpm or less, about 0.1 rpm or less, about 0.05 rpm or less, about 0.02 rpm or less, or about 0.01 rpm or less. In some embodiments, the mean cadence tracking error is in the range of about 0 rpm to about 0.1 rpm, about 0 rpm to about 0.2 rpm, about 0 rpm to about 0.3 rpm, about 0 rpm to about 0.4 rpm, about 0 rpm to about 0.5 rpm, about 0 rpm to about 0.6 rpm, about 0 rpm to about 0.7 rpm, about 0 rpm to about 0.8 rpm, about 0 rpm to about 0.9 rpm, about 0 rpm to about 1 rpm, about 0 rpm to about 2 rpm, about 0 rpm to about 5 rpm, or about 0 rpm to about 10 rpm.

In certain embodiments, the standard deviation of the cadence tracking error is relatively small. In some cases, the standard deviation of the cadence tracking error is about 10 rpm or less, about 5 rpm or less, about 2 rpm or less, about 1 rpm or less, about 0.5 rpm or less, about 0.4 rpm or less, about 0.3 rpm or less, about 0.2 rpm or less, about 0.1 rpm or less, about 0.05 rpm or less, about 0.02 rpm or less, or about 0.01 rpm or less. In some embodiments, the standard deviation of the cadence tracking error is in the range of about 0 rpm to about 0.1 rpm, about 0 rpm to about 0.2 rpm, about 0 rpm to about 0.3 rpm, about 0 rpm to about 0.4 rpm, about 0 rpm to about 0.5 rpm, about 0 rpm to about 0.6 rpm, about 0 rpm to about 0.7 rpm, about 0 rpm to about 0.8 rpm, about 0 rpm to about 0.9 rpm, about 0 rpm to about 1 rpm, about 0 rpm to about 2 rpm, about 0 rpm to about 5 rpm, or about 0 rpm to about 10 rpm.

In certain cases, the root mean square (RMS) of the cadence tracking error is relatively small. In some cases, the RMS of the cadence tracking error is about 10 rpm or less, about 5 rpm or less, about 2 rpm or less, about 1 rpm or less, about 0.5 rpm or less, about 0.4 rpm or less, about 0.3 rpm or less, about 0.2 rpm or less, about 0.1 rpm or less, about 0.05 rpm or less, about 0.02 rpm or less, or about 0.01 rpm or less. In some embodiments, the RMS of the cadence tracking error is in the range of about 0 rpm to about 0.1 rpm, about 0 rpm to about 0.2 rpm, about 0 rpm to about 0.3 rpm, about 0 rpm to about 0.4 rpm, about 0 rpm to about 0.5 rpm, about 0 rpm to about 0.6 rpm, about 0 rpm to about 0.7 rpm, about 0 rpm to about 0.8 rpm, about 0 rpm to about 0.9 rpm, about 0 rpm to about 1 rpm, about 0 rpm to about 2 rpm, about 0 rpm to about 5 rpm, or about 0 rpm to about 10 rpm.

In some embodiments, electrical stimulation is applied to a person with a disorder affecting movement of one or more limbs (e.g., legs). In certain cases, electrical stimulation is applied to a person completely lacking motor control of one or more limbs (e.g., a person having a complete spinal cord injury). In such cases, the person may be a completely passive rider on the cycling device. In certain cases, electrical stimulation is applied to a person having diminished motor control of one or more limbs. Non-limiting examples of disorders that may result in diminished motor control of one or more limbs (e.g., legs) include Parkinson's disease, incomplete spinal cord injury, cerebral palsy, multiple sclerosis, stroke, and/or traumatic brain injury.

Joint Model

It may be desirable, in some cases, to model the total dynamics of a joint to facilitate development of a controller that could enable movement about the joint to follow a desired trajectory. In some embodiments, the total dynamics of a joint can be modeled as:

$$M_I + M_e + M_g + M_v + \tau_d = \tau \quad (1)$$

where $M_I$ represents inertial effects of one or more body parts about the joint, $M_e$ represents elastic effects due to joint stiffness, $M_g$ represents gravitational effects, $M_v$ represents viscous effects due to damping in the musculotendon complex, $\tau_d$ represents one or more unknown bounded disturbances (e.g., muscle spasticity, dynamic fatigue, signal and response delays, changing muscle geometry, and/or load changes during functional tasks), and T represents the torque produced at the joint. The first and second time derivatives of unknown disturbance $\tau_d$ can be assumed to exist and to be bounded.

Inertial effects $M_I$ can be modeled, in some cases, as:

$$M_I(\ddot{q}(t)) = J\ddot{q}(t) \qquad (2)$$

where $\ddot{q}(t)$ denotes the angular acceleration of the one or more body parts about the joint, and J denotes the unknown inertia of the one or more body parts.

In certain cases, elastic effects $M_e$ can be modeled as:

$$M_e(g(t)) = -k_1 e^{-k_2 q(t)} (q(t) - k_3) \qquad (3)$$

where q(t) denotes the angular position of the one or more body parts about the joint, and $k_1$, $k_2$, and $k_3$ are unknown positive coefficients.

Gravitational effects $M_g$ may be modeled as:

$$M_g(q(t)) = mgl \sin(g(t)) \qquad (4)$$

where m denotes the unknown combined mass of the body parts, l is the unknown distance between the joint and the center of mass of the body parts, and g denotes the gravitational acceleration. Gravitational acceleration generally refers to the value of about 9.8 meters per second squared (m/s²).

Viscous effects $M_v$ may be modeled as:

$$M_v(\dot{q}(t)) = B_1 \tan h(-B_2 \dot{q}(t)) - B_3 \dot{q}(t) \qquad (5)$$

where $\dot{e}(t)$ denotes the angular velocity of the body parts about the joint and $B_1$, $B_2$, and $B_3$ are unknown positive constants.

Torque $\tau(t)$ about the joint may be produced through muscle tendon forces $F_T(t)$, such as those generated through electrical stimulation of one or more muscles. Torque $\tau(t)$ may be related to musculotendon force $F_T(t)$ through the relation:

$$\tau(t) = \zeta(q(t)) F_T(t) \qquad (6)$$

where $\zeta(q(t))$ represents a positive moment arm that changes with extension and movement of the body parts. The moment arm may have unique values for a given range of motion. The unique values may be considered continuously differentiable, positive, monotonic, and bounded. The unique values may also be considered to have a bounded first time derivative. The total musculotendon force may be a net sum of active forces generated by contractile, elastic, and viscous elements. The forces may have dynamic characteristics. For example, in some cases, a passive elastic element may increase with increasing muscle length. In some cases, the musculotendon force generated at the tendon may be the projection of the net sum of the elements along the line parallel to the tendon.

In some cases, the torque at the joint may be delayed. In some such cases, torque $\tau(t)$ may be represented by $u(t-t_\tau)$, where $t_\tau$ represents the electromechanical delay. The relation between the torque and musculotendon force may then be written as:

$$u(t-t_\tau) = \zeta(q(t)) F_T(t-t_\tau) \qquad (7)$$

In certain cases, the musculotendon force $F_T(t)$ may be modeled as:

$$F_T = F \cos a(q(t)) \qquad (8)$$

where a(q(t)) is the pennation angle between the tendon and the muscle. For example, for the human quadriceps muscle, the pennation angle may change monotonically during contraction and may be a continuously differentiable, positive, monotonic, and bounded function with a bounded first time derivative.

In some embodiments, there may be asynchronous electrical stimulation of one or more muscles. In some such cases, there may be N stimulation channels in the system. Since each channel can activate different sets of muscle units, the corresponding dynamics may be different depending on the switching signal. For example, the dynamics may be modeled as:

$$M_I + M_e + M_g + M_v \tau_d = \tau_i + \tau_j + \ldots + \tau_N \qquad (9)$$

where $\tau_i$ and $\tau_j$ represent the torque produced by stimulation of the $i^{th}$ and $j^{th}$ subsystems, respectively. The torque produced by stimulation of the $i^{th}$ subsystem may be related to the musculotendon force as:

$$\tau_i(t) = \zeta_i(q(t)) F_{T,i}(t) \qquad (10)$$

where musculotendon force $F_{T,i} = F_i \cos a_i (q)$ and $F_i$ is the force produced by the recruited muscle in the $i^{th}$ subsystem.

In some embodiments, the relationship between musculotendon force $F_T$ and the applied stimulation V(t) can be expressed as:

$$F_T(t) = \eta(t) V(t) \qquad (11)$$

where $\eta(t)$ is an unknown nonlinear function that is continuously differentiable, nonzero, positive, monotonic, and bounded, with a bounded first time derivative. In this example, V(t) may represent a voltage. However, the specific form in which the stimulus is applied is not critical to the invention, and the stimulus may be applied alternatively or additionally as a current or in any other suitable form. It may, in some cases, be desirable to introduce unknown nonlinear function $\eta(t)$, since it may enable the muscle contraction to be considered under general dynamic conditions in the subsequent control development. The unknown, uncertain function $\eta(t)$ can capture the dynamic characteristics of muscle recruitment, muscle force-length, and muscle force-velocity relationships, as well as active and passive characteristics. If electromechanical delay is taken into account, the relation may be written as:

$$F_T(t-t_v) = \eta(q(t), \dot{q}(t)) V(t-t_v) \qquad (12)$$

to capture the latency present between the application of stimulation and production of force.

Control Development

In some embodiments, a controller may enable one or more body parts coupled at a joint to track a desired trajectory $q_d(t)$, where $q_d(t)$ and its $i^{th}$ derivatives $q_d(t)$ are bounded and within the range of motion of the joint for i=1, 2, 3, and 4. In some cases, desired trajectory $q_d(t)$ may be based on joint kinetics and/or joint kinematics. In some embodiments, desired trajectory $q_d(t)$ may be based on body part position. Alternatively, the desired trajectory may comprise continuous signals, periodic signals, step functions, and/or sinusoidal functions. In some cases, the periodic signals may have different frequencies and/or the step functions may have changes in the dynamic load.

In some embodiments, a position tracking error may be defined as:

$$e_1(t) = q_d(t) - q(t) \qquad (13)$$

Two filtered tracking errors $e_2(t)$ and r(t) may be introduced to facilitate closed-loop error system development and stability analysis. Filtered tracking error $e_2(t)$ may be expressed as:

$$e_2(t) \triangleq \dot{e}_1(t) + \alpha_1 e_1(t) \qquad (14)$$

where $\alpha_1$ is a positive constant control gain.

Filtered tracking error r (t) may be expressed as:

$$r(t) \triangleq \dot{e}_2(t) + \alpha_2 e_2(t) \tag{15}$$

where $a_2$ is a positive constant control gain. In some cases, filtered tracking error r (t) may not be used in the controller due to a dependence on angular acceleration measurements. Multiplying Equation 16 by J and using the above expressions, the following expression can be obtained:

$$J\dot{r} = W - \Omega W + \tau_d \tag{16}$$

where auxiliary signal W is defined as:

$$W = j(\ddot{q}_d + \alpha_1 \dot{e}_1 + \alpha_2 e_2) + M_e + M_g + M_v \tag{17}$$

and auxiliary function $\Omega$ is defined as:

$$\Omega(q,t) \triangleq \zeta(q(t))\eta(t)\cos a(q(t)) \tag{18}$$

Multiplying Equation 16 by $\Omega^-$, the following expression can be obtained:

$$J_\Omega \dot{r} = W_\Omega - V + \tau_{d\Omega} \tag{19}$$

where $J_\Omega = \Omega^{-1} J$, $W_\Omega = \Omega^{-1} W = J_\Omega(\ddot{q}_d + \alpha_1 \dot{e}_1 + \alpha_2 e_2) + \Omega^{-1}(M_e + M_g + M_v)$, and $\tau_{d\Omega} = \Omega^{-1} \tau_d$.

In some cases, the following open-loop error system for Equation 19 may be obtained:

$$J_\Omega \dot{r} = -\frac{1}{2} \dot{J}_\Omega r + N - \dot{V} - e_2 \tag{20}$$

where N denotes the unmeasureable auxiliary term:

$$N = \dot{W}_\Omega + e_2 - \frac{1}{2} \dot{J}_\Omega r + \dot{\tau}_{d\Omega}(q, t) \tag{21}$$

In some embodiments, it may be desirable to obtain the above expressions for Equations 20 and 21 to facilitate stability analysis. Another unmeasureable auxiliary term $N_d$ may be defined as:

$$N_d = \dot{J}_\Omega(q_d)\ddot{q}_d + J_\Omega(q_d)\dddot{q}_d + \dot{M}_{e\Omega}(q_d) + \dot{M}_{g\Omega}(q_d) + \dot{M}_{v\Omega}(q_d) + \dot{\tau}_{d\Omega}(q_d, t) \tag{22}$$

where $M_{e\Omega} = \frac{M_e}{\Omega}$, $M_{g\Omega} = \frac{M_g}{\Omega}$, and $M_{v\Omega} = \frac{M_v}{\Omega}$.

The open-loop error system can then be expressed as:

$$J_\Omega \dot{r} = -\dot{V} - e_2 + \tilde{N} + N_d - \frac{1}{2} \dot{J}_\Omega r \tag{23}$$

where unmeasureable auxiliary term $\tilde{N}(t)$ is defined as $\tilde{N}(t) = N - N_d$. In some cases, it may be desirable to express the open-loop error system as in Equation 23 to segregate the uncertain nonlinearities and disturbances from the model into terms that are bounded by state-dependent bounds and terms that are upper bounded by constants. For example, in certain cases, the mean value theorem may be applied to upper bound unmeasureable auxiliary term $\tilde{N}(t)$ by state-dependent terms as:

$$\|\tilde{N}\| \leq \rho(\|z\|)\|z\| \tag{24}$$

where $z(t) \triangleq [e_1^T \ e_2^T \ r^T]^T$ and $\rho(\|z\|)$ is a positive, globally invertible, nondecreasing function. In some cases, the fact that $q_d(t)$, $g_d^i(t) \in L_\infty \forall i = 1, 2, 3, 4$ can be used to upper bound $N_d$ as:

$$\|N_d\| \leq \zeta_{N_d}, \|\dot{N}_d\| \leq \zeta_{\dot{N}_d} \tag{25}$$

where $\zeta_{N_d}$ and $\zeta_{\dot{N}_d}$ are known positive constants.

Based on the joint dynamics, the control input V(t) may be designed as:

$$V(t) \triangleq (k_s+1)e_2(t) - (k_s+1)e_2(0) + \int_0^t [(k_s+1)\alpha_2 e_2(\tau) + \beta \operatorname{sgn}(e_2(\tau))] d\tau \tag{26}$$

where $k_s$ and $\beta$ are positive constant adjustable control gains, and sgn denotes the signum function. In some cases, the time derivative of Equation 26 looks like a discontinuous sliding mode controller. Sliding mode control may be desirable because it is a method that can be used to reject the additive bounded disturbances present in the muscle dynamics (e.g., muscle spasticity, load changes, electromechanical delays) while still obtaining an asymptotic stability result. In some cases, the controller in Equation 26 can be implemented as a continuous controller (i.e., the unique integral of the sign of the error) while still yielding an asymptotic stability result. A controller using the input of Equation 26 may be referred to as a robust integral of the sign of the error (RISE) based controller. Equation 26 can ensure that all system signals are bounded under closed-loop operation. The position tracking error may be regulated in the sense that:

$$\|e_1(t)\| \to 0 \text{ as } t \to 0 \tag{27}$$

The controller may yield semi-global asymptotic tracking provided the control gain $K_s$ is selected sufficiently large and is selected according to the sufficient condition:

$$\beta > \left(\zeta_{N_d} + \frac{1}{\alpha_2} \zeta_{\dot{N}_d}\right) \tag{28}$$

The asymptotic stability can be seen in the following Lyapunov-based proof. In some cases, D is a domain in $R^{3+1}$ containing y(t)=0, where y(t) is defined as:

$$y(t) \triangleq [z^T \sqrt{P(t)}]^T \tag{29}$$

and auxiliary function P(t) is defined as:

$$P(t) \triangleq \beta \|e_2(0)\| - e_2(0)^T N_d(0) - \int_0^t L(\tau) d\tau \tag{30}$$

The auxiliary function L(t) can be defined as:

$$L(t) \triangleq r^T (N_d(t) - \beta \operatorname{sgn}(e_2)). \tag{31}$$

The derivative of P(t) can be expressed as:

$$\dot{P}(t) = -L(t) \triangleq r^T (N_d(t) - \beta \operatorname{sgn}(e_2). \tag{32}$$

The following inequality can then be obtained:

$$\int_0^t L(\tau) d\tau \leq \beta \|e_2(0)\| - e_2(0)^T N_d(0). \tag{33}$$

Equation 33 can be used to conclude that $P(t) \geq 0$.

In certain cases, $V_L(y,t)$ can be a continuously differentiable, positive definite function defined as:

$$V_L(y, t) \triangleq e_1^T e_1 + \frac{1}{2} e_2^T e_2 + \frac{1}{2} r^T J_\Omega r + P \tag{34}$$

that satisfies the inequalities:

$$U_1(y) \leq V_L(y,t) \leq U_2(y) \tag{35}$$

where $U_1$ and $U_2$ are continuous, positive definite functions.

The derivative of $V_L$ can be expressed as:

$$\dot{V}_L(y,t) = -(2\alpha_1-1)e_1^T e_1 + (\alpha_2-1)e_2^T e_2 - r^T r + r^T \tilde{N} - k_s r^T r. \quad (36)$$

The unique integral signum term in the RISE controller can be used to compensate for the disturbance terms included in $N_d$, provided the control gain $\beta$ is selected according to Equation 28. The term $r^T(t)\tilde{N}(e_1, e_2, r, t)$ can be upper bounded by:

$$\|r_N\| \le \rho(\|z\|)\|z\|\|r\| \quad (37)$$

to obtain:

$$\dot{V}_L(y,t) \le -\min\{2\alpha_1-1, \alpha_2-1, 1\}\|z\|^2 + [\rho(\|z\|)\|z\|\|r\| k_s \|r\|^2]. \quad (38)$$

Completing the squares for the bracketed terms yields:

$$\dot{V}_L(y,t) \le -\min\{2\alpha_1-1, \alpha_2-1, 1\}\|z\|^2 + \frac{\rho^2(\|z\|)\|z\|^2}{4k_s}. \quad (39)$$

The following expression can be obtained from Equation 39:

$$\dot{V}_L(y,t) \le -U(y) \quad (40)$$

where $U(y)$ is a continuous positive definite function, provided $k_s$ is selected sufficiently large based on the initial conditions of the system. The region of attraction can be made arbitrarily large to include any initial conditions by increasing the control gain $k_s$, (i.e., a semi-global type of stability result). Semi-global asymptotic tracking can therefore be achieved.

RISE+EMD Delay

In some embodiments, a controller may be configured to store a plurality of programs. A program may be selected and executed based on a determined user activity. In some embodiments a program may be selected based on direct user input. In other embodiments, the program may be selected based on sensing user behavior or from other context information. Some or all of the programs may implement an algorithm compensating for electromechanical delay (EMD) during neuromuscular electrical stimulation. EMD generally refers to a biological artifact that arises due to a time lag between application of electrical stimulation and tension development in a muscle, and it may cause degraded performance and instability during neuromuscular electrical stimulation. Without wishing to be bound by any particular theory, EMD may be caused at least in part by the finite propagation time of chemical ions in muscle, cross-bridge formation between actin-myosin filaments, stretching of the series elastic components in response to the external electrical input, and/or synaptic transmission delays. In some cases, EMD may vary with the input signal frequency.

In some cases, the algorithm may comprise a predictive term that actively accounts for EMD. In certain cases, filtered error signal $e_2(t)$ may be expressed as:

$$e_2 = \dot{e}_1 + \alpha e_1 - B\int_{t-t_\tau}^{t} V(\theta)d\theta \quad (41)$$

where $\alpha$ and $B$ are known control gain constants. Auxiliary function $\Omega$ may be defined as:

$$\Omega(q,t) = \zeta(q(t))\eta(t) \quad (42)$$

where $\zeta(q(t))$ represents a positive moment arm and $\eta(t)$ represents an unknown nonlinear function. The error $\xi$ between $B$ and $J_\Omega^{-1}$ may be defined by:

$$\xi = B - \frac{\Omega}{J} \quad (43)$$

where $\xi$ satisfies the relation $|\xi| \le \bar{\xi}$ and $\bar{\xi}$ is a known constant.

In some embodiments, the open-loop tracking error system may be developed by multiplying $J_\Omega$ by the time derivative of $e_2$ to obtain:

$$J_\Omega \dot{e}_2 = J_\Omega \ddot{q}_d + M_{e\Omega} + M_{g\Omega} + M_{v\Omega} + \tau_{d\Omega} + \alpha J_\Omega \dot{e}_1 - V - J_\Omega \xi[V - V_\tau] \quad (44)$$

where $M_{e\Omega} = \frac{M_e}{\Omega}$, $M_{g\Omega} = \frac{M_g}{\Omega}$, and $M_{v\Omega} = \frac{M_v}{\Omega}$.

In some such embodiments, auxiliary term $N_d$ can be defined as:

$$N_d = J_{\Omega d}\ddot{q}_d + M_{v\Omega d} + M_{g\Omega d} + M_{e\Omega d} \quad (45)$$

where the notation $J_{\Omega d}$, $M_{e\Omega d}$, $M_{g\Omega d}$, and $M_{v\Omega d}$ represent $J_\Omega$, $M_{e\Omega}$, $M_{g\Omega}$, and $M_{v\Omega}$ expressed in terms of desired limb position and velocity.

In some embodiments, control input $V(t)$ may be expressed as:

$$V = k_b e_2 \quad (46)$$

where $k_b$ is a known control gain that can be expanded as $k_b = k_{b_1} + k_{b_2} + k_{b_3}$, and $k_{b_1}$, $k_{b_2}$, and $k_{b_3}$ are known constants.

In certain cases, the closed-loop error system can be determined by adding and subtracting auxiliary term $N_d$ to $J_\Omega \dot{e}_2$ and using other relations to arrive at:

$$J_\Omega \dot{e}_2 = -\frac{1}{2}J_\Omega e_2 + \tilde{N} + S - e_1 - k_b e_2 - k_b J_\Omega \xi[e_2 - e_{2\tau}] \quad (47)$$

where the auxiliary terms $\tilde{N}$, $N$, and $S$ are defined as:

$$N = \frac{1}{2}J_\Omega e_2 + J_\Omega \ddot{q}_d + M_{e\Omega} + M_{g\Omega} + \\ M_{v\Omega} + \alpha J_\Omega e_2 - \alpha^2 J_\Omega e_1 + e_1 + \alpha J_\Omega B \int_{t-t_\tau}^{t} V(\theta)d\theta \quad (48)$$

$$\tilde{N} = N - N_d \quad (49)$$

$$S = N_d + d_\Omega \quad (50)$$

where $\tilde{N}$ can be upper bounded as:

$$\tilde{N} \le \rho(\|z\|)\|z\| \quad (51)$$

where $\rho(\|z\|)$ is a positive, globally invertible, nondecreasing function and $z$ is defined as $z = [e_1 \; e_2 \; e_z]^T$, where $e_z$ is defined as:

$$e_z = \int_{t-t_\tau}^{t} V(\theta)d\theta \quad (52)$$

S can be upper bounded as:

$$\|S\| \le \in \quad (53)$$

where $\in$ is a known constant.

Lyapunov-Karsovskii functionals $P$ and $Q$ can be defined as:

$$P = \omega \int_{t-t_\tau}^{t} \left(\int_{s}^{t} V(\theta)^2 d\theta\right) ds \quad (54)$$

$$Q = \frac{\bar{\xi} J^2 k_b}{2} \int_{t-t_\tau}^{t} e_2(\theta)^2 d\theta \quad (55)$$

where $\omega$ is a known constant.

The controller given in Equation 46 can ensure semi-global uniformly ultimately bounded tracking:

$$|e_1(t)| \le \epsilon_0 \exp(-\epsilon_1 t) + \epsilon_2 \quad (56)$$

where $\epsilon_0$, $\epsilon_1$, and $\epsilon_2$ are constants, provided control gains $\alpha$ and $k_b$ are selected according to sufficient conditions:

$$\alpha > \frac{B^2 \tau}{2\omega}, k_{b_3} > \frac{2\bar{\xi} J_2 (k_{b_1} + k_{b_2}) + \omega k_b^2 \tau}{1 - 2\bar{\xi} J_2} \quad (57)$$

The sufficient condition for $k_{b_3}$ can be satisfied by selecting $\omega$, $k_{b_1}$, and $k_{b_2}$ sufficiently small and $k_{b_3}$ sufficiently large, provided $1 - 2\bar{\xi} J_2 > 0$.

RISE+Neural Network

In some embodiments, the controller comprises a neural network (NN) based feed forward controller that is augmented with a continuous robust feedback term to yield an asymptotic result despite an uncertain, nonlinear muscle response. Such a controller may be implemented as part of a program or in any other suitable way. In some cases, it may be desirable to use NN-based controllers with an adaptive element that can adjust to unstructured, nonlinear disturbances in the muscle model. Use of NN-based controllers may, in some cases, reduce the tracking error for a given stimulation input. The ability of neural networks to learn uncertain and unknown muscle dynamics may be complemented by the ability of RISE to compensate for additive system disturbances and NN approximation error.

In some cases, the open-loop tracking error system may be developed by multiplying the expression for filtered tracking error r(t) in Equation 15 by $J/\Omega$ to obtain:

$$J_\Omega r = J_\Omega(\alpha_2 e_2 + \alpha_1 \dot{e}_1 + \ddot{q}_d) + M_e \Omega + M_g \Omega + M_v \Omega V + \tau_{d\Omega} \quad (58)$$

Equation 58 may be rewritten as:

$$J_\Omega r = f_d + S - V + \tau_{d\Omega} \quad (59)$$

where $f_d$ may be defined as:

$$f_d = M_{e\Omega d} + M_{g\Omega d} + M_{v\Omega d} + J_{\Omega d} \ddot{q}_d \quad (60)$$

and S may be defined as:

$$S = J_\Omega(\alpha_2 e_2 + \alpha_1 \dot{e}_1) + J_\Omega \ddot{q}_d - J_{\Omega d} \ddot{q}_d + M_e \Omega + M_g \Omega + M_v \Omega + (M_{e\Omega d} + M_{g\Omega d} + M_{v\Omega d}) \quad (61)$$

In some embodiments, S may be a compact, simply connected set of $R^4$, and C(S) may be defined as the space where $f_d$ is continuous. In some such embodiments, there exist weights and thresholds such that the function $f_d$ may be represented by a three-layer neural network as:

$$f_d = W^T \sigma(U^T x_d) + \epsilon(x_d) \quad (62)$$

where $x_d(t) = [1 \ q_d(t) \ \dot{q}_d(t) \ \ddot{q}_d(t)]^T$. $U \in R^{4_1}$ and $W \in R^{N_1+1}$ are bounded constant ideal weight matrices for the first-to-second and second-to-third layers, respectively, where $N_1$ is the number of neurons in the hidden layer. $\sigma$ is the sigmoid activation function $\sigma(\bullet)$: $R^4 \to R^{N_1+1}$ and $\epsilon(x_d)$ is the functional reconstruction error. In some cases, the additional term "1" in the input vector $x_d$ and activation term $\sigma$ may allow for thresholds to be included as the first columns of the weight matrices, such that any estimation of W and U includes estimation of the thresholds. In some cases, a three-layer NN approximation for $f_d$ may be given as:

$$\hat{f}_d = \hat{W}^T \sigma(\hat{U}^T x_d) \quad (63)$$

where $\hat{W}(t)$ and $\hat{U}(t)$ are estimates of the ideal weight matrices. The estimate mismatches may be defined as $\tilde{U} = U - \hat{U}$ and $\tilde{W} = W - \hat{W}$. The mismatch for the hidden-layer output error may be defined as:

$$\tilde{\sigma} = \sigma - \hat{\sigma} = \sigma(U^T x_d) - \sigma(\hat{U}^T x_d) \quad (64)$$

The ideal weights may be assumed to exist and to be bounded by positive values such that:

$$\|U\|_F^2 = tr(U^T U) = vec(U)^T vec(U) \le \overline{U}_B \quad (65)$$

$$\|W\|_F^2 = tr(W^T W) = vec(W)^T vec(W) \le \overline{W}_B \quad (66)$$

where $\|\bullet\|_F$ is the Frobenius norm of a matrix and $tr(\bullet)$ is the trace of a matrix.

Based on the assumption that the desired trajectory is bounded, the following inequalities may hold:

$$|\epsilon(x_d)| \le \epsilon_{b_1}, |\epsilon(\dot{x}_d)| \le \epsilon_{b_2}, |\epsilon(\ddot{x}_d)| \le \epsilon_{b_3} \quad (67)$$

where $\epsilon_{b_1}$, $\epsilon_{b_2}$, and $\epsilon_{b_3}$ are known positive constants.

In some embodiments, a closed-loop error system may be developed. In some cases, the NN structure may be developed in terms of the desired trajectories. This may be desirable, in certain cases, in order to avoid the use of acceleration measurements. In some cases, strategic separation and regrouping of terms may be needed to overcome the challenge that while the NN estimates may be upper bounded by constants, the time derivatives of the terms may be state-dependent.

In some cases, the control input may be:

$$V = \hat{f}_d + \mu \quad (68)$$

where $\mu$ is the RISE feedback term defined as:

$$\mu \triangleq (k_s + 1)e_2(t) - (k_s + 1)e_2(0) + v \quad (69)$$

where $k_s$ is a positive constant adjustable control gain and v(t) is the generalized solution to:

$$\dot{v} = (k_s + 1)\alpha_2 e_2(t) + \beta_1 \text{sgn}(e_2(t)), v(0) = 0 \quad (70)$$

where $\beta_1$ is a positive constant adjustable control gain. The estimates for the NN weights may be generated using a projection algorithm as:

$$\dot{\hat{W}} = \text{proj}(\Gamma_1 \hat{\sigma}' \hat{U}^T \dot{x}_d e_2^T) \quad (71)$$

$$\dot{\hat{U}} = \text{proj}(\Gamma_2 \dot{x}_d (\hat{\sigma}'^T \hat{W} e_2)^T) \quad (72)$$

where $\Gamma_1$ and $\Gamma_2$ are constant, positive definite, symmetric gain matrices. It should be noted that the expressions for estimated NN weights may vary depending on the desired tasks and other characteristics of the controller.

The NN-based feedforward component $\hat{f}_d$ may be used to approximate the desired musculoskeletal dynamics $f_d$. The NN component may approximate the desired function through adaptive weight estimates that are adjusted online via the adaptive law given in Equation 72. In some cases, the RISE feedback controller $\mu(t)$ has implicit learning characteristics that maintain the robustness of the system in the presence of additive disturbances and residual function approximation error. One role of the RISE feedback controller may be to keep the system stable while the NN approximates the system dynamics.

The closed-loop tracking error system may be developed by substituting Equation 68 into Equation 59 as:

$$J_\Omega r = \tilde{f}_d + S - \mu + \tau_{d\Omega} \quad (73)$$

where $\tilde{f}_d = f_d - \hat{f}_d$.

To facilitate subsequent closed-loop stability analysis, the time derivative of Equation 73 may be determined as:

$$J_\Omega \dot{r} = -\dot{J}_\Omega r + \dot{\tilde{f}}_d + \dot{S} - \dot{\mu} + \dot{\tau}_{d\Omega} \quad (74)$$

Although the control input V(t) is present in the open-loop error system, an additional derivative may be taken to facilitate the design of the RISE-based feedback controller. The closed-loop system may be expressed as:

$$J_\Omega \dot{r} = -J_\Omega r + W^T \sigma'(U^T x_d)U^T \dot{x}_d - \hat{W}^T \sigma(\hat{U}^T x_d) - \hat{W}^T \sigma'(\hat{U}^T x_d)\hat{U}^T \dot{x}_d - \hat{W}^T \sigma'(\hat{U}^T x_d)\dot{\hat{U}}^T x_d + \epsilon(x_d) + \dot{S} - \dot{\mu} + \dot{\tau}_{d\Omega} \quad (75)$$

$$\text{where } \sigma'(\hat{U}^T x_d) = \frac{d\sigma(U^T x_d)}{d(U^T x_d)} \bigg|_{U^T x_d = \hat{U}^T x_d}.$$

The following expression may then be obtained:

$$J_\Omega \dot{r} = -J_\Omega r + \hat{W}^T \hat{\sigma}' \tilde{U}^T \dot{x}_d - \tilde{W}^T \hat{\sigma}' \hat{U}^T \dot{x}_d - \hat{W}^T \hat{\sigma}' \tilde{U}^T \dot{x}_d - \hat{W}^T \hat{\sigma}' \hat{U}^T \dot{x}_d + W^T \sigma' U^T \dot{x}_d + \epsilon(x_d) - \hat{W}^T \hat{\sigma}' \dot{\hat{U}}^T x_d - \dot{\hat{W}}^T \hat{\sigma} + \dot{S} - \dot{\mu} + \dot{\tau}_{d\Omega} \quad (76)$$

Using the NN weight tuning laws, the expression may be rewritten as:

$$J_\Omega \dot{r} = -\frac{1}{2} \dot{J}_\Omega r + \tilde{N} + N - e_2 - (k_s + 1)r - \beta \text{sgn}(e_2) \quad (77)$$

where unmeasureable auxiliary term $\tilde{N}$ may be defined as:

$$\tilde{N} = -\frac{1}{2} \dot{J}_\Omega r + \dot{S} + e_2 - \text{proj}(\Gamma_1 \hat{\sigma}' \hat{U}^T x_d e_2^T)^T \hat{\sigma} - \hat{W}^T \hat{\sigma}' \text{proj}(\Gamma_2 x_d (\hat{\sigma}'^T \hat{W} e_2)^T)^T x_d \quad (78)$$

and unmeasureable auxiliary term N may be defined as:

$$N = N_B + N_d \quad (79)$$

$N_d$ may be defined as:

$$N_d = W^T \sigma' U^T \dot{x}_d + \epsilon(x_d) + \tau_{d\Omega} \quad (80)$$

and $N_B$ may be defined as:

$$N_B = N_{B_1} + N_{B_2} \quad (81)$$

where $N_{B_1}$ and $N_{B_2}$ may be given by:

$$N_{B_1} = -\hat{W}^T \sigma' \tilde{U}^T \dot{x}_d - \tilde{W}^T \hat{\sigma}' \hat{U}^T \dot{x}_d \quad (82)$$

$$N_{B_2} = \hat{W}^T \hat{\sigma}' \tilde{U}^T \dot{x}_d + \tilde{W}^T \hat{\sigma}' \hat{U}^T \dot{x}_d \quad (83)$$

In some cases, it may be desirable to define the terms in such a way in order to segregate terms that are bounded by state-dependent bounds and terms that are upper bounded by constants for the development of the NN weight update laws and the subsequent stability analysis. The auxiliary term $N_B$ may be further segregated to develop gain conditions in the stability analysis. The mean value theorem may be applied to upper bound $\tilde{N}$ as:

$$|\tilde{N}| \le \rho(\|z\|)\|z\| \quad (84)$$

where $z \triangleq [e_1 \ e_2 \ r]^T$ and the bounding function $\rho(\|z\|)$ is a positive, globally invertible, nondecreasing function. The following inequalities may be developed:

$$|N_d| \le \zeta_1, |N_B| \le \zeta_2, |\dot{N}_d| \le \zeta_3, \text{ and } |\dot{N}_B| \le \zeta_4 + \zeta_5 |e_2| \quad (85)$$

where for $\zeta_i = 1, 2, \ldots 5$ are positive known constants.

The composite NN and RISE controller can ensure that all system signals are bounded under closed-loop operation and that the position tracking error is regulated in the sense that:

$$|e_1(t)| \to 0 \text{ as } t \to \infty \quad (86)$$

provided the control gains are selected according to the following sufficient conditions:

$$\alpha_1 > \frac{1}{2}, \quad \alpha_2 > \beta_2 + 1 \quad (87)$$

$$\beta_1 > \zeta_1 + \zeta_2 + \frac{1}{\alpha_2} \zeta_3 + \frac{1}{\alpha_2} \zeta_4, \quad \beta_2 > \zeta_5$$

and control gain $k_s$, is selected sufficiently large based on the initial conditions of the error system.

Asynchronous Stimulation

NMES can sometimes lead to early onset of muscle fatigue during stimulation, limiting the duration that functional tasks can be performed in assistive devices. In some embodiments, a controller may apply asynchronous stimulation, which may reduce NMES-induced fatigue. Asynchronous stimulation generally refers to use of multiple stimulation channels and electrodes to target different muscles or different groups of motor units within a given muscle. Without wishing to be bound by a particular theory, asynchronous stimulation may lead to lower rates of fatigue due to reduced duty cycle (i.e., a lower average stimulation frequency) for the recruited motor units compared to conventional stimulation.

In some cases, switching between different muscles may introduce discontinuities in the open-loop dynamics. These discontinuities may be a consequence of the fact that the response to a given stimulus will differ for each subsystem (i.e., each subsystem activates a different number and/or type of muscle fibers). In certain embodiments, pulses may be delivered in an interleaved fashion to each stimulation channel. Utilizing interleaved pulses rather than sequentially delivering pulse trains may be advantageous, in some cases, at least in part because interleaving the pulses across the stimulation channels may provide an averaging effect due to the temporal summation of the force. The extent of the averaging effect may depend upon the stimulation frequency; higher stimulation frequencies may smooth the force output, but a primary motivation for utilizing interleaved pulses is to achieve decreased rates of fatigue through the use of low frequency stimulation.

As suggested by Equation 9 above, the joint dynamics during stimulation of two subsystems may be modeled as:

$$M_I + M_e + M_g + M_v + \tau_d = \tau_i + \tau_j \quad (88)$$

$\tau_i$ and $\tau_j$ represent the torque produced by stimulation of the $i^{th}$ and $j^{th}$ subsystems, and the inertial, gravitational, elastic, and viscous components are common to all subsystems since all subsystems act on the same joint. The unknown bounded disturbance torque $\tau_d$ may also be modeled as being common to all subsystems.

In some cases, the open-loop dynamics for asynchronous stimulation may be obtained as:

$$J\dot{r} = W - \tau_i - \tau_j + \tau_d, i \ne j \quad (89)$$

where J is the same inertia for each subsystem since each subsystem acts on the same joint complex. $W(\dot{e}_1, e_2, t)$ denotes an auxiliary term defined as in Equation 17. The open-loop dynamics may be expressed as:

$$J\dot{r} = W - V_i \Omega_i - V_j \Omega_j + \tau_d \quad (90)$$

where $V_i$ denotes the stimulation applied to the $i^{th}$ subsystem by electrical stimulation, and $\Omega_i$ is a positive auxiliary term that relates the stimulation applied to the $i^{th}$ subsystem to the torque produced by the $i^{th}$ subsystem, defined as:

$$\Omega_i \triangleq \zeta_i \eta_i \cos a_i(q) \quad (91)$$

The first time derivative of $\Omega_i$ is continuous and bounded, and the second time derivative of $\Omega_i$ is bounded. In some cases, $\sigma$ may denote a piecewise constant signal that selects the subsystem to be activated at time t. The instances when the value of $\sigma$ changes are called the switching times, $t_i$. Immediately following each switching time, there may be a transition period $\Delta t$ during which the input is transitioned from one subsystem to another. To facilitate the subsequent analysis, the closed-loop dynamics of the switched system and the Lyapunov candidate function may be made continuous through the signal X(t), where X is designed such that the transition period from one subsystem to another results in a continuous torque output due to stimulation. X denotes the percentage of the input delivered to one of the two selected subsystems, and the remaining percentage of the input (1–X), is delivered to the other subsystem. V(t) can denote the input to the system such that $V=V_i+V_j$, where $$V_i=XV, V_j=(1-X)V. \tag{92}$$

The closed loop dynamics may be expressed as:

$$Jr=W-V\Omega_1+\tau_d, t_0 \le t < t_1$$

$$Jr=W-XV\Omega_1-(1|X)V-\Omega_2+\tau_d, t_1 \le t < t_2$$

$$Jr=W-XV\Omega_3(1-X)V\Omega_2+\tau_d, t_2 \le t < t_3$$

$$Jr=W-XV\Omega_3-(1-X)V\Omega_4+\tau_d, t_3 < t < t_4 \tag{93}$$

In some cases, an example definition of X may be given by:

$$X \triangleq \begin{cases} \dfrac{1-\sin(\alpha(t-t_{2k-1})-\frac{\pi}{2})}{2}, & t \in [t_{2k-1}, t_{2k-1}+\Delta t] \\ 0, & t \in [t_{2k-1}, +\Delta t, t_{2k}) \\ \dfrac{1+\sin(\alpha(t-t_{2k-1})-\frac{\pi}{2})}{2}, & t \in [t_{2k}, t_{2k}+\Delta t] \\ 1, & t \in [t_0, t_1) \cup [t_{2k}+\Delta t, t_{2k+1}) \end{cases} \tag{94}$$

where X and its first time derivative are bounded and continuous and the second time derivative is bounded. The transition period in Equation 94 is defined as $$\Delta t \triangleq \frac{\pi}{a}$$

arbitrarily short through the choice of a.

In some cases, it may be desirable to obtain the time derivative of Equation 93 to facilitate stability analysis. The time derivative may be expressed as:

$$J\dot{r} = -\frac{1}{2}Jr + \tilde{N} + N_{d1} - e_2 + \tag{95}$$
$$[XN_{d2,i} + (1-X)N_{d2,j}] - [X\Omega_i + (1-X)\Omega_j]\dot{V} +$$
$$[\dot{X}N_{d3,i} - \dot{X}N_{d3,j}]V$$

where the following auxiliary terms may be defined as:

$$N \triangleq \dot{W} + e_2 - \frac{1}{2}\dot{J}r + \dot{\tau}_d \tag{96}$$

-continued $$N_{di} \triangleq J\ddot{q}_d + \dot{J}\dot{q}_d + \dot{M}_e + \dot{M}_g + \dot{M}_v + \dot{\tau}_d \tag{97}$$

$$N_{d2,i} \triangleq -\dot{\Omega}_i V \tag{98}$$

$$N_{d3,i} \triangleq -\Omega_i \tag{99}$$

$$\tilde{N} \triangleq N - N_{d1}. \tag{100}$$

In some cases, it may be desirable to express the open-loop error system as in Equation 95 to separate the model into groups that are bounded by state-dependent bounds or by constants. By applying the Mean Value Theorem, Kr may be upper bounded by state-dependent terms as:

$$|\tilde{N}| \le \rho(\|z\|)\|z\| \tag{101}$$

where $z(t) \triangleq [e_1^T\ e_2^T\ r^T]^T$ and $\rho(\|z\|)$ is a positive, globally invertible, nondecreasing function. The desired trajectory may be used to prove the upper bounds:

$$|N_{d1}| \le \zeta_{N_{d1}} \tag{102}$$

$$|\dot{N}_{d1}| \le \zeta_{\dot{N}_{d1}} \tag{103}$$

$$|N_{d2,i}| \le \rho_{N_{d2,i}}(\|z\|)|V(t)| \tag{104}$$

$$|\dot{N}_{d2,i}| \le \rho_{1,\dot{N}_{d2,i}}(\|z\|)|V(t)| + \rho_{2,\dot{N}_{d2,i}}(\|z\|) \tag{105}$$

$$|N_{d3,i}| \le \rho_{N_{d3,i}}(\|z\|) \tag{106}$$

$$|\dot{N}_{d3,i}| \le \rho_{\dot{N}_{d3,i}}(\|z\|) \tag{107}$$

where $\zeta_{N_{d1}}$ and $\zeta_{\dot{N}_{d1}}$ are known positive constants and $\rho_{N_{d2,i}}(\|z\|)$, $\rho_{1,\dot{N}_{d2,i}}(\|z\|)$, $\rho_{2,\dot{N}_{d2,i}}(\|z\|)$, $\rho_{N_{d3,i}}(\|z\|)$, and $\rho_{\dot{N}_{d3,i}}(\|z\|)$ are positive, globally invertible, nondecreasing functions.

To facilitate stability analysis, Equation 95 may be expressed as:

$$J\dot{r} = -\frac{1}{2}Jr + \tilde{N} + N_{d1} - e_2 + \overline{N}_{d2} - \overline{\Omega}\dot{V} + \dot{X}\overline{N}_{d3}V \tag{108}$$

where $\overline{N}_{d2}$, $\overline{\Omega}$, and $\overline{N}_{d3}$ are continuous functions defined as:

$$\overline{N}_{d2} \triangleq [XN_{d2,i} + (1-X)N_{d2,j}] \tag{109}$$

$$\overline{N}_{d3} \triangleq [N_{d3,i} - N_{d3,j}] \tag{110}$$

$$\overline{\Omega} \triangleq [X\Omega_i + (1-X)\Omega_j] \tag{111}$$

The auxiliary terms may be bounded as:

$$|\overline{N}_{d2}| \le \rho_{\overline{N}_{d2}}(\|z\|)|V(t)| \tag{112}$$

$$|\dot{\overline{N}}_{d2}| \le \rho_{1,\overline{N}_{d2}}(\|z\|)|V(t)| + \rho_{2,\overline{N}_{d2}}(\|z\|) \tag{113}$$

$$|N_{d3}| \le \rho_{\overline{N}_{d3}}(\|z\|)|V(t)| \tag{114}$$

$$|\dot{\overline{N}}_{d3}| \le \rho_{\overline{N}_{d3}}(\|z\|) \tag{115}$$

$$|\overline{\Omega}| \le \rho_{\overline{\Omega}}(\|z\|) \tag{116}$$

$$|\dot{\overline{\Omega}}| \le \rho_{\overline{\Omega}}(\|z\|) \tag{117}$$

The RISE-based voltage controller may be designed as:

$$V(t) \triangleq \frac{1}{\epsilon}(k_s + 1)(e_2(t) - e_2(0)) + v(t) \tag{118}$$

where v(t) is the generalized Fillipov solution to $$\dot{v}(t) = \frac{1}{\epsilon}(k_s + 1)\alpha_2 e_2(t) + (\beta + \beta_V |V| \text{sgn}(e_2(t))) \quad (119)$$

where $\alpha_2$, $k_s$, $\beta$, $\beta_T$ are positive, constant control gains.

In some cases, the designed switching signal σ may have a finite number of discontinuities on any bounded time interval. Any two consecutive switching times, $t_i$ and $t_{i+1}$ may satisfy $t_i + \Delta t < t_{i+1}$, and the switching signal may remain constant for $t \in [t_i, t_{i+1})$.

The controller designed in Equation 108 may yield semi-global asymptotic tracking in the sense that $|e_1(t)| \to 0$ as $t \to \infty$ under any switching signal satisfying the condition above, provided that the control gains $\alpha_1$, $\alpha_2$, $k_s$, $\beta$, $\beta_V$ are selected according to the sufficient conditions:

$$\alpha_1 > \frac{1}{2}, \quad k_s > \frac{\rho^2 \|y(0)\|}{4\lambda} \quad (120)$$

$$\beta_v > \max_{i \in S} \left\{ \frac{1}{\epsilon} \left[ \rho_{N_{d2,i}} + \left(\frac{\alpha}{2}\right) \rho_{N_{d3,i}} + 1 \right] \Big|_{\|z\| = \|y(0)\|} \right\} \quad (121)$$

$$\beta > \frac{1}{\epsilon} [\zeta_{N_{d1}} + 1] \quad (122)$$

$$\alpha_2 > \max \left\{ \left[ \rho_{1, \dot{N}_{d2}} + \rho_{2, \ddot{N}_{d2}} \beta_V + \rho_{\tilde{\Omega}} \beta_V^2 + \rho_{\tilde{\Omega}} \beta_V + \right. \right. \quad (123)$$
$$\left( \frac{\alpha}{2} \right) \rho_{\bar{N}_{d3}} [1 + \alpha + \beta_V] + \left( \frac{\alpha}{2} \right) \rho_{\dot{N}_{d3}} \Big] \Big|_{\|z\| = \|y(0)\|},$$
$$\left[ \zeta_{\bar{N}_{d1}} + \left( \rho_{\dot{\Omega}} + \rho_{2, \ddot{N}_{d2}} + \rho_{\tilde{\Omega}} \beta_V + \left( \frac{\alpha}{2} \right) \rho_{\bar{N}_{d3}} \right) \beta + \right.$$
$$\left. \frac{1}{\epsilon} (k_s + 1) \|y(0)\| \left( \rho_{2, \ddot{N}_{d2}} + \rho_{\tilde{\Omega}} \beta_V + \left( \frac{\alpha}{2} \right) \rho_{\bar{N}_{d3}} \right) \right] \Big|_{\|z\| = \|y(0)\|}, 2 \right\}$$

where $\lambda \triangleq \min\{2\alpha_1 - 1, \alpha_2 - 1, 1\}$.

In some embodiments, the neural network may be used to estimate acceleration of a limb. A controller using such a neural network can achieve a controller using only position and velocity information.

Example 1

This Example describes the use of functional electrical stimulation (FES) to activate lower limb muscles to pedal a cycling device (e.g., a stationary bicycle, a mobile bicycle, a mobile tricycle). FES-induced cycling could, for example, be used as a means of exercise and/or rehabilitation for individuals with dysfunctional lower limb muscles (e.g., individuals with neuromuscular disorders). In some embodiments, control as described in this example may be implemented in a hybrid orthotic device as described herein. However, it should be appreciated that the device providing functional electrical stimulation may be packaged in any suitable way, including using a controller in an exercise bicycle to compute functional electrical stimulation. Such a device may include sensors to provide measured values of control inputs to the controller. For example a sensor, or sensors, may provide measurements of position, velocity and/or other parameters of motion of a crank of an exercise device.

Previous FES-induced cycling efforts described in the literature found that FES-induced cycling was metabolically inefficient and yielded low power output at the cycle crank compared to able-bodied cycling. In this Example, to improve muscle control and thereby improve efficiency and increase power output, a stimulation pattern for quadriceps femoris-only FES-induced cycling was derived based on the kinematic effectiveness of knee joint torque in producing forward pedaling throughout the crank cycle. The stimulation pattern was designed such that stimulation was not applied in regions near the dead points of the cycle in order to bound the stimulation voltage, while everywhere else in the crank cycle either the right or left quadriceps were stimulated to produce forward pedaling. This led to partitioning of the crank cycle into controlled and uncontrolled regions. Stimulation of additional muscle groups (e.g., the gluteal muscles) could have eliminated uncontrolled regions, but also could have resulted in overlapping controlled regions and over-actuation. Therefore, the stimulation pattern only stimulated the quadriceps.

In some embodiments, control was switched such that only one leg was stimulated at one time. Accordingly, in this Example, in the controlled regions, a switched sliding mode controller was designed that guaranteed exponentially stable tracking of a desired crank trajectory, provided certain gains conditions were satisfied. In the uncontrolled regions, the tracking error proved to be ultimately bounded, provided a reverse dwell-time condition, which required that the system not dwell in the uncontrolled region for an overly long time interval, was satisfied. The reverse dwell-time condition was shown to be satisfied provided sufficient desired cadence conditions were satisfied. Stability was derived through Lyapunov methods for switched systems. Experimental results demonstrated the performance of the switched control system under typical cycling conditions.

I. Model

A. Cycling Device and Rider Dynamic Model

Figure 7:
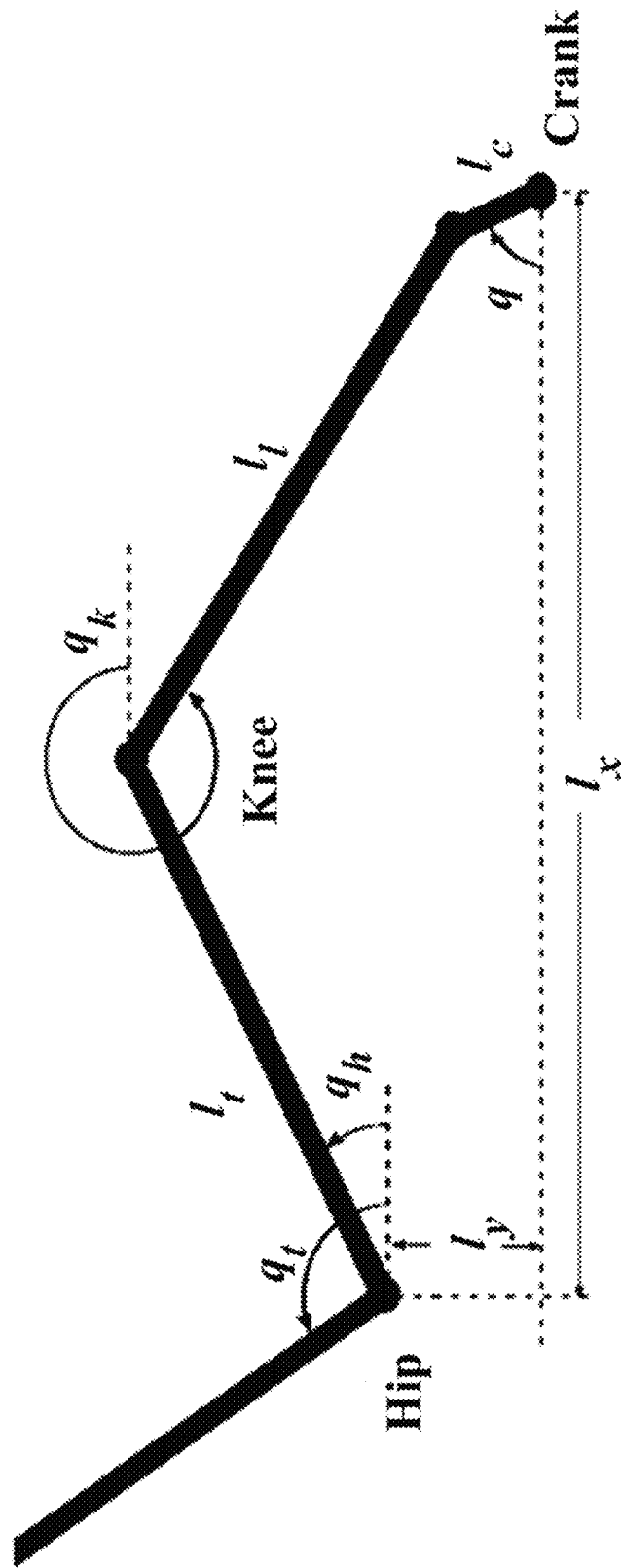
FIG. 7 shows an exemplary schematic illustration of a system comprising a rider and a cycle, according to some embodiments.

A cycling device (e.g., comprising a seat, a crank, and two pedals) and a two-legged rider were modeled as a single degree-of-freedom system, which was expressed as:

$$M\ddot{q} + V\dot{q} + G + \tau_d = \tau_{crank} \quad (124)$$

where $q \in Q \subset \mathbb{R}$ denoted the crank angle (e.g., the clockwise angle between the ground and the right crank arm), $M \in \mathbb{R}$ denoted inertial effects, $V \in \mathbb{R}$ represented centripetal and Coriolis effects, $G \in \mathbb{R}$ represented gravitational effects, $\tau_d \in \mathbb{R}$ represented an unknown, time-varying, bounded disturbance (e.g., spasticity and/or changes in load), and $\tau_{crank} \in \mathbb{R}$ represented the torque applied about the crank axis. The rider's legs were modeled as planar rigid-body segments with revolute hip and knee joints. More complex models of the knee joint had been found to have a negligible effect on the linkage kinematics. The ankle joint was assumed to be fixed in accordance with common clinical cycling practices for safety and stability. When the rider's feet were fixed to the pedals of the cycle, the resulting system could be completely described by the crank angle (or any other single joint angle measured with respect to ground) and the kinematic parameters of the limb segments. FIG. 7 depicts one side of the cycle-rider system described by Equation 124. As shown in FIG. 7, $q_t \in \mathbb{R}$ was the measurable constant trunk angle, $q_h \in \mathbb{R}$ was the hip angle, $q_k \in \mathbb{R}$ was the knee angle, $l_x \in \mathbb{R}_{\geq 0}$ was the measureable constant horizontal distance between the hip and crank joint axes, $l_y \in \mathbb{R}_{\geq 0}$ was the measureable constant vertical distance between the hip and crank joint axes, $l_t \in \mathbb{R}_{>0}$ was the measureable constant thigh segment length, $l_l \in \mathbb{R}_{>0}$ was the measureable constant shank segment length, and $l_c \in \mathbb{R}_{>0}$ was the measureable constant crank segment length. The trunk, hip, and knee angles were geometric functions of $l_x$, $l_y$, $l_t$, and/or $l_c$.

The crank torque was composed of local torques (e.g., friction in the crank bearings) and torques from other joints that were translated to the crank axis (e.g., torques produced by the rider's muscles and/or ligaments). Taking into account, inter alia, viscous damping in the crank joint, passive hip and knee joint torques, and active torque produced at the knees by the quadriceps femoris muscle groups, the crank torque was expressed as:

$$\tau_{crank} = \tau_b + \sum_{j \in \mathcal{J}} \sum_{s \in \mathcal{S}} B_j^s \tau_j^s \qquad (125)$$

where $\tau_b \triangleq -c\dot{q}$, with $c \in \mathbb{R}_{>0}$ as the unknown constant damping coefficient, $B_j^s \in \mathbb{R}$ was the Jacobian element relating torque from a given joint to the crank torque, and $\tau_j^s \in \mathbb{R}$ was the net torque at a joint. The joint set was defined as $\mathcal{J} \triangleq \{h,k\}$, where h and k indicated the hip and knee joints, respectively. The set $\mathcal{S} \triangleq \{R,L\}$ denoted the right leg (indicated by R) or left leg (indicated by L). For simplicity of notation, the superscript s indicating leg side was generally omitted unless it added clarity. The elements $B_j$, which were joint torque transfer ratios, were defined as:

$$B_h \triangleq -\frac{\partial q_h}{\partial q}, \quad B_k \triangleq \frac{\partial q_h}{\partial q} - \frac{\partial q_k}{\partial q} \qquad (126)$$

Each joint torque $\tau_j$ could be decomposed into active (i.e., from active muscle contractions) and passive (i.e., from viscoelastic tissue properties) torque as:

$$\tau_j = \tau_{j,a} + \tau_{j,p} \qquad (127)$$

where the subscript a indicated active torque and the subscript p indicated passive torque. Taking only active contractions of the quadriceps femoris muscle groups into account (e.g., neglecting the biarticular effects of the rectus femoris), the following expression for net active joint torque was obtained:

$$\sum_{j \in \mathcal{J}} \sum_{s \in \mathcal{S}} \tau_{j,a}^s = \sum_{s \in \mathcal{S}} \tau_{quad}^s \qquad (128)$$

where $\tau_{quad} \in \mathbb{R}$ was defined as the active torque produced by the quadriceps muscle group about the knee joint. $\tau_{quad}$ could be expressed as:

$$\tau_{quad} = \Omega u \qquad (129)$$

where $u \in \mathbb{R}$ was a control input (e.g., a voltage applied across the quadriceps muscle group) and $\Omega \in \mathbb{R}$ was defined as:

$$\Omega \triangleq \lambda \eta \cos(a) \qquad (130)$$

where $\lambda \in \mathbb{R}_{>0}$, was an uncertain moment arm of the quadriceps muscle force about the knee, $\eta \in \mathbb{R}$ was an uncertain nonlinear function relating stimulation voltage to muscle fiber force, and $a \in \mathbb{R}$ was an uncertain pennation angle of the quadriceps muscle fibers.

The passive viscoelastic effects in the hip and knee joints were modeled as:

$$\tau_{j,p} = k_{j,1} e^{-k_{j,2} \gamma_j} (\gamma_j - k_{j,3}) + b_{j,1} \tan h(-b_{j,2}\dot{\gamma}_j) - b_{j,3}\dot{\gamma}_j j \in \mathcal{J} \qquad (131)$$

where $k_{j,i}$, $b_{j,i} \in \mathbb{R}_{>0}$, $i \in \{1, 2, 3\}$ were unknown constant coefficients, and $\gamma_i \in \mathbb{R}$ were the relative hip and knee joint angles defined as:

$$\gamma_h \triangleq q_h - q_t \qquad (132)$$

$$\gamma_k \triangleq q_k - q_h + \pi \qquad (133)$$

Substituting Equations 127-129 into Equation 125 yielded:

$$\tau_{crank} = \tau_b + P + \sum_{s \in \mathcal{S}} B_k^s \Omega^s u^s \qquad (134)$$

where the auxiliary term $P \in \mathbb{R}$ captured the passive joint torque effects on the crank and was defined as:

$$P \triangleq \sum_{j \in \mathcal{J}} \sum_{s \in \mathcal{S}} B_j^s \tau_{j,p}^s \qquad (135)$$

The equation of motion for the total cycle-rider system with electrical stimulation of the quadriceps muscles was obtained by substituting Equation 134 into Equation 124 as:

$$M\ddot{q} + V\dot{q} + G + \tau_d - \tau_b - P = \sum_{s \in \mathcal{S}} B_k^s \Omega^s u^s \qquad (136)$$

The model in Equation 136 had the following properties:
Property 1. $c_m \leq M \leq c_M$, where $c_m, c_M \in \mathbb{R}_{>0}$, were known constants.
Property 2. $|V| \leq c_v |\dot{q}|$, where $c_v \in \mathbb{R}_{>0}$, was a known constant.
Property 3. $|G| \leq c_G$, where $c_G \in \mathbb{R}_{>0}$, was a known constant.
Property 4. $|\tau_d| \leq c_d$, where $c_d \in \mathbb{R}_{>0}$, was a known constant.
Property 5. $|B_j^s| \leq c_B \forall s \in \mathcal{S}$, $j \in \mathcal{J}$, where $C_B \in \mathbb{R}_{>0}$ was a known constant.
Property 6. $|P| \leq c_{p1} + c_{p2}|\dot{q}|$, where $c_{p1}, c_{p2} \in \mathbb{R}_{>0}$ were known constants.
Property 7. $c_{\Omega n} \leq \Omega^s \leq c_{\Omega 2} \cdot s \in \mathcal{S}$, where $c_{\Omega 1}, c_{\Omega 2} \in \mathcal{S}_{>0}$ were known constants.
Property 8.

$$\frac{1}{2}\dot{M} - V = 0$$

B. Switched System Model

The torque transfer ratios $B_k^s$, provided insight into how the quadriceps muscles of each leg should be activated during the crank cycle. As shown in FIG. 7, the quadriceps produced a counter-clockwise torque about the knee joint that acted to extend the knee. Multiplication of the active knee torque by $B_k$ transformed the counter-clockwise torque produced by the quadriceps to a resultant torque about the crank. Therefore, as forward pedaling required a clockwise torque about the crank, the quadriceps muscles should only be activated when they produced a clockwise torque about the crank (e.g., when $B_k$ was negative). The torque transfer ratio $B_k$ was negative definite for half of the crank cycle, and the sign of the torque transfer ratio of one leg was generally opposite from the other leg (e.g., $B_k^R B_k^L \leq 0 \ \forall q$), provided the crank arms were offset by $\pi$ radians. To pedal using only the quadriceps muscles, the controller alternated between legs, using the right quadriceps when $B_k^R < 0$ and the left quadriceps when $B_k^L<0$. The controller switched between legs when $B_k=0$, which occurred at the so-called "dead points" $q^* \in Q^* \subset Q$, where $$Q^* \triangleq \left\{ q \in Q \mid q = \arctan\left(\frac{l_y}{l_x}\right) + n\pi \right\}, n \in \mathbb{Z}.$$

Since the torque transfer ratios were minimal near the dead points, stimulation applied close to the dead points was inefficient in the sense that large knee torques generally yielded small crank torques. Therefore, the uncontrolled region, in which no stimulation was applied, was defined as $Q_u \triangleq \{q \in Q \mid -B_K^s(q) \le \varepsilon\} \mathbb{I} Q$, where $\varepsilon \in \mathbb{R}_{>0}$ was a scalable constant that could be increased to reduce the portion of the cycle trajectory where stimulation was applied. Specifically, $\varepsilon < \max(-B_k^s)$. Also, the sets $Q^s \subset Q$ were defined as the regions where the right and left quadriceps muscle groups were stimulated, as $$Q^s \triangleq \{q \in Q \mid -B_k^s(q) > \varepsilon\} \quad (137)$$

The set $Q_c \triangleq \cup_{s \in \delta} Q^s$ was denoted as the controlled region, where $Q_c \cup Q_u = Q$ and $Q^R \cap Q^L = \emptyset$ (e.g., stimulation voltage was generally not applied to both legs at the same time). The static stimulation pattern was then completely defined by the cycle-rider kinematics (e.g., $B_k$) and selection of $\varepsilon$. Smaller values of $\varepsilon$ yielded larger stimulation regions, while larger values of $\varepsilon$ yielded smaller stimulation regions. It had been suggested that the stimulation region should be made as small as possible while maximizing stimulation intensity to optimize metabolic efficiency, motivating the selection of large values of $\varepsilon$.

Cycling was achieved by switching between the left and right limbs, where stimulation of the quadriceps occurred outside of $Q_u$ to avoid the dead points and their neighborhoods, where pedaling was inefficient. Specifically, the switched control input $u^s$ was designed as $$u^s \triangleq \begin{cases} v^s & \text{if } q \in Q_c \\ 0 & \text{if } q \in Q_u \end{cases} \quad (138)$$

where $v^s \in \mathbb{R}$ was the stimulation (e.g., voltage) applied across the quadriceps muscle group. Substitution of Equation 138 into Equation 136 yielded a switched system with autonomous state-dependent switching:

$$M\ddot{q} + V\dot{q} + G + \tau_d - \tau_b - P = \begin{cases} B_k^s \Omega^s v^s & \text{if } q \in Q_c \\ 0 & \text{if } q \in Q_u \end{cases} \quad (139)$$

Figure 8:
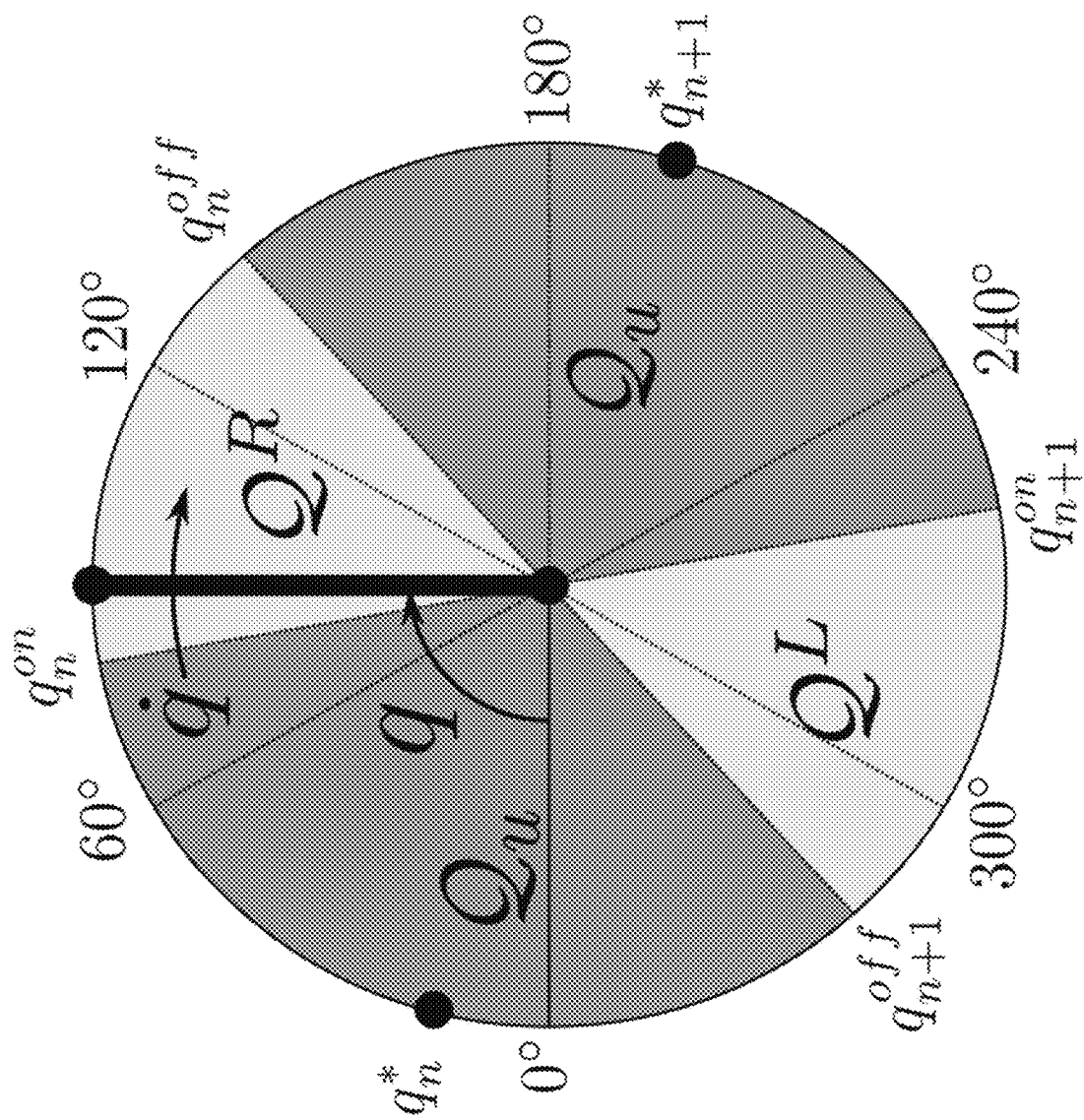
FIG. 8 shows, according to some embodiments, an exemplary schematic illustration of controlled and uncontrolled regions throughout a crank cycle.

Assuming that q started within controlled region $Q_c$, the known sequence of switching states was defined as $\{q_n^{on}, q_n^{off}\}$, $n \in \{0, 1, 2, \ldots\}$, where $q_0^{on}$ was the initial crank angle and the switching states which followed were precisely the limit points of $Q_u$. The corresponding sequence of switching times $\{t_n^{on}, t_n^{off}\}$, which were unknown a priori, were defined such that each on-time $t_n^{on}$ and off-time $t_n^{off}$ occurred when q reached the corresponding on-angle $q_n^{on}$ and off-angle $q_n^{off}$, respectively. An exemplary schematic illustration of controlled and uncontrolled regions throughout a crank cycle is shown in FIG. 8. The controlled regions are indicated as lightly shaded regions, and the uncontrolled regions are indicated as darkly shaded regions. The controlled region in which the right quadriceps were stimulated is labeled as $Q^R$, and the controlled region in which the left quadriceps were stimulated is labeled as $Q^L$. Additionally, the dead points are labeled as $q_n^*$ and $q_{n+1}^*$, and the switching states are labeled as $q_n^{on}$, $q_{n+1}^{on}$, $q_n^{off}$, and $q_{n+1}^{off}$.

A. Open-Loop Error System

The control objective was to track a desired crank trajectory with performance quantified by the tracking error signals $e_1, e_2 \in \mathbb{R}$, which were defined as:

$$e_1 \triangleq q_d - q \quad (140)$$

$$e_2 \triangleq \dot{e}_1 + \alpha e_1 \quad (141)$$

where $q_d \in \mathbb{R}$ was the desired crank position, designed such that its derivatives existed and $\dot{q}_d, \ddot{q}_d \in \mathcal{L}_\infty$, and $\alpha \in \mathbb{R}_{>0}$, was a selectable constant. $q_d$ was generally designed to monotonically increase (e.g., backpedaling was not desired). Taking the time derivative of Equation 141, multiplying by M, and using Equations 139-141 yielded the following open-loop error system:

$$M\dot{e}_2 = \chi - Ve_2 - \begin{cases} B_k^s \Omega^s v^s & \text{if } q \in Q_c \\ 0 & \text{if } q \in Q_u \end{cases} \quad (142)$$

where the auxiliary term $\chi \in \mathbb{R}$ was defined as:

$$\chi \triangleq M(\ddot{q}_d + \alpha \dot{e}_1) + V(\dot{q}_d + \alpha e_1) + G + \tau_d - \tau_b - P \quad (143)$$

Based on Equation 143 and Properties 1-6, $\chi$ could be bounded as:

$$|\chi| \le c_1 + c_2 \|z\| + c_3 \|z\|^2 \quad (144)$$

where $c_1, c_2, c_3 \in \mathbb{R}_{>0}$, were known constants. The error vector $z \in \mathbb{R}^2$ was defined as:

$$z \triangleq [e_1 e_2]^T \quad (145)$$

B. Closed-Loop Error System

Based on Equation 142 and the subsequent stability analysis, the control input (e.g., voltage) was designed as:

$$v^s \triangleq -k_1 e_2 - (k_2 + k_3 \|z\| + k_4 \|z\|^2) \operatorname{sgn}(e_2) \quad (146)$$

where sgn(•) denoted the signum function and $k_1, k_2, k_3, k_4 \in \mathbb{R}_{>0}$, were constant control gains. After substituting Equation 146 into the open-loop error system in Equation 142, the following switched closed-loop error system was obtained:

$$M\dot{e}_2 = \quad (147)$$
$$\chi - Ve_2 - \begin{cases} B_k^s \Omega^s [k_1 e_2 + (k_2 + k_3 \|z\| + k_4 \|z\|^2) \operatorname{sgn}(e_2)] & \text{if } q \in Q_c \\ 0 & \text{if } q \in Q_u \end{cases}$$

The controller in Equation 146 could have been designed to include $(B_k^s)^{-1}$ to cancel the preceding $B_k^s$, since $B_k^s$, was known, and the result would have had less strict gain conditions. However, doing so would have caused sharp increases of the control input near the uncontrolled regions, depending on the choice of $\varepsilon$, resulting in large magnitude stimulation of the muscles in regions where their effectiveness was low.

IV. Stability Analysis $V_L: \mathbb{R}^2 \to \mathbb{R}$ denoted a continuously differentiable, positive definite, radially unbounded, common Lyapunov-like function defined as:

$$V_L \triangleq \frac{1}{2} z^T W z \tag{148}$$

where the positive definite matrix $W \in \mathbb{R}^{2 \times 2}$ was defined as:

$$W \triangleq \begin{bmatrix} 1 & 0 \\ 0 & M \end{bmatrix} \tag{149}$$

$V_L$ satisfied the following inequalities:

$$\lambda_1 \|z\|^2 \leq V_L \leq \lambda_2 \|z\|^2 \tag{150}$$

where $\lambda_1, \lambda_2 \in \mathbb{R}_{>0}$, were known constants defined as:

$$\lambda_1 \triangleq \min\left(\frac{1}{2}, \frac{c_m}{2}\right), \lambda_2 \triangleq \max\left(\frac{1}{2}, \frac{c_M}{2}\right) \tag{151}$$

Theorem 1. For $q \in Q_c$, the closed-loop error system in Equation 147 was exponentially stable in the sense that:

$$\|z(t)\| \leq \sqrt{\frac{\lambda_2}{\lambda_1}} \|z(t_n^{on})\| e^{-\frac{\gamma_1}{2\lambda_2}(t-t_n^{on})} \forall t \in (t_n^{on}, t_n^{off}), \forall n \tag{152}$$

where $\gamma_1 \in \mathbb{R}_{>0}$ was defined as:

$$\gamma_1 \triangleq \min\left(\alpha - \frac{1}{2}, \epsilon c_{\Omega 1} k_1 - \frac{1}{2}\right) \tag{153}$$

provided the following gain conditions were satisfied:

$$\alpha > \frac{1}{2}, k_1 > \frac{1}{2\epsilon c_{\Omega 1}}, k_2 \geq \frac{c_1}{\epsilon c_{\Omega 1}}, k_3 \geq \frac{c_2}{\epsilon c_{\Omega 1}}, k_4 \geq \frac{c_3}{\epsilon c_{\Omega 1}} \tag{154}$$

Proof: Let $z(t)$ for $t \in (t_n^{on}, t_n^{off})$ be a Filippov solution to the differential inclusion $\dot{z} \in K[h](z)$, where $h: \mathbb{R} \times \mathbb{R} \to \mathbb{R}^2$ was defined as:

$$h \triangleq \begin{bmatrix} \dot{e}_1 \\ \dot{e}_2 \end{bmatrix} = \begin{bmatrix} e_2 - \alpha e_1 \\ M^{-1}\{\chi - V e_2 + B_k^s \Omega^s [k_1 e_2 + (k_2 + k_3 \|z\| + k_4 \|z\|^2)\mathrm{sgn}(e_2)]\} \end{bmatrix} \tag{155}$$

The time derivative of Equation 148 existed almost everywhere (a.e.) for almost all $t \in (t_n^{on}, t_n^{off})$, and $\dot{V}_L(z) \in \overline{\dot{V}}_L(z)$, where $\overline{\dot{V}}_L(z)$ was the generalized time derivative of Equation 148 along the Filippov trajectories of $\dot{z} = h(z)$ and was defined as:

$$\overline{\dot{V}}_L \triangleq \bigcap_{\xi \in \delta V_L(z)} \xi^T K \begin{bmatrix} h(z) \\ 1 \end{bmatrix} \tag{156}$$

where $\delta V_L$ was the generalized gradient of $V_L$. Since $V_L$ was continuously differentiable in $z$, $\delta V_L = \{\nabla V_L\}$, and:

$$\overline{\dot{V}}_L \subset -\alpha e_1^2 + e_1 e_2 + \chi e_2 + \frac{1}{2}(\dot{M} - V) e_2^2 + \\ B_k^s \Omega^s (k_1 e_2^2) + B_k^s \Omega^s (k_2 + k_3 \|z\| + k_4 \|z\|^2) K[\mathrm{sgn}](e_2) e_2, \tag{157}$$

where $K[\mathrm{sgn}](e_2) = \mathrm{SGN}(e_2)$ and:

$$\mathrm{SGN}(e_2) \triangleq \begin{cases} 1 & \text{if } e_2 > 0 \\ [1,1] & \text{if } e_2 = 0 \\ -1 & \text{if } e_2 < 0 \end{cases} \tag{158}$$

Using Property 8 and the fact that $B_k^s(q) < 0 \; \forall q \in Q_c$, Equation 157 was rewritten as:

$$\overline{\dot{V}}_L \subset -\alpha e_1^2 + e_1 e_2 + \chi e_2 - |B_k^s|\Omega^s(k_1 e_2^2) - |B_k^s|\Omega^s(k_2 + k_3 \|z\| + k_4 \|z\|^2) \mathrm{SGN}(e_2) e_2 \tag{159}$$

Since almost everywhere $\dot{V}_L(z) \in \overline{\dot{V}}_L(z)$, Equation 159 demonstrated that, almost everywhere:

$$\dot{V}_L = -\alpha e_1^2 + e_1 e_2 + \chi e_2 - |B_k^s|\Omega^s(k_1 e_2^2) - |B_k^s|\Omega^s(k_2 + k_3 \|z\| + k_4 \|z\|^2)|e_2| \tag{160}$$

By using Young's inequality, equation 144, Property 7, and the fact that $\in < \max(-B_k^s)$, Equation 159 could be upper bounded, almost everywhere, as:

$$\dot{V}_L \leq -\left(\alpha - \frac{1}{2}\right) e_1^2 - \left(\epsilon c_{\Omega 1} k_1 - \frac{1}{2}\right) e_2^2 + (c_1 - \epsilon c_{\Omega 1} k_2)|e_2| + \\ (c_2 - \epsilon c_{\Omega 1} k_3)\|z\| |e_2| + (c_3 - \epsilon c_{\Omega 1} k_4)\|z\|^2 |e_2| \tag{161}$$

Provided the gain conditions in Equation 154 were satisfied, Equation 150 could be used to rewrite Equation 161 as:

$$\dot{V}_L \leq -\frac{\gamma_1}{\lambda_2} V_L \tag{162}$$

where $\gamma_1$ was defined in Equation 153. The inequality in Equation 162 could be rewritten as:

$$e^{\frac{\gamma_1}{\lambda_2}(t-t_n^{on})} \left(\dot{V}_L + \frac{\gamma_1}{\lambda_2} V_L\right) \leq 0 \tag{163}$$

which was equivalent to the following expression:

$$\frac{d}{dt}\left(V_L e^{\frac{\gamma_1}{\lambda_2}(t-t_n^{on})}\right) \leq 0. \tag{164}$$

Taking the Lebesgue integral of Equation 164 and recognizing that the integrand on the left-hand size was absolutely continuous allowed the Fundamental Theorem of Calculus to be used to yield:

$$V_L e^{\frac{\gamma_1}{\lambda_2}(t-t_n^{on})} \leq C \tag{165}$$

where $C \in \mathbb{R}$ was a constant of integration equal to $V_L(z(t_n^{on}))$. Therefore:

$$V_L(z(t)) \leq V_L(z(t_n^{on})) e^{-\frac{\gamma_1}{\lambda_2}(t-t_n^{on})} \forall t \in (t_n^{on}, t_n^{off}), \forall n \tag{166}$$

Using Equation 150 to rewrite Equation 166 and performing some algebraic manipulation yielded Equation 152.

Remark 1. Theorem 1 guaranteed that desired crank trajectories could be tracked with exponential convergence, provided that the crank angle did not exit the controlled region. Thus, if the controlled regions and desired trajectories were designed appropriately, the controller in Equation 146 yielded exponential tracking of the desired trajectories for all time. If the crank position exited the controlled region, the system became uncontrolled. The resulting error system behavior was described by Theorem 2.

Theorem 2: For $q \in Q_u$, the closed-loop error system in Equation 147 could be bounded as follows:

$$\|z(t)\| \leq \frac{1}{2a_1\sqrt{\lambda_1}} \tag{167}$$

$$\left\{ a_3 \tan\left[\frac{a_3}{4}(t - t_n^{off}) + \tan^{-1}\left(\frac{2a_1}{a_3}\sqrt{\lambda_2}\|z(t_n^{off})\| + \frac{a_2}{a_3}\right)\right] - a_2 \right\}$$

$$\forall t \in [t_n^{off}, t_{n+1}^{on}], \forall n$$

provided the time spent in the uncontrolled region $\Delta t_n^{off} \triangleq t_{n+1}^{on} - t_n^{off}$ was sufficiently small such that:

$$\Delta t_n^{off} < \frac{1}{a_3}\left[2\pi - 4 \tan^{-1}\left(\frac{2a_1}{a_3}\sqrt{\lambda_2}\|z(t_n^{off})\| + \frac{a_2}{a_3}\right)\right] \forall n \tag{168}$$

where $a_1, a_2, a_3 \in \mathbb{R}_{>0}$ were known constants defined as:

$$a_1 \triangleq \frac{c_3}{(\lambda_1)^{\frac{3}{2}}}, \; a_2 \triangleq \frac{c_2 + \frac{1}{2}}{\lambda_1}, \; a_3 \triangleq \frac{4a_1 c_1}{\sqrt{\lambda_1}} - a_2^2 \tag{169}$$

Proof: The time derivative of Equation 148 for all $t \in [t_n^{off}, t_{n+1}^{on}]$ could be expressed using Equations 141, 147, and Property 8 as:

$$\dot{V}_L = -\alpha e_1^2 + e_1 e_2 + \chi e_2. \tag{170}$$

Young's inequality, Equation 144, and Equation 145 allowed Equation 170 to be upper bounded as:

$$\dot{V}_L \leq c_3 \|z\|^3 + \left(c_2 + \frac{1}{2}\right)\|z\|^2 + c_1 \|z\| \tag{171}$$

Using Equation 150, Equation 171 could be upper bounded as:

$$\dot{V}_L \leq \frac{c_3}{(\lambda_1)^{\frac{3}{2}}} V_L^{\frac{3}{2}} + \frac{c_2 + \frac{1}{2}}{\lambda_1} V_L + \frac{c_1}{\sqrt{\lambda_1}} V_L^{\frac{1}{2}} \tag{172}$$

The solution to Equation 172 yielded the following upper bound on $V_L$ in the uncontrolled region:

$$V_L(z(t)) \leq \tag{173}$$

$$\frac{1}{4a_1^2}\left\{ a_3 \tan\left[\frac{a_3}{4}(t - t_n^{off}) + \tan^{-1}\left(\frac{2a_1}{a_3}\sqrt{V_L(z(t_n^{off}))} + \frac{a_2}{a_3}\right)\right] - a_2 \right\}^2$$

$$\forall t \in [t_n^{off}, t_{n+1}^{on}], \forall n$$

Equation 173 was rewritten using Equation 150, and algebraic manipulation was performed to yield Equation 167.

Remark 2. The bound in Equation 167 had a finite escape time, so $\|z\|$ could become unbounded unless the reverse dwell-time condition (RDT) in Equation 168 was satisfied. In other words, the argument of $\tan(\cdot)$ in Equation 167 must be less than $$\frac{\pi}{2}$$

to ensure boundedness of $\|z\|$. The following assumption and subsequent remark detailed how the RDT condition may be satisfied.

Assumption 1: The time spent in the $n^{th}$ controlled region $\Delta t_n^{on} \triangleq t_n^{off} - t_n^{on}$ had a known positive lower bound $\Delta t_{min}^{on} \in \mathbb{R}_{>0}$, such that:

$$\min_n \Delta t_n^{on} \geq \Delta t_{min}^{on} > 0 \tag{174}$$

Likewise, the time spent in the $n^{th}$ uncontrolled region $\Delta t_n^{off}$ had a positive upper bound $\Delta t_{max}^{off} \in \mathbb{R}_{>0}$, that satisfied $\max_n \Delta t_{no}^{n} \leq \Delta t_{max}^{off}$ and Equation 168 for all n:

$$\Delta t_{max}^{off} < \frac{1}{a_3}\left[2\pi - 4 \tan^{-1}\left(\frac{2a_1}{a_3}\sqrt{\lambda_2}\|z(t_n^{off})\| + \frac{a_2}{a_3}\right)\right] \forall n \tag{175}$$

Remark 3. Assumption 1 could be validated through appropriate design of the desired crank velocity $\dot{q}_d$. The term $\Delta t_{min}^{on}$, was first considered. The time spent in the $n^{th}$ controlled region $\Delta t_n^{on}$ was described using the Mean Value Theorem as:

$$\Delta t_n^{on} = \frac{\Delta q_n^{on}}{\dot{q}(\xi_n^{on})}, \tag{176}$$

where $\Delta q_n^{on} \triangleq q(t_n^{off}) - q(t_n^{on})$ the length of the $n^{th}$ controlled region. In this Example, the length $\Delta q_n^{on}$ was constant for all $n \geq 1$ and was smallest for $n=0$. $\dot{q}(\xi_n^{on}) \in \mathbb{R}$ was the average crank velocity through the $n^{th}$ controlled region. Using Equations 140 and 141 and assuming $\dot{e}_1 < 0$, $\dot{q}$ was upper bounded as:

$$\dot{q} \leq \dot{q}_d + (1+\alpha)\|z\| \tag{177}$$

Then, Equations 150 and 177 were combined with the fact that $\|z\|$ monotonically decreased in the controlled regions to upper bound the average crank velocity $\dot{q}(\xi_n^{on})$ as:

$$\dot{q}(\xi_n^{on}) \leq \dot{q}_d(t_n^{on}) + (1+\alpha)\sqrt{\frac{\lambda_2}{\lambda_1}}\|z(t_n^{on})\| \tag{178}$$

Equation 176 was then lower bounded using Equation 178 as:

$$\Delta t_n^{on} \geq \frac{\Delta q_n^{on}}{\dot{q}_d(t_n^{on}) + (1+\alpha)\|z(t_n^{on})\|} \quad (179)$$

If a desired $\Delta t_{min}^{on}$ was specified, the right-hand side of Equation 179 needed to be greater than or equal to the selected $\Delta t_{min}^{on}$. For example:

$$\frac{\Delta q_n^{on}}{\dot{q}_d(t_n^{on}) + (1+\alpha)\|z(t_n^{on})\|} \geq \Delta t_{min}^{on} \quad (180)$$

which could be rewritten as:

$$\dot{q}_d(t_n^{on}) \leq \frac{\Delta q_n^{on}}{\Delta t_{min}^{on}} - (1+\alpha)\|z(t_n^{on})\| \quad (181)$$

From Equation 181 an upper bound on the desired velocity at each on-time was given which guaranteed that on-duration $\Delta t_n^{on}$ was greater than a specified minimum on-duration $\Delta t_{min}^{on}$. Therefore, designing the desired velocity to satisfy Equation 181 for all n was sufficient to validate the first part of Assumption 1.

$\Delta t_{max}^{off}$ was then considered. The crank's entrance into the uncontrolled region could be likened to a ballistic event, where the crank was carried by the controller to $q(t_n^{off})$ and released with initial velocity $\dot{q}(t_n^{off})$. In that sense, specifying a desired $\Delta t_{max}^{off}$ was equivalent to requiring the crank to ballistically (e.g., only under the influence of passive dynamics) traverse the length of the uncontrolled region, $\Delta q_n^{off}$, in a sufficiently short amount of time. Since the initial conditions were generally the only controllable factors affecting the behavior of the crank in the uncontrolled region, and since initial condition $q(t_n^{off})$ was predetermined by choice of $\varepsilon$, initial velocity $\dot{q}(t_n^{off})$ was used to guarantee that the total time spent in the $n^{th}$ controlled region was less than $\Delta t_{max}^{off}$. If it was reasonably assumed that $t_n^{off} \propto \dot{q}(t_n^{off})^{-1}$, then it could be assumed that there existed a sufficiently large initial velocity a critical velocity—$\dot{q}^{crit} \in \mathbb{R}_{>0}$—which guaranteed $\Delta t_n^{off} \leq \Delta t_{max}^{off}$. More specifically, it was supposed that there existed $\dot{q}^{crit}$ such that:

$$\dot{q}(t_n^{off}) \geq \dot{q}^{crit} \Rightarrow \Delta t_n^{off} \leq \Delta t_{max}^{off} \quad (182)$$

Using Equations 140 and 141, and assuming $\dot{e} > 0$, initial velocity $\dot{q}(t_n^{off})$ was lower bounded as:

$$\dot{q}(t_n^{off}) \geq \dot{q}_d(t_n^{off}) - (1+\alpha)\|z(t_n^{off})\| \quad (183)$$

Combining Equations 182 and 183, the sufficient condition for the desired crank velocity at the $n^{th}$ off-time which guaranteed Equation 182 was developed:

$$\dot{q}_d(t_n^{off}) \geq \dot{q}^{crit} + (1+\alpha)\|z(t_n^{off})\| \quad (184)$$

Furthermore, Equation 152 was used to obtain a sufficient condition for Equation 184 in terms of the initial conditions of each cycle as:

$$\dot{q}_d(t_n^{off}) \geq \dot{q}^{crit} + (1+\alpha)\sqrt{\frac{\lambda_2}{\lambda_1}}\|z(t_n^{on})\|e^{-\frac{\gamma_1}{2\lambda_2}\Delta t_{min}^{on}} \quad (185)$$

It was noted that increasing $\gamma_1$ via selection of $\alpha$ and $k_1$ relaxed Equation 185 to a limit where only $\dot{q}_d(t_n^{off}) \geq \dot{q}^{crit}$ was required.

Therefore, satisfaction of both Equations 181 and 185 for all n was sufficient to validate Assumption 1. However, Equation 185 depended on knowledge of $\dot{q}^{crit}$ which led to additional Assumption 2.

Assumption 2. The critical velocity $\dot{q}^{crit}$ was known a priori for all n. This assumption was mild in the sense that the critical velocity could be experimentally determined for an individual system configuration or numerically calculated for a wide range of individual or cycle configurations.

Theorem 3. The closed-loop error system in Equation 1474 was ultimately bounded in the sense that, as the number of crank cycles approached infinity (e.g., as $n \to \infty$), $\|z(t)\|$ converged to a ball with constant radius $\bar{d} \in \mathbb{R}_{>0}$.

Proof: There were three possible scenarios that could have described the behavior of $V_L$ with each cycle: (1) $V_L(z(t_{n+1}^{on})) < V_L(z(t_n^{on}))$, (2) $V_L(z(t_{n+1}^{on})) > V_L(z(t_n^{on}))$, and (3) $V_L(z(t_{n+1}^{on})) = V_L(z(t_n^{on}))$. The potential decay and growth of $V_L$ in the controlled and uncontrolled regions, respectively, dictated which of these three behaviors occurred. In scenario (1), the decay was greater than the growth, causing $V_L$ to decrease with each cycle. Conversely, in scenario (2), the growth was greater than the decay, causing $V_L$ to grow with each cycle. Since the amount of decay or growth was proportional to the initial conditions for each region, $V_L(z(t_n^{on}))$ and $V_L(z(t_n^{off}))$, as the number of crank cycles approached infinity, the magnitude of the potential decay eventually equaled the magnitude of the potential growth, resulting in scenario (3) and an ultimate bound on $V_L$.

It was supposed that $V_L(z(t_n^{on}))$ reached the ultimate bound $\bar{d}$ after N cycles. Then, $V_L(z(t_{n+1}^{on})) = \bar{d}$ for all $n \geq N-1$. $\bar{d}$ was then found by considering the most conservative case, where the minimum possible decay and the maximum possible growth were equal. For off example, it was considered that $V_L(z(t_n^{on})) = \bar{d}$ with $\Delta t_n^{on} = \Delta t_{min}^{on}$ and $\Delta t_n^{off} = \Delta t_{max}^{off}$ for all n. Therefore, the most conservative ultimate bound on $V_L$ was found by solving the following equation for $\bar{d}$ using Equation 166 with $\Delta t_{min}^{on}$ and Equation 173 with $\Delta t_{max}^{off}$:

$$\bar{d} = \frac{1}{4a_1^2}\left\{a_3\tan\left[\frac{a_3}{4}\Delta t_{max}^{off} + \tan^{-1}\left(\frac{2a_1}{a_3}\sqrt{\bar{d}}\,e^{-\frac{\gamma_1}{2\lambda_2}\Delta t_{min}^{on}} + \frac{a_2}{a_3}\right)\right] - a_2\right\}^2 \quad (186)$$

Algebraic manipulation of Equation 186 gave the following quadratic polynomial in $\sqrt{\bar{d}}$:

$$b_1\bar{d} + b_2\sqrt{\bar{d}} + b_3 = 0 \quad (187)$$

where $b_1, b_2, b_3 \in \mathbb{R}_{\geq 0}$ were known constants defined as:

$$b_1 \triangleq -4a_1^2\tan\left(\frac{a_3}{4}\Delta t_{max}^{off}\right)e^{-\frac{\gamma_1}{2\lambda_2}\Delta t_{min}^{on}}, \quad (188)$$

$$b_2 \triangleq 2a_1 a_3\left(1 - e^{-\frac{\gamma_1}{2\lambda_2}\Delta t_{min}^{on}}\right) - 2a_1 a_2\tan\left(\frac{a_3}{4}\Delta t_{max}^{off}\right)\left(1 + e^{-\frac{\gamma_1}{2\lambda_2}\Delta t_{min}^{on}}\right), \quad (189)$$

$$b_3 \triangleq -(a_2^2 + a_3^2)\tan\left(\frac{a_3}{4}\Delta t_{max}^{off}\right) \quad (190)$$

Solving Equation 186 for $\bar{d}$, provided that $b_1, b_2, b_3$ did not equal 0, gave the resulting ultimate bound on $V_L(z(t_n^{on}))$ $\forall n \geq N$:

$$\bar{d} = \left(\frac{-b_2 + \sqrt{b_2^2 - 4b_1 b_3}}{2b_1}\right)^2 \tag{191}$$

Additionally, the ultimate bound on $V_L$ $(z(t_n^{off}))\forall n \geq N$ was found by considering the minimum decay of $V_L$ in the controlled regions after the ultimate bound had been reached. The bound $\underline{d} \in \mathbb{R}_{\leq 0}$ was found as:

$$\underline{d} \triangleq \bar{d} e^{-\frac{\gamma_1}{\lambda_2}\Delta t_{min}^{on}} \tag{192}$$

Since the bounds on $V_L$ strictly decreased in the controlled region and increased in the uncontrolled regions, it was demonstrated that $V_L(z(t)) \leq \bar{d} \forall t \geq t_N^{on}$ when $V_L(z(t_N^{on})) \leq \bar{d}$, or equivalently, $\forall t \geq t_N^{off}$ when $V_L(z(t_N^{off})) \leq \underline{d}$. In other words, if the magnitude of $V_L$ was smaller than $\bar{d}$ when the controller was switched on or smaller than $\underline{d}$ when the controller was switched off, then $V_L$ would henceforth remain smaller than $d$. Using Equation 150, it was demonstrated that as n approached infinity, $\|z(t)\|$ converged to a ball with constant radius. In other words:

$$z(t) \to d \text{ as } n \to \infty \tag{193}$$

where $d \in \mathbb{R}_{>0}$ was a constant defined as:

$$d \triangleq \sqrt{\frac{\bar{d}}{\lambda_1}} \tag{194}$$

Remark 4. The size of the ultimate bound d depended on the bounds of the inertia matrix given in Property 1, the bounds of x given in Equation 144, the minimum time spent in the controlled region $\Delta t_{max}^{off}$, and the control gain $\gamma_1$. However, the effect of the control gain was limited:

$$\lim_{\gamma_1 \to \infty} \bar{d} = \left[\frac{-(a_2^2 + a_3^2)\tan\left(\frac{a_3}{4}\Delta t_{max}^{off}\right)}{2a_1 a_2 \tan\left(\frac{a_3}{4}\Delta t_{max}^{off}\right) - 2a_1 a_3}\right]^2 \tag{195}$$

$$\lim_{\gamma_1 \to \infty} \underline{d} = 0 \tag{196}$$

Based on Equations 195 and 196, the lower limit of $V_L$ could be driven to zero by choosing the gains to be arbitrarily large, but $V_L$ would always have a nonzero upper bound while $\Delta t_{max}^{off} > 0$. Therefore, the size of the ultimate bound could be further minimized by ensuring smaller off-times to reduce $\Delta t_{max}^{off}$ as described in Remark 3. Indeed, if the maximum time spent in the uncontrolled regions were identically zero (e.g., the uncontrolled regions were Lebesgue negligible), then the ultimate bound would also be identically zero, suggesting exponential convergence to the desired trajectory.

V. Experimental Results

A. Methods

Three FES-induced cycling trials were performed on five able-bodied male subjects, with written informed consent approved by the University of Florida Institutional Review Board. The goal of these trials was to demonstrate the tracking performance and robustness of the controller in Equation 146 and to evaluate the effect of ε on control input and performance.

Figure 9:
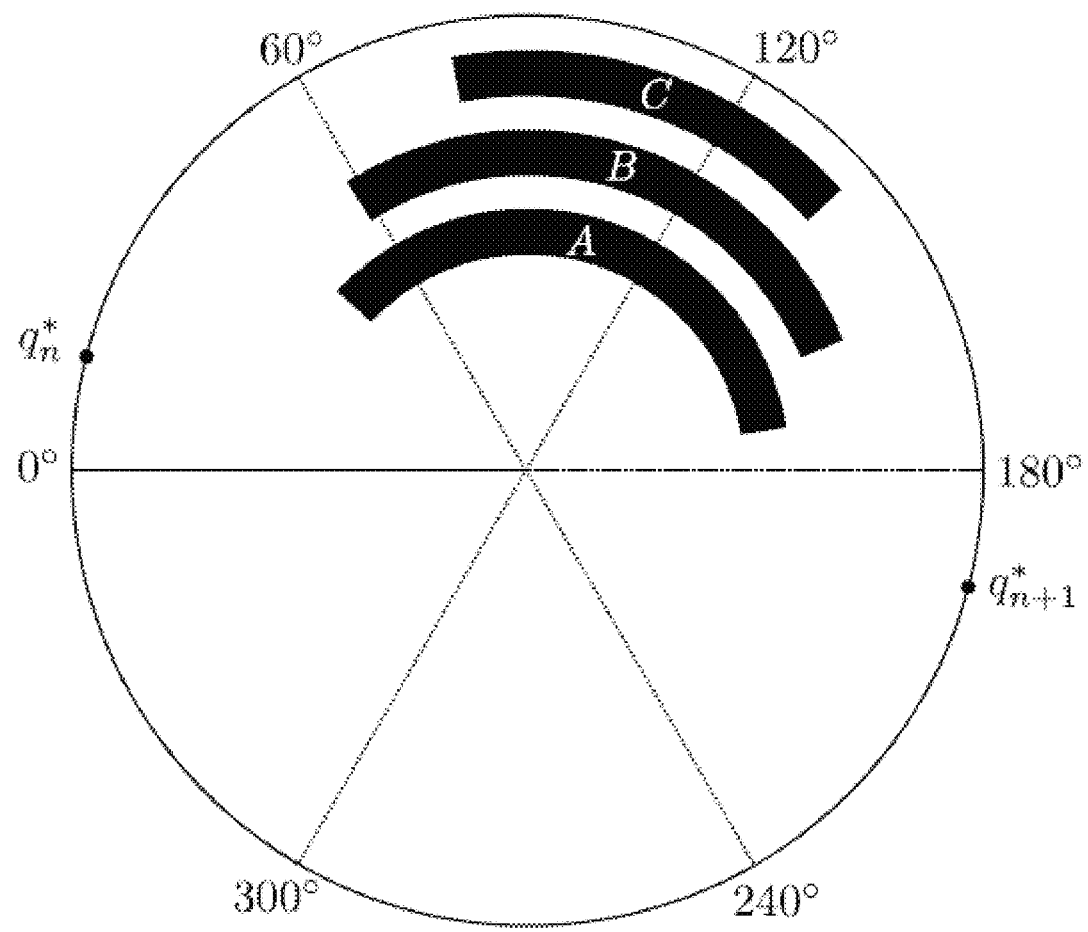
FIG. 9 shows stimulation regions used for a subject during experimental trials, according to one set of embodiments.

Each trial was randomly assigned a protocol listed in Table I, and the corresponding value of ε was used to determine the stimulation region for that trial, where $B_k^{max} \triangleq \max_{q \in Q} B_k(q)$ was the maximum value of the subject's torque transfer ratio. The protocols used for each subject and trial were tabulated in Table II. FIG. 9 illustrates the stimulation regions used for Subject 4, with shaded segments representing $Q^R$ for protocols A, B, and C ($Q^L$, which was not shown, would be rotated by 180°). FIG. 9 also shows the dead points for Subject 4, as indicated by $q_n^*$ and $q_{n+1}^*$. Trials were ended if 90 revolutions had been completed, the control input saturated at 400 microseconds, or the subject reported significant discomfort.

TABLE I

| Protocol | ε |
|---|---|
| A | 0.5 $B_k^{max}$ |
| B | 0.7 $B_k^{max}$ |
| C | 0.9 $B_k^{max}$ |

TABLE II

| Subject | $B_k^{max}$ | Trial | Protocol | E |
|---|---|---|---|---|
| 1 | 0.49 | 1 | B | 0.34 |
|   |      | 2 | A | 0.25 |
|   |      | 3 | C | 0.44 |
| 2 | 0.55 | 1 | A | 0.27 |
|   |      | 2 | B | 0.38 |
|   |      | 3 | C | 0.49 |
| 3 | 0.53 | 1 | B | 0.37 |
|   |      | 2 | C | 0.47 |
|   |      | 3 | A | 0.26 |
| 4 | 0.50 | 1 | C | 0.45 |
|   |      | 2 | B | 0.35 |
|   |      | 3 | A | 0.25 |
| 5 | 0.52 | 1 | C | 0.47 |
|   |      | 2 | B | 0.36 |
|   |      | 3 | A | 0.26 |

Able-bodied subjects were recruited for these experiments, since the response of non-impaired subjects to electrical stimulation had been reported to be similar to the response of paraplegic subjects. During each trial, the subjects were instructed to relax and were not shown the computer screen, and at least five minutes of rest was allotted between each trial to mitigate the effects of fatigue.

Prior to the trials was a two minute warm-up period, during which the subject was shown a graph of the desired crank velocity on a computer screen along with the measured crank velocity. Each subject was asked to track the desired crank velocity to the best of their ability. This pre-trial provided a measure of volitional cycling ability, which was used as a performance benchmark.

A fixed-gear stationary recumbent cycle was equipped with an optical encoder to measure the crank angle and custom pedals upon which high-topped orthotic walking boots were affixed. The purpose of the boots was to fix the rider's feet to the pedals, hold the ankle position at 90 degrees, and maintain sagittal alignment of the legs. The cycle had an adjustable seat and a magnetically braked flywheel with 16 levels of resistance. The cycle seat position was adjusted for the comfort of each rider, provided that the rider's knees could not hyperextend while cycling. Geometric parameters of the stationary cycle and subjects were measured prior to the experiment. The following distances were measured and used to calculate $B_k$ for each subject: greater trochanter to lateral femoral condyle (thigh length), lateral femoral condyle to pedal axis (effective shank length), and the horizontal and vertical distance from the greater trochanter to the cycle crank axis (seat position). The distance between the pedal axis and the cycle crank axis (pedal length) was fixed for all subjects and therefore only measured once. Electrodes were then placed on the anterior distal-medial and proximal-lateral portions of the subjects' left and right thighs.

A current-controlled stimulator (RehaStim, Hasomed, GmbH, Germany) was used to stimulate the subjects' quadriceps femoris muscle groups through bipolar self-adhesive 3"×5" PALS® Platinum oval electrodes (provided by Axelgaard Manufacturing Co.). A personal computer equipped with data acquisition hardware and software was used to read the encoder signal, calculate the control input, and command the stimulator. Stimulation was conducted at a frequency of 40 Hz with a constant amplitude of 100 mA and a variable pulse width dictated by the controller in Equation 146.

The desired crank position and velocity were given in radians and radians per second, respectively, as:

$$q_d \triangleq 3.665(t-t_0^{on}) - \dot{q}_d + q_0^{on} \quad (197)$$

$$\dot{q}_d \triangleq 3.665[1-\exp(t_0^{on}-t)] \quad (198)$$

The trajectories in Equations 197 and 198 ensured that the desired velocity started at 0 rpm and exponentially approached 35 rpm. The following control gains were found in preliminary testing and used for all subjects:

$$\alpha=7, k_1=10, k_2=0.1, k_3=0.1, k_4=0.1 \quad (199)$$

B. Results

Figure 10A:
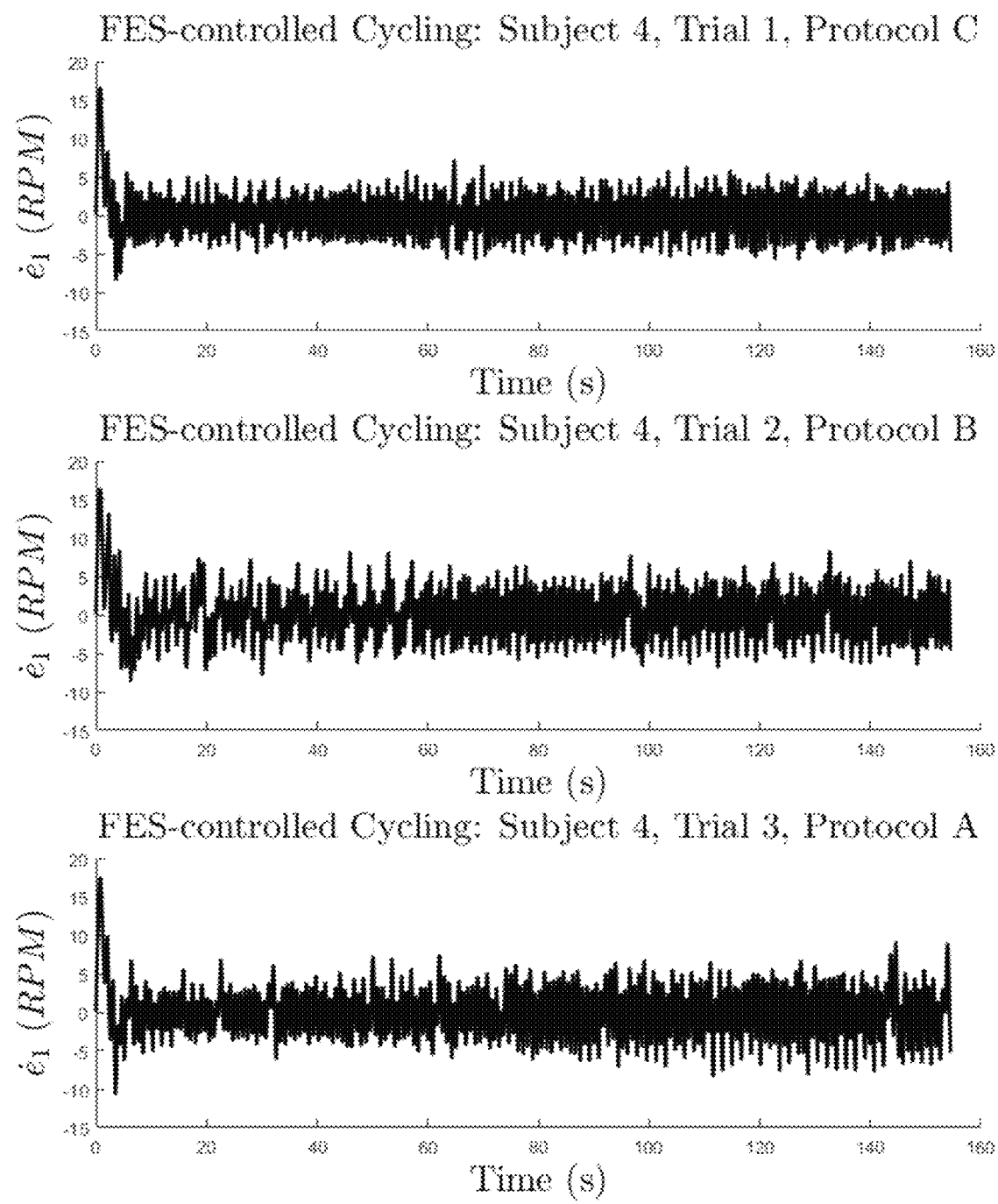
FIG. 10A shows cadence tracking error for a subject during experimental trials, according to one set of embodiments.
Figure 10B:
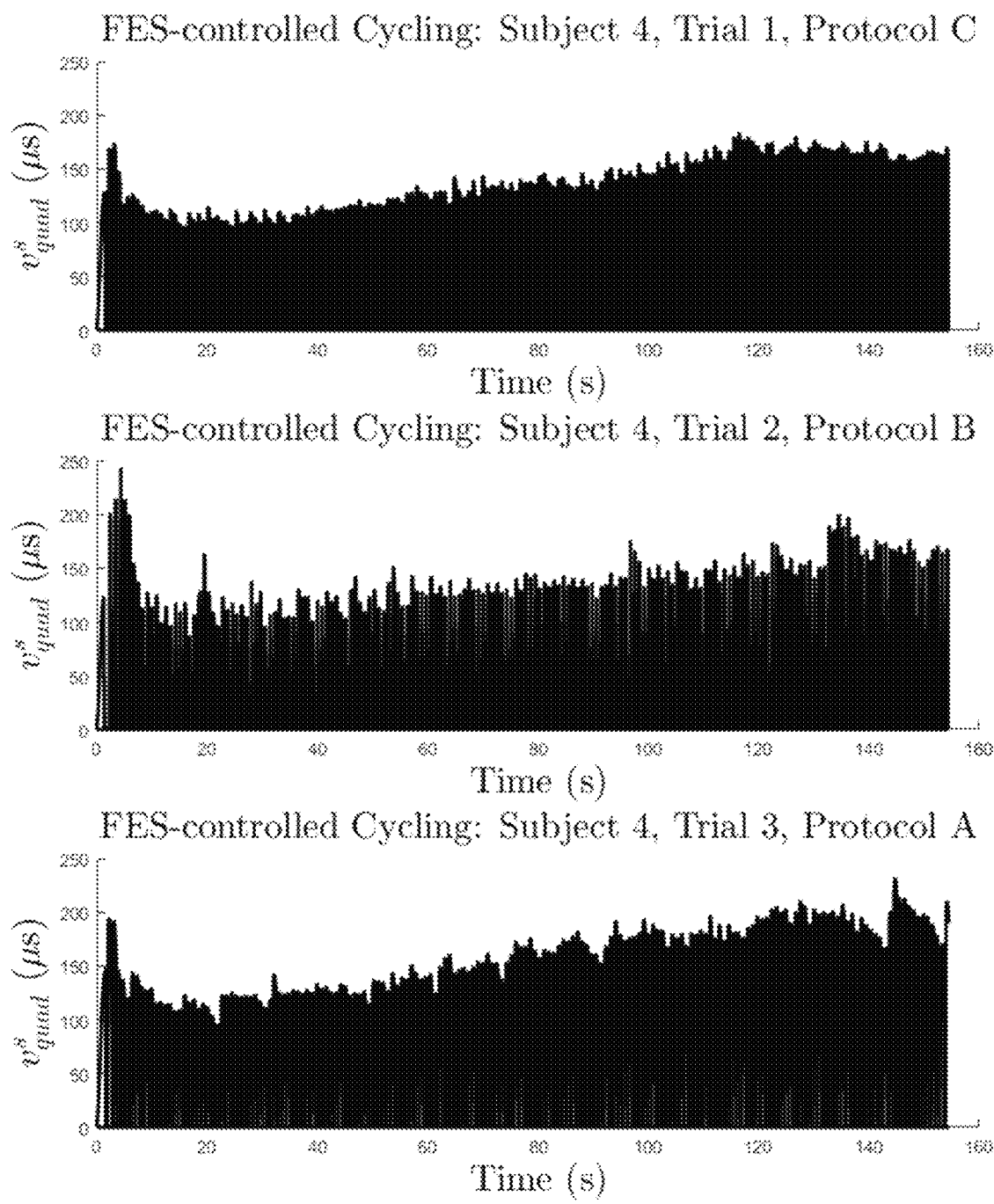
FIG. 10B shows switched control input for a subject during experimental trials, according to one set of embodiments.
Figure 11:
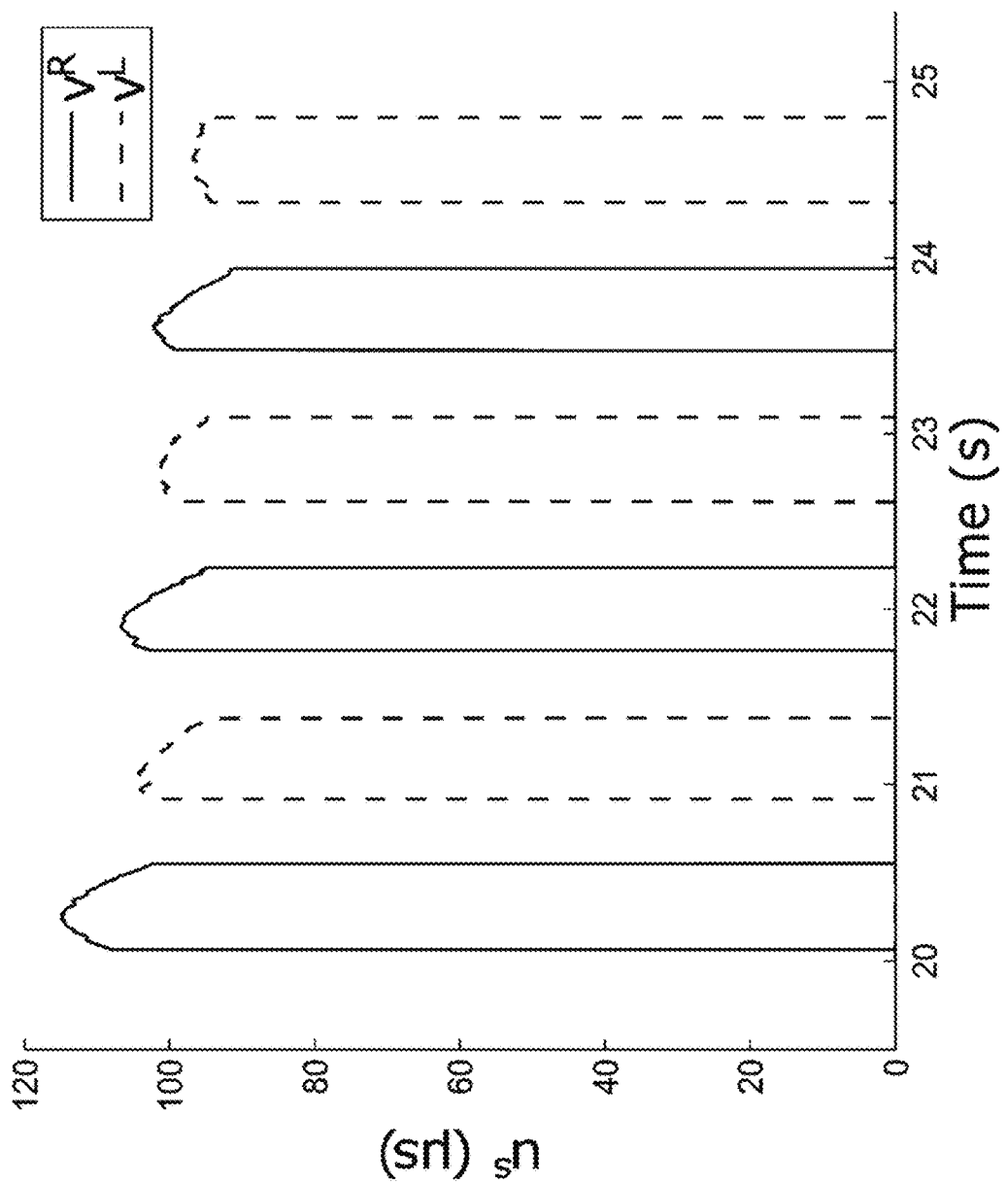
FIG. 11 shows, according to one set of embodiments, switched control input from the first experimental trial of a subject.
Figure 12:
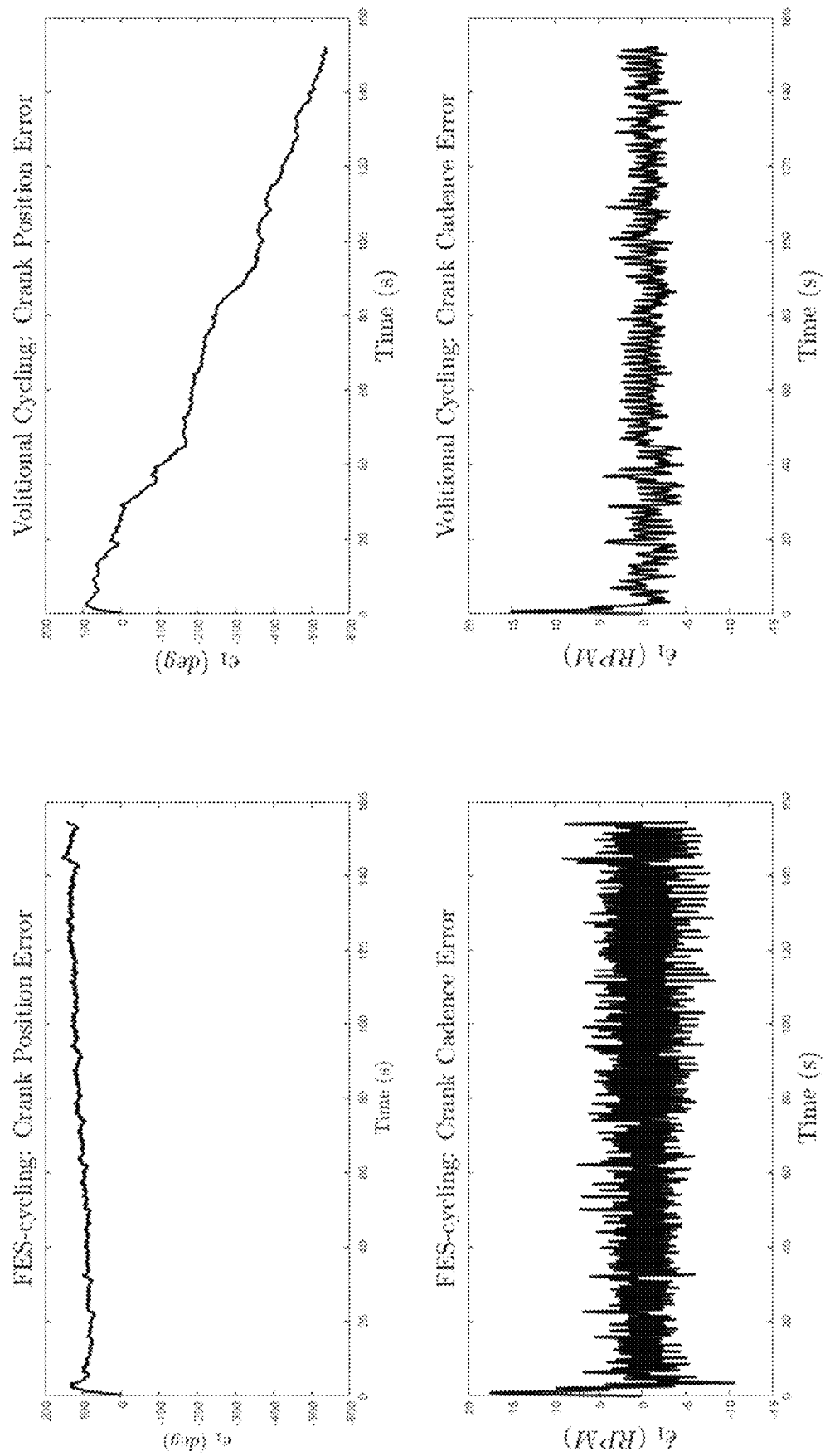
FIG. 12 shows position and cadence tracking errors during FES-induced cycling and volitional cycling for a subject during experimental trials, according to some embodiments.

The mean, standard deviation, and root mean square (RMS) of the cadence tracking error $\dot{e}_1$ in revolutions per minute (RPM) are shown in Table III for all subjects over all trials, including the volitional warm-up. FIG. 10A shows plots of cadence tracking error $\dot{e}_1$ as a function of time for each of the three trials of a representative subject, Subject 4. FIG. 10B shows plots of switched control input $u^s$ versus time for each of the three trials of Subject 4. FIG. 11 shows the control input $u^s$ from the first trial for Subject 4 over the interval from 20 seconds to 25 seconds, to more clearly illustrate the behavior of the switched control input. FIG. 12 compares the position tracking error $e_1$ (top) and cadence tracking error $\dot{e}_1$ (bottom) during FES-induced cycling (left) and volitional cycling (right) for Subject 4.

TABLE III

| Subject | Protocol | $\dot{e}_1$ mean (RPM) | $\dot{e}_1$ standard deviation (RPM) | $\dot{e}_1$ RMS (RPM) |
|---|---|---|---|---|
| 1 | Volitional | -0.5273 | 2.3545 | 2.4128 |
|   | A | 0.1922 | 3.1220 | 3.1279 |
|   | B | 0.1222 | 2.6596 | 2.6624 |
|   | C | 0.4133 | 3.6539 | 3.6772 |
| 2 | Volitional | -0.0031 | 1.5113 | 1.5113 |
|   | A | 0.0614 | 1.9235 | 1.9244 |
|   | B | 0.0789 | 2.1177 | 2.1191 |
|   | C | 0.4849 | 3.0187 | 3.0574 |
| 3 | Volitional | 0.4652 | 3.5372 | 3.5677 |
|   | A | 0.5406 | 4.2108 | 4.2453 |
|   | B | 0.2444 | 2.5774 | 2.5890 |
|   | C | 0.2391 | 2.3912 | 2.4031 |

TABLE III-continued

| Subject | Protocol | $\dot{e}_1$ mean (RPM) | $\dot{e}_1$ standard deviation (RPM) | $\dot{e}_1$ RMS (RPM) |
|---|---|---|---|---|
| 4 | Volitional | -0.5776 | 1.8300 | 1.9190 |
|   | A | 0.1526 | 3.3128 | 3.3163 |
|   | B | 0.1317 | 3.4334 | 3.4359 |
|   | C | 0.1306 | 2.8160 | 2.8190 |
| 5 | Volitional | -0.1894 | 1.4522 | 1.4645 |
|   | A | 0.2546 | 3.1554 | 3.1657 |
|   | B | 0.4936 | 4.2282 | 4.2569 |
|   | C | 0.6886 | 4.1743 | 4.2306 |

Example 2

This Example describes the electrical stimulation of gluteal, quadriceps femoris, and hamstrings muscle groups in human riders to induce cycling (e.g., on a cycling device). In this Example, a stimulation pattern was designed based on the kinematic effectiveness of the rider's hip and knee joints to produce a forward torque about the cycle crank. A robust controller was designed for the uncertain, nonlinear cycle-rider system with autonomous, state-dependent switching. Provided sufficient conditions were satisfied, the switched controller yielded ultimately bounded tracking of a desired cadence. Experimental results on four able-bodied subjects demonstrated cadence tracking errors of 0.05±1.59 revolutions per minute during volitional cycling and 5.27±2.14 revolutions per minute during FES-induced cycling. To establish feasibility of FES-assisted cycling in subjects with Parkinson's disease, experimental results with one subject demonstrated tracking errors of 0.43±4.06 revolutions per minute during volitional cycling and 0.17±3.11 revolutions per minute during FES-induced cycling.

A stimulation pattern generally defines the segments of the crank cycle over which each of at least one muscle group is stimulated to achieve the desired cycling motion. The stimulation pattern may, in some cases, be manually determined, determined from offline numerical optimization, analytically determined, or based on able-bodied electromyography (EMG) measurements. Switching the stimulation control input between multiple muscle groups according to the cycle crank angle makes the overall FES-cycling system a switched control system with autonomous, state-dependent switching. In general, during FES-cycling, there exist periods during which one or more muscle groups are active followed by periods during which no muscle groups are active. When muscle groups are actively controlled by stimulation, the system may stably track the desired trajectory, but when no muscle groups are active, the system becomes uncontrolled and may become unstable. This behavior is complicated by the fact that the dynamics of FES-cycling are nonlinear, time-varying, and uncertain, so that the system's state trajectories (e.g., cadence) are unknown a priori. No previous studies have explored FES-cycling control while considering these properties of the FES-cycling system.

Although FES-cycling is typically utilized with subjects having spinal cord injury, its benefits have been demonstrated with subjects with cerebral palsy, multiple sclerosis, and stroke, and FES-cycling may also benefit other populations with movement disorders. One population that may benefit from FES-cycling is individuals with Parkinson's disease (PD). PD is a neurodegenerative disorder that causes both motor (e.g., decline in muscle force production, rigidity, postural instability, and tremor) and non-motor (e.g., fatigue, anxiety, and depression) symptoms. Exercise, especially in the form of assisted (i.e., forced) cycling, is an effective treatment for the motor symptoms of PD. It has been demonstrated that assisted cycling, where the rider pedals with external assistance at a rate greater than the preferred voluntary rate, yields greater improvements in motor and central nervous system function in people with PD when compared to voluntary cycling, and it has been suggested that the mechanism for these improvements may be the increased quantity and quality of intrinsic feedback during assisted cycling. It has also been demonstrated that cueing training improves motor performance in people with PD. Therefore, FES-assisted cycling, where FES is applied in addition to the rider's effort to voluntarily pedal at a prescribed cadence, has the potential to improve motor performance in people with PD, as the added FES can enhance muscle force production and provide cueing via the sensation of the stimulation during cycling. As no previous studies have investigated the use of FES-assisted cycling in people with PD, this Example provides the results of an experiment conducted with one subject with PD to establish feasibility of FES-assisted cycling in this population.

In this Example, a nonlinear model of a stationary FES-cycling system was developed that included parametric uncertainty and an unknown, bounded, time-varying disturbance. A stimulation pattern for the gluteal, quadriceps femoris, and hamstrings muscle groups was designed based on the kinematic effectiveness of the rider's hip and knee joints to produce a forward torque about the cycle crank. A switched sliding mode control input was developed based on this stimulation pattern with the objective that the rider pedal at a desired cadence. A common Lyapunov-like function was used to prove that the cadence tracking error was bounded by an exponentially decaying envelope in regions where muscle groups were activated and by an exponentially increasing envelope in regions where no muscle groups were activated. The overall error system was shown to be ultimately bounded provided sufficient conditions on the control gains, desired trajectory, and stimulation pattern were satisfied. Experimental results on able-bodied subjects and one subject with Parkinson's disease demonstrated the switched controller's performance under typical FES-cycling conditions. Cycling performance was quantified by the cadence tracking error (i.e., difference between prescribed and actual cadence), which provided a measure of the smoothness and consistency of the FES-assisted cycling, and it was demonstrated that FES-assisted cycling has the potential to improve the cycling performance of people with PD.

I. Model

A. Stationary Cycle and Rider Dynamic Model

Figure 13:
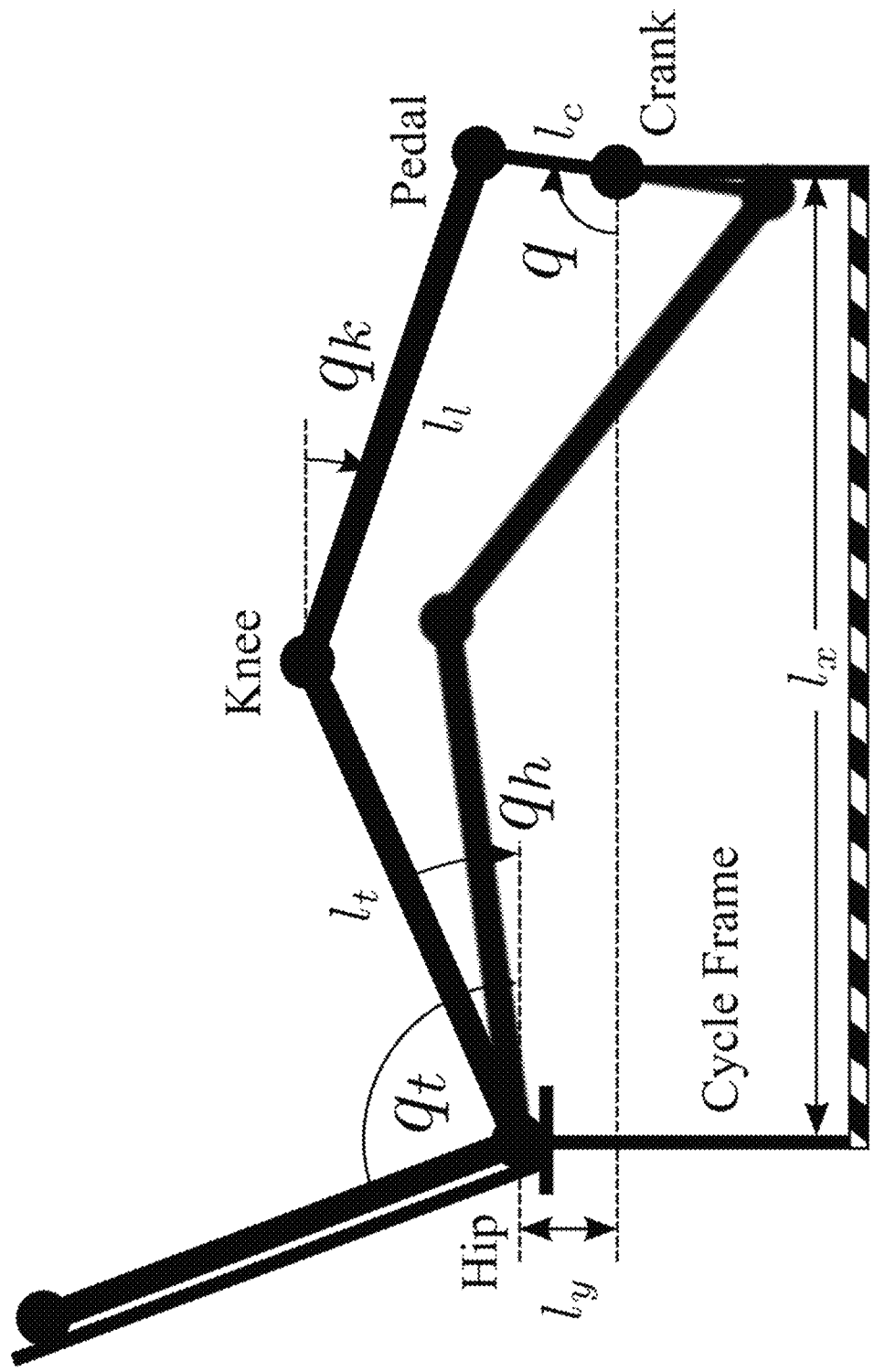
FIG. 13 shows, according to some embodiments, an exemplary schematic illustration of a system comprising a rider and a cycle.

A two-legged rider pedaling a recumbent stationary cycle was modeled as a single degree-of-freedom system, which was expressed as:

$$M\ddot{q} + V\dot{q} + G = \tau_{crank} \quad (200)$$

where $q \in Q \subset \mathbb{R}$ denoted the crank angle as defined in FIG. 13; M, V, $G \in \mathbb{R}$ denoted the effects of inertia, centripetal and Coriolis, and gravitational effects, respectively, of the combined rider and cycle about the crank axis; and $\tau_d \in \mathbb{R}$ denoted the net external torque applied about the crank axis. The recumbent stationary cycle was modeled as having three links (one link was fixed to the ground) representing the cycle frame and seat and three revolute joints representing the cycle crank and the two pedals. The other two rigid links represented the pedal crank arms, which rotated about the crank joint with a constant phase difference of it radians and terminated with a revolute joint representing a pedal. Each of the rider's legs was modeled as a two-link, serial kinematic chain with a revolute joint fixed to the cycle seat (hip joint) and another revolute joint joining the links (knee joint). The ankle joint was assumed to be fixed in the anatomically neutral position in accordance with common clinical cycling practices for safety and stability. The rider's feet were fixed to the cycle pedals, constraining the rider's legs to rotation in the sagittal plane and closing the kinematic chain. The resulting system, shown in FIG. 13, was reduced to a single degree of freedom and therefore was completely described by the crank angle (or any other single joint angle measured with respect to ground) and the rider's and cycle's link lengths. In FIG. 13, $q_t \in \mathbb{R}$ denotes the rider's trunk angle with respect to ground, $q_h \in \mathbb{R}$ denotes the measureable hip angle, $q_k \in \mathbb{R}$ denotes the measureable knee angle, and q E ill denotes the crank angle. The measureable hip and knee angles $q_h$ and $q_k$ were geometric functions of the measurable constant horizontal distance between the hip and crank joint axes $l_x \in \mathbb{R}_{>0}$ (i.e., horizontal seat position); the measurable constant vertical distance between the hip and crank joint axes $l_y \in \mathbb{R}_{>0}$ (i.e., vertical seat position); the measureable constant thigh length $l_t \in \mathbb{R}_{>0}$; the measureable constant shank length $l_l \in \mathbb{R}_{>0}$; and the measureable constant crank arm length $l_c \in \mathbb{R}_{>0}$.

The external torque applied about the crank axis was expressed as:

$$\tau_{crank} = \tau_a + \tau_p + \tau_b + \tau_d \quad (201)$$

where $\tau_a$, $\tau_p$, $\tau_b$, $\tau_d \in \mathbb{R}$ denoted the torques applied about the crank axis by active muscle forces, passive viscoelastic tissue forces, viscous crank joint damping, and disturbances (e.g., spasticity or changes in load), respectively. The active torque resulting from stimulation of the gluteal (glute), quadriceps femoris (quad), and hamstrings (ham) muscle groups was expressed as:

$$\tau_a \triangleq \sum_{s \in S} \sum_{m \in M} v_m^s \Omega_m^s T_m^s \quad (202)$$

where $v_m^s \in \mathbb{R}$ denoted the subsequently designed stimulation intensity input to each muscle group, $\Omega_m^s \in \mathbb{R}$ denoted the relationship between stimulation intensity and a muscle's resultant torque about the joint it spanned, and $T_m^s \in \mathbb{R}$ denoted the Jacobian elements relating a muscle's resultant joint torque to torque about the crank axis. The superscript $s \in S \triangleq \{R, L\}$ indicated either the right (R) or left (L) leg, and the subscript $m \in \mathcal{M} \triangleq \{glute, quad, ham\}$ indicated muscle group. The uncertain functions $\Omega_m^s$ related muscle stimulation intensity and the resulting torque about the joint that the muscle crossed and were modeled as:

$$\Omega_m^s \triangleq \lambda_m^s \eta_m^s \cos(a_m^s), m \in \mathcal{M}, s \in S \quad (203)$$

where $\lambda_m^s \in \mathbb{R}$ denoted the uncertain moment arm of the muscle force about the joint, $\eta_m^s \in \mathbb{R}$ denoted the uncertain nonlinear function relating stimulation intensity to muscle fiber force, and $a_m^s \in \mathbb{R}$ denoted the uncertain pennation angle of the muscle fibers.

Assumption 1. The biarticular effects of the rectus femoris and hamstring muscles were negligible.

Property 1. The moment arms of the muscle groups about their respective joints gym, $\lambda_m^s$, $\forall m \in \mathcal{M}$, $\forall s \in S$, depended on the joint angles and were nonzero, continuously differentiable, and bounded with bounded first time derivatives.

Property 2. The functions relating stimulation voltage to muscle fiber force $\eta_m^s$, $\forall m \in \mathcal{M}$, $\forall s \in S$, were functions of the force-length and force-velocity relationships of the muscle being stimulated and were lower and upper bounded by known positive constants $c_{\eta 1}$, $c_{\eta 2} \in \mathbb{R}^+$ respectively, provided the muscle was not fully stretched or contracting concentrically at its maximum shortening velocity.

Property 3. The muscle fiber pennation angles $$a_m^s \neq \left(n\pi + \frac{\pi}{2}\right), \forall m \in \mathcal{M}, \forall s \in \mathcal{S}, \forall n \in \mathbb{Z} \text{ (i.e., } \cos(a_m^s) \neq 0).$$

Property 4. Based on Properties 1-3, the functions relating voltage applied to the muscle groups and the resulting torques about the joints were nonzero and bounded. In other words, $0 < c_\omega < |\Omega_m^s| \leq c_\Omega \forall m \in \mathcal{M}$, $\forall s \in \mathcal{S}$, where $c_\omega$, $c_\Omega \in \mathbb{R}_{>0}$, were known positive constants.

The Jacobian elements $T_m^s$; were based on the joint torque transfer ratios $T_j^s \in \mathbb{R}$, which were defined as:

$$T_h^s \triangleq -\frac{\partial q_h^s}{\partial q}, T_k^s \triangleq \frac{\partial q_h^s}{\partial q} + \frac{\partial q_k^s}{\partial q}, s \in \mathcal{S} \quad (204)$$

The subscript $j \in \mathcal{J} \triangleq \{h, k\}$ indicated hip (h) and knee (k) joints. From Assumption 1, the torque transfer ratios for the muscle groups, $T_m^s$, were then determined, according to the joint that each muscle spanned, as:

$$T_{glute}^s = T_h^s, T_{quad}^s = T_{ham}^s = T_k^s s \in \mathcal{S} \quad (205)$$

The passive viscoelastic effects of the tissues surrounding the hip and knee joints, denoted by $\tau_p$ in Equation 201, were defined as:

$$\tau_p \triangleq \sum_{j \in \mathcal{J}} \sum_{s \in S} T_j^s \tau_{j,p}^s \quad (206)$$

where $\tau_{j,p}^s \in \mathbb{R}$ denoted resultant torques about the rider's joints from viscoelastic tissue forces, modeled as:

$$\tau_{j,p}^s \triangleq k_{j,1}^s \exp(k_{j,2}^s \gamma_j^s)(\gamma_j^s - k_{j,3}^s) + b_{j,1}^s \tan h(-b_{j,2}^s \dot{\gamma}_j^s) - b_{j,3}^s \dot{\gamma}_j^s \quad (207)$$

for $j \in \mathcal{J}$, $s \in \mathcal{S}$, where $k_{j,i}^s$, $b_{j,i}^s \in \mathbb{R}$ $i \in \{1, 2, 3\}$ were unknown constant coefficients, and $\gamma_j^s \in \mathbb{R}$ denoted the relative hip and knee joint angles, defined as:

$$\gamma_h^s \triangleq q_h^s - q_t + \pi, \gamma_k^s \triangleq q_h^s - q_k^s, s \in \mathcal{S} \quad (208)$$

The viscous crank joint damping term $\tau_b$ was modeled as $\tau_b \triangleq -c\dot{q}$, where $c \in \mathbb{R}_{>0}$, was the unknown, constant damping coefficient.

The equation of motion for the total cycle-rider system with electrical stimulation was obtained by substituting Equations 201 and 202 into Equation 200 as:

$$M\ddot{q} + V\dot{q} + G - \tau_p - \tau_b - \tau_d = \sum_{s \in S} \sum_{m \in M} v_m^s \Omega_m^s T_m^s \quad (209)$$

The model in Equation 209 had the following properties:

Property 5. $c_m \leq M \leq c_M$, where $c_m$, $c_M \in \mathbb{R}_{>0}$, were known constants.

Property 6. $|V| \leq c_v |\dot{q}|$, where $c_v \in \mathbb{R}_{>0}$, was a known constant.

Property 7. $|G| \leq c_G$, where $c_G \in \mathbb{R}_{>0}$, was a known constant.

Property 8. $|\tau_d \tau \leq c_d$, where $c_d \in \mathbb{R}_{>0}$, was a known constant.

Property 9. $|T_j^s| \leq c_T$ $\forall s \in \mathcal{S}$, $j \in J$, where $C_T \in \mathbb{R}_{>0}$, was a known constant.

Property 10. $|\tau_p| \leq c_{p1} + c_{p2} |\dot{q}|$, where $c_{p1}$, $c_{p2} \in \mathbb{R}_{>0}$, were known constants.

Property 11.

$$\frac{1}{2} \dot{M} - V = 0$$

B. Switched System Model

1) Stimulation Pattern Development: The muscle torque transfer ratios $T_m^s$ indicated how each muscle group should be activated to induce forward pedaling. Multiplying the joint torque yielded by a muscle contraction with $T_m^s$ transformed that torque to a resultant torque about the crank. Therefore, if only forward pedaling was desired, then each muscle group was only activated when it yielded a clockwise (with respect to FIG. 13) torque about the crank. In other words, stimulation only activated the quadriceps when $T_{quad}$ was negative, the hamstrings when $T_{ham}$ was positive, and the gluteal muscles when $T_{glute}$ was positive. However, this stimulation pattern included stimulation of the muscle groups for vanishingly small values of $T_m^s$. (e.g., near the so-called dead points of the crank cycle) and therefore activated the muscles inefficiently, in the sense that large values of stimulation and metabolic power output resulted in little power output at the cycle crank. Therefore, to increase FES-cycling efficiency, a muscle group was stimulated only when its torque transfer ratio was sufficiently large. Some evidence suggested that the stimulation interval for each muscle group should be minimized to optimize metabolic efficiency. With these constraints, the stimulation intervals for each muscle group $Q_m^s$ g Q were defined as:

$$Q_{glute}^s \triangleq \{q \in Q | T_{glute}^s(q) > \in_{glute}^s\} \quad (210)$$

$$Q_{quad}^s \triangleq \{q \in Q | -T_{quad}^s(q) > \in_{quad}^s\} \quad (211)$$

$$Q_{ham}^s \triangleq \{q \in Q | T_{ham}^s(q) > \in_{ham}^s\} \quad (212)$$

where $\in_m^s \in \mathbb{R}_{>0}$ were selectable constants. Selection of $\in_m^s$ indicated a user-defined minimum torque transfer ratio required before a muscle group was activated, so that $\in_m^s$ was inversely proportional to the length of a muscle group's stimulation interval. To ensure that $Q_m^s \neq \emptyset$ for each m, it was required that $\in_{glute} < \max(T_{glute})$, $\in_{quad} < \max(-T_{quad})$, and $\in_{ham} < \max(T_{ham}^s)$. The set $Q_c \triangleq \cup_{s \in \mathcal{S}} (\cup_{m \in m} Q_m^s)$ was denoted as the controlled region, e.g., the portion of the crank cycle over which muscles were stimulated. The set $$Q_u \triangleq \frac{Q}{Q_c}$$

was denoted as the uncontrolled region, e.g., the portion of the crank cycle over which no muscles were stimulated. Depending on the kinematic parameters of the cycle and rider, along with the selection of $\in_m^s$, $Q_u$ may be empty, but this Example considered the general case where $Q_u$ was not empty.

2) Switched Control Input: To stimulate the rider's muscle groups according to the stimulation pattern defined by Equations 210-212, the stimulation input to each muscle was switched on and off at appropriate points along the crank cycle. Based on this stimulation pattern, piecewise constant switching signals for each muscle group $\sigma_m^s \in \{0,1\}$ were defined as:

$$\sigma_m^s \triangleq \begin{cases} 1 & \text{if } q \in Q_m^s \\ 0 & \text{if } q \notin Q_m^s \end{cases}, m \in \mathcal{M}, s \in \mathcal{S} \tag{213}$$

Then, the stimulation intensity input to each muscle group $v_m^s$ was defined as:

$$v_m^s \triangleq k_m^s \sigma m_s^u, m \in \mathcal{M}, s \in \mathcal{S} \tag{214}$$

where $u \in \mathbb{R}$ was the subsequently designed control input, and $k_m^s$ were control gains that could be tuned to compensate for the relative strength and effectiveness of each muscle group. Substituting Equations 213 and 214 into Equation 209 yielded the following switched system:

$$M\ddot{q} + V\dot{q} + G - \tau_p - \tau_b - \tau_d = \begin{cases} Bu & \text{if } q \in Q_c \\ 0 & \text{if } q \in Q_u \end{cases} \tag{215}$$

where $B \in \mathbb{R}$ was the discontinuous control effectiveness term, defined as:

$$B \triangleq \sum_{s \in \mathcal{S}} \sum_{m \in \mathcal{M}} k_m^s \sigma_m^s \Omega_m^s T_m^s \tag{216}$$

Property 4 and Equations 210-213 were used to demonstrate that B was zero if and only if the crank was in the uncontrolled region (i.e., $q \in Q_u \Leftrightarrow B=0$). In the controlled regions, B was bounded as:

$$c_{B1} \leq B \leq c_{B2}, q \in Q_c \tag{217}$$

where $c_{B1}, c_{B2} \in \mathbb{R}_{>0}$, were known constants.

Figure 14:
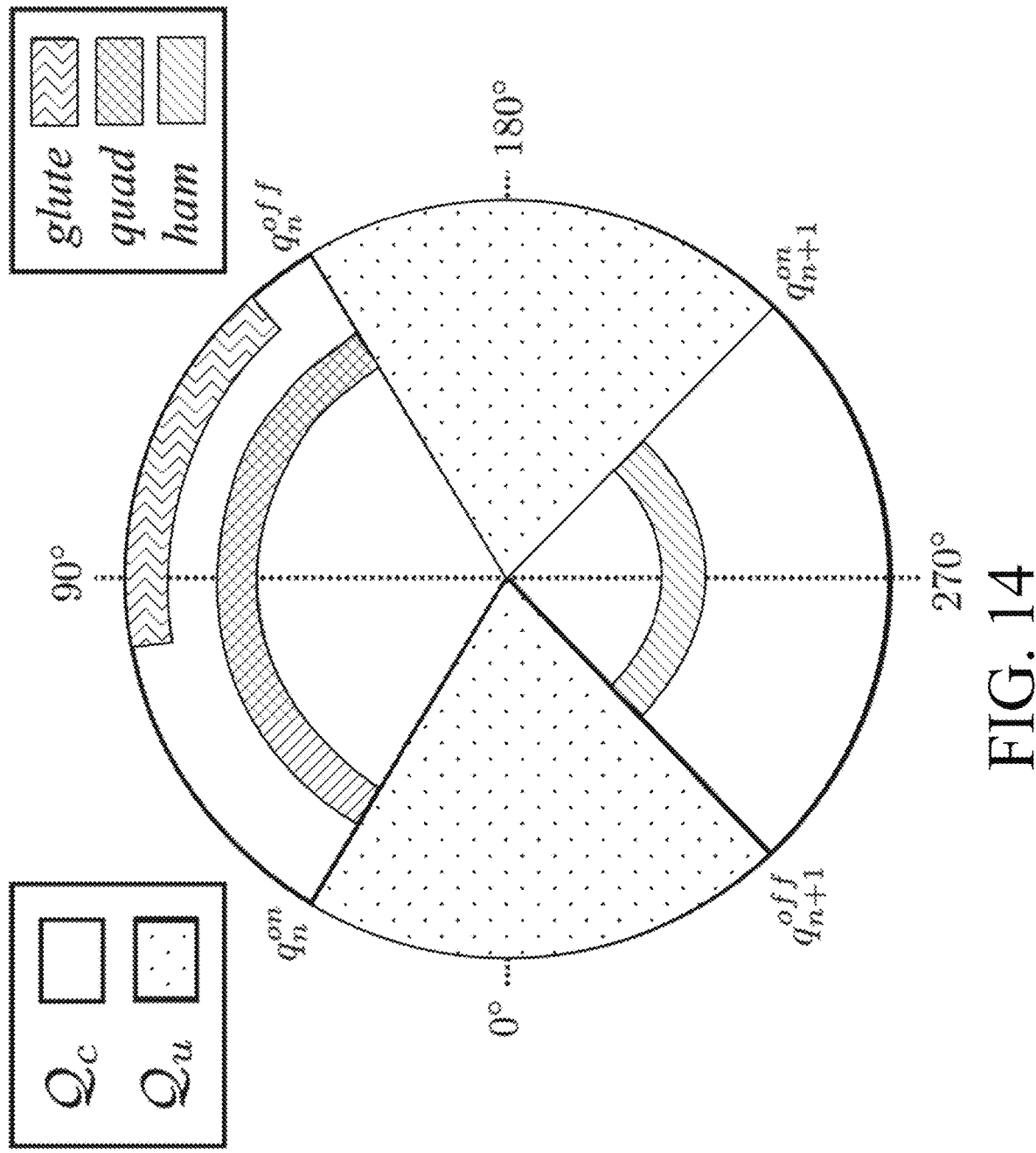
FIG. 14 shows an exemplary stimulation pattern depicting intervals of the crank cycle over which the quadriceps femoris, hamstrings, and gluteal muscle groups of one leg were stimulated, according to some embodiments.

3) Switching States and Times: Assuming that the initial crank angle $q_0^{on}$ was an element of $Q_c$, the known sequence of switching states, which were precisely the limit points of $Q_u$, was defined as $\{q_n^{on}, q_n^{off}\}$, $n \in \{0, 1, 2, \ldots\}$, where the superscripts on and off indicated that the sum of signals a was switching from zero to nonzero or nonzero to zero, respectively. The corresponding sequence of unknown switching times $\{t_n^{on}, t_n^{off}\}$ was defined such that each on-time tr and off-time $t_n^{off}$ denoted the instant when q reached the corresponding on-angle $q_n^{on}$ and off-angle $q_n^{off}$, respectively. FIG. 14 shows an exemplary stimulation pattern and the associated switching states. FIG. 14 shows the intervals of the crank cycle over which the quadriceps femoris, hamstrings, and gluteal muscle groups of one leg were stimulated. In FIG. 14, the crank positions $q_n^{on}$ and $q_n^{off}$ denote the points at which the crank exited or entered, respectively, the uncontrolled region $Q_u$.

III. Control Development

Based on the model in Equation 200, a robust controller was subsequently developed to ensure cadence tracking. The controller did not depend explicitly on the model, as the model was uncertain, but the structure of the model informed the control design. Only the torque transfer ratios $T_m^s$, which depended on the measurable rider's limb lengths and seat position, needed to be known to determine which muscle group to apply the controller to throughout the crank cycle. Known bounds on the other model parameters enabled the robust controller to guarantee tracking despite model uncertainty.

The control objective was to track a desired crank cadence with performance quantified by the tracking error signal $r \in \mathbb{R}$, defined as:

$$r \triangleq \dot{q}_d - \dot{q} \tag{218}$$

where $q_d \in \mathbb{R}$ denoted the desired crank position, designed so that its derivatives existed and $\dot{q}_d, \ddot{q}_d \in \mathcal{L}_\infty$. Without loss of generality, $q_d$ was designed to monotonically increase, i.e., backpedaling was not desired.

Taking the time derivative of Equation 218, multiplying by M, and using Equations 215 and 218 yielded the open-loop error system:

$$M\dot{r} = \chi - Vr - \begin{cases} Bu & \text{if } q \in Q_c \\ 0 & \text{if } q \in Q_u \end{cases} \tag{219}$$

where the auxiliary term $\chi \in \mathbb{R}$ was defined as:

$$\chi \triangleq M\ddot{q}_d + V\dot{q}_d + G - \tau_p - \tau_b - \tau_d \tag{220}$$

Based on Equation 220 and Properties 5-5, $\chi$ was bounded as:

$$|\chi| \leq c_1 + c_2|r| \tag{221}$$

where $c_1, c_2 \in \mathbb{R}_{>0}$ were known constants.

Based on Equation 219 and the subsequent stability analysis, the control input was designed as:

$$u \triangleq k_1 r + k_2 \text{sgn}(r) \tag{222}$$

where sgn (•) denoted the signum function, and $k_1, k_2 \in \mathbb{R}_{>0}$ were constant control gains. After substituting Equation 222 into the open-loop error system in Equation 219, the following switched closed-loop error system was obtained:

$$M\dot{r} = \chi - Vr - \begin{cases} B[k_1 r + k_2 \text{sgn}(r)] & \text{if } q \in Q_c \\ 0 & \text{if } q \in Q_u \end{cases} \tag{223}$$

IV. Stability Analysis $V_L: \mathbb{R} \to \mathbb{R}$ was a positive definite, continuously differentiable, common Lyapunov-like function defined as:

$$V_L \triangleq \frac{1}{2} M r^2 \tag{224}$$

The common Lyapunov-like function $V_L$ was radially unbounded and satisfied the following inequalities:

$$\left(\frac{c_m}{2}\right) r^2 \leq V_L \leq \left(\frac{c_M}{2}\right) r^2 \tag{225}$$

Theorem 1. For $q \in Q_c$, the closed-loop error system in Equation 223 was exponentially stable in the sense that:

$$|r(t)| \leq \sqrt{\frac{c_M}{c_m}} |r(t_n^{on})| e^{-\frac{\lambda_c}{2}(t - t_n^{on})} \; \forall t \in (t_n^{on}, t_n^{off}), \forall n \tag{226}$$

where $\lambda_c \in \mathbb{R}_{>0}$ was defined as:

$$\lambda_c \triangleq \frac{2}{c_M}(k_1 c_{B1} - c_2) \quad (227)$$

provided the following sufficient gain conditions were satisfied:

$$k_1 > \frac{c_2}{c_{B1}}, k_2 \geq \frac{c_1}{c_{B1}} \quad (228)$$

Proof: It can be demonstrated that the time derivative of Equation 224 exists almost everywhere (a.e.), i.e., for almost all $t \in (t_n^{on}, t_n^{off})$, and, after substituting Equation 223, can be upper bounded using Equations 217 and 221 as:

$$\dot{V}_L \leq -(k_2 c_{B1} - c_1)|r| - (k_1 c_{B1} - c_2)r^2 \quad (229)$$

From Equation 217, it can be demonstrated that the inequality in Equation 221 holds for all subsets $Q_m^s$ of the controlled region $Q_c$, so it can be concluded that $V_L$ is a common Lyapunov-like function in the controlled region. Provided the conditions on the control gains in Equation 228 are satisfied, Equation 221 can be used to upper bound Equation 229 as:

$$\dot{V}_L \leq -\lambda_c V_L \quad (230)$$

where $\lambda_c$ was defined in Equation 227. The inequality in Equation 230 can be solved to yield:

$$V_L(t) \leq V_L(t_n^{on})\exp[-\lambda_c(t - t_n^{on})] \quad (231)$$

for all $t \in (tr, t_n^{off})$ and for all n. Rewriting Equation 231 using Equation 225 and performing some algebraic manipulation yields Equation 226.

Remark 1. Theorem 1 guaranteed that the desired cadence could be tracked with exponential convergence, provided that the crank angle did not exit the controlled region. Thus, if the stimulation pattern and desired cadence were designed such that the crank was not required to exit the controlled region, the controller in Equation 222 yielded exponential tracking for all time. If the desired cadence was designed such that the crank must exit the controlled region, the system became uncontrolled. The following theorem details the resulting error system behavior.

Theorem 2. For $q \in Q_u$, the closed-loop error system in Equation 223 could be bounded as:

$$|r(t)| \leq \left\{ \frac{c_M}{c_m} r^2(t_n^{off})\exp[\lambda_u(t - t_n^{off})] + \frac{1}{c_m}\exp[\lambda_u(t - t_n^{off})] - \frac{1}{c_m} \right\}^{\frac{1}{2}} \quad (232)$$

for all $t \in [t_n^{off}, t_{n+1}^{on}]$ and for all n.

Proof: In the uncontrolled region, the time derivative of Equation 224 can be expressed using Equation 223 and Property 5 as:

$$\dot{V}_L = \chi r \quad (233)$$

which can be upper bounded using Equations 221 and 225 as:

$$\dot{V}_L \leq \lambda_u \left(V_L + \frac{1}{2}\right) \quad (234)$$

The solution to Equation 234 over the interval $t \in [t_n^{off}, t_{n+1}^{on}]$ yields the following upper bound on $V_L$ in the uncontrolled region:

$$V_L(t) \leq V_L(t_n^{off})\exp[\lambda_u(t - t_n^{off})] + \frac{1}{2}\{\exp[\lambda_u(t - t_n^{off})] - 1\} \quad (235)$$

for all $t \in [t_n^{off}, t_{n+1}^{on}]$ and for all n. Rewriting Equation 235 using Equation 225 and performing some algebraic manipulation yields 232.

Remark 2. The exponential bound in Equation 232 indicated that in the uncontrolled regions, the error norm was bounded by an exponentially increasing envelope. Since the error norm decayed at an exponential rate in the controlled regions, as described by Equation 226, sufficient conditions for stability of the overall system could be developed based on the exponential time constants $\lambda_c$ and $\lambda_u$ and the time that the crank dwelled in each region (dwell-times) $\Delta t_n^{on} \triangleq t_n^{off} - t_n^{on}$ and $\Delta t_n^{off} \triangleq t_{n+1}^{on} - t_n^{off}$. However, a challenge was that the dwell-time $\Delta t_n^{on}$ and reverse dwell-time $\Delta t_n^{off}$ depended on the switching times, which were unknown a priori. The following assumption introduced bounds on the uncertain dwell-times.

Assumption 2. The dwell-times $\Delta t_n^{on}$ and $\Delta t_n^{off}$ had known, constant bounds for all n such that $$\Delta t_n^{on} \geq \Delta t_{min}^{on}, \Delta t_n^{off} \leq \Delta t_{max}^{off} \quad (236)$$

This assumption was reasonable in the sense that the dwell-time in the controlled and uncontrolled regions will have lower and upper bounds, respectively, provided the cadence remains within predefined limits, and during FES-cycling, it is common to impose such limits for safety reasons.

Remark 3. With known bounds on the time between switches and known rates of convergence and divergence of the tracking error, a known ultimate bound on the tracking error was calculated. The following Theorem gave the value of this ultimate bound along with a sufficient condition for convergence of the tracking error to that bound.

Theorem 3. The closed-loop error system in Equation 223 was ultimately bounded in the sense that $|r(t)|$ converged to a ball with constant radius $d \in \mathbb{R}_{>0}$ as the number of crank cycles approached infinity (i.e., as $n \to \infty$), where d was defined as:

$$d \triangleq \sqrt{\frac{2b}{c_m(1-a)}} \quad (237)$$

and a, $b \in \mathbb{R}_{>0}$ were defined as:

$$a \triangleq \exp(\lambda_u \Delta t_{max}^{off} - \lambda_c \Delta t_{min}^{on}) \quad (238)$$

$$b \triangleq \frac{1}{2}(\exp(\lambda_u \Delta t_{max}^{off}) - 1) \quad (239)$$

provided the following condition were satisfied:

$$\lambda_c > \lambda_u \frac{\Delta t_{max}^{off}}{\Delta t_{min}^{on}} \quad (240)$$

Proof: Using Equations 231 and 235 sequentially and assuming the worst case scenario for each cycle where $\Delta t_n^{on} = \Delta t_{min}^{on}$ and $\Delta t_n^{off} = \Delta_{max}^{off}$, an upper bound for $V_L(t_n^{on})$ after N cycles can be developed as:

$$V_L(t_n^{on}) \leq V_L(t_0^{on})a^N + b\sum_{n=0}^{N-1} a^n \qquad (241)$$

where $N \in \mathbb{N}_{>0}$. The sequence $\{V_L(t_{on}^{on})\}$ is positive, monotonic, and bounded, provided Equation 240 is satisfied (i.e., a<1); therefore, the limit of $\{V_L(t_{on}^{on})\}$ exists and can be expressed as:

$$\lim_{n \to \infty} V_L(t_n^{on}) = \bar{d} \qquad (242)$$

where $\bar{d} \in \mathbb{R}_{>0}$ is a known constant defined as:

$$\bar{d} \triangleq \frac{b}{1-a} \qquad (243)$$

Therefore, $V_L(t_n^{on})$ is ultimately bounded by d in the sense that as $n \to \infty$, $V_L(t_n^{on}) \to \bar{d}$. Monotonicity of the bounds in Equations 231 and 235 can be used to demonstrate that $V_L(t)$ is ultimately bounded by $\bar{d}$. Using Equation 225, it can then be demonstrated that as $n \to \infty$, $|r(t)|$ converges to a ball with constant radius d, where d was defined in Equation 237.

V. Experiments

FES-cycling experiments were conducted with the primary objective of evaluating the performance of the switched controller given in Equation 222 and distributed to the gluteal, quadriceps femoris, and hamstrings muscle groups according to Equation 214. The experiments were divided into Protocol A and Protocol B. The objective of both protocols was to demonstrate the controller's cadence tracking performance in the presence of parametric uncertainty and unmodeled disturbances. The FES-cycling trials were stopped if the control input saturated, the subject reported significant discomfort, the cadence fell below 0 RPM, the trial runtime expired, or the cadence exceeded 60 RPM. The experiments could also be ended at any time by the subjects via an emergency stop switch.

Four able-bodied male subjects 25-27 years old were recruited from the student population at the University of Florida, and one male subject with Parkinson's disease (PD), 60 years old, with a modified Hoehn and Yahr disability score of 2.5, was recruited from the University of Florida Center for Movement Disorders and Neurorestoration. Each subject gave written informed consent approved by the University of Florida Institutional Review Board. Able-bodied subjects were recruited to validate the controller design, and the subject with PD was recruited to demonstrate feasibility of the proposed approach in a potential patient population.

The subject with PD in this experiment exhibited mild bilateral motor impairment with evident tremor. It was observed during preliminary testing that the subject's right side was more affected (i.e., greater tremor) and exhibited bradykinesia during cycling (i.e., when the right leg was supposed to pedal, cadence decreased significantly). It was therefore hypothesized that FES assistance would provide sensory cues and muscle activation assistance during cycling and thereby decrease variability in the subject's cadence.

A commercially available, stationary, recumbent exercise cycle (AudioRider R400, NordicTrack) was modified for the purposes of the FES-cycling experiments. The cycle originally had a flywheel that was driven by a freewheel. The freewheel was then replaced with a fixed gear so that the crankshaft was directly coupled to the flywheel, allowing the flywheel to contribute its momentum to the cycle-rider momentum and improving the system energetics. The cycle had an adjustable seat and a magnetic hysteresis brake on the flywheel with 16 incremental levels of resistance (resistance was set to Level 1 unless otherwise noted). Custom pedals were 3D-printed that allowed hightop orthotic boots (Rebound Air Walker, Össur) to be affixed to them; these orthotic pedals served to fix the rider's feet to the pedals, prevent dorsiflexion and plantarflexion of the ankles, and maintain sagittal alignment of the lower legs. An optical, incremental encoder (HS35F, BEI Sensors, resolution 0.018°) was added to the cycle and coupled to the crank shaft to measure the cycling cadence. The cycle was equipped with a Hall effect sensor and magnet on the crank that provided an absolution position reference once per cycle.

A current-controlled stimulator (RehaStim, Hasomed) delivered biphasic, symmetric, rectangular pulses to the subject's muscle groups via bipolar, self-adhesive electrodes (Axelgaard surface electrodes). A personal computer equipped with data acquisition hardware and software was used to read the encoder signal, calculate the control input, and command the stimulator. Stimulation frequency was fixed at 60 Hz. Stimulation intensity was controlled by fixing the pulse amplitude for each muscle group and controlling the pulse width according to Equation 222. Pulse amplitude was determined for each subject's muscle groups in preliminary testing and ranged from 50-110 mA.

Electrodes were placed over the subjects' gluteal, quadriceps femoris, and hamstrings muscle groups (e.g., according to Axelgaard's electrode placement manual) while subjects were standing upright. Subjects were then seated on the stationary cycle, and their feet were inserted securely into the orthotic pedals. The cycle seat position was adjusted for each subject's comfort while ensuring that hyperextension of the knees could not be achieved while cycling. The subject's hip position relative to the cycle crank axis was measured along with the distance $l_t$ between the subjects' greater trochanters and lateral femoral condyles and the distance $l_t$ between the subjects' lateral femoral condyles and the pedal axes of rotation. These distances were used to calculate the torque transfer ratios for the subjects' muscle groups and to thereby determine the stimulation pattern. The desired crank velocity was defined in radians per second as $$\dot{q}_d \triangleq \frac{5\pi}{3}[1 - \exp(-\phi t)] \qquad (244)$$

where $\phi \in \mathbb{R}_{>0}$, was a selectable constant used to control the acceleration of the desired trajectory and $t_0^{on} = 0$ seconds. The trajectory in Equation 244 ensured that the desired velocity started at zero revolutions per minute (RPM) and smoothly approached 50 RPM. The control gains, introduced in Equations 214 and 222, were tuned to yield acceptable tracking performance for each subject in preliminary testing and ranged as follows: $k_1 \in [70, 150]$, $k_2 \in [7, 15]$, $k_{glute}^s \in [0.5625, 1.125]$, $k_{quad}^s \in [0.9, 1.125]$, $k_{ham}^s \in [0.816, 1.2375]$, $\forall_s \in \mathcal{S}$.

Protocol A was completed by all able-bodied subjects and comprised a voluntary cycling phase followed by five minutes of rest and a subsequent FES-cycling phase. During the voluntary cycling phase, subjects were shown a computer screen with a real-time plot of their actual cadence, as measured by the encoder, versus the desired cadence given in Equation 244, and each subject was asked to voluntarily pedal so that the two plots coincided with one another (i.e., minimize the tracking error r). After 175 seconds had elapsed, the flywheel resistance was increased from Level 1 directly to Level 9 for a period of 30 seconds, after which the resistance was decreased back to Level 1 for the remainder of the cycling phase. The voluntary cycling phase lasted five minutes.

Following five minutes of rest, the FES-cycling phase was initiated, wherein cycling was only controlled by stimulation of the gluteal, quadriceps femoris, and hamstrings muscle groups (i.e., a completely passive rider). The stimulation pattern (i.e., the range of crank angles over which each muscle was stimulated) for Protocol A was defined by selecting $\in_{glute}=0.2$, $\in_{quad}=0.3$, $\in_{ham}=0.38$, which was found to yield satisfactory performance in preliminary testing. While the same values of $\in_m$ were used for all subjects, the stimulation pattern resulting from the choice of each $\in_m$ was slightly different for each subject because each subject had different leg lengths and preferred seating positions. The subjects' limbs were then positioned manually so that the initial crank position was in the controlled region, and then the controller was activated. The subjects were instructed to relax as much as possible throughout this phase and to make no effort to voluntarily control the cycling motion; additionally, the subjects were not given any indication of the control performance (i.e., subjects could no longer see the actual or desired trajectory). As in the voluntary cycling phase, the flywheel resistance was increased from Level 1 to Level 9 for $t\in[175, 205]$ seconds to demonstrate the controller's robustness to an unknown, bounded, time-varying disturbance. The FES-cycling phase lasted five minutes.

Protocol B was completed by the subject with PD and was the same as Protocol A, with the exception that the subject was allowed to voluntarily pedal during the FES cycling phase (i.e., FES-assisted cycling) and could see the actual and desired cadence. While Protocol A was intended to demonstrate the controller's performance with a completely passive rider, as would be the case with a subject with motor complete spinal cord injury, Protocol B demonstrated feasibility of the developed controller for a broader patient population with intact, albeit diminished, motor control, such as those with motor incomplete spinal cord injury, hemiparetic stroke, traumatic brain injury, and Parkinson's disease. From an analytical perspective, voluntary assistance from the rider could be viewed as an unmodeled disturbance and so could be lumped into $\tau_d$ in Equation 215. Although disturbances are generally neither assistive nor resistive, voluntary effort from the rider during FES-cycling is generally assistive and is therefore expected to decrease the control input needed to track the desired cadence.

Protocol a Results

Figure 15:
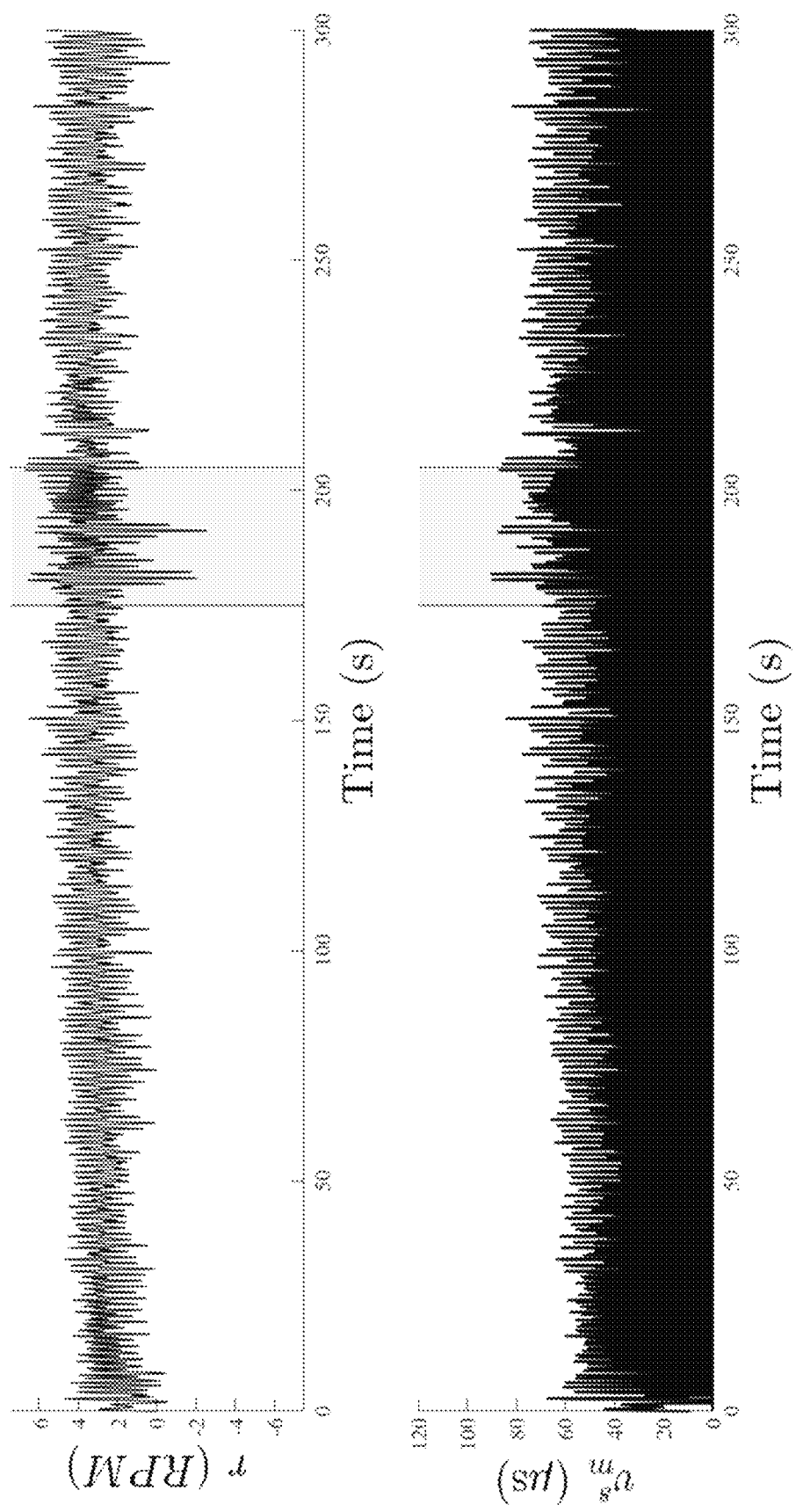
FIG. 15 shows, according to some embodiments, cadence tracking error for a subject during experimental trials (top), and control input to each muscle group (bottom)
Figure 16:
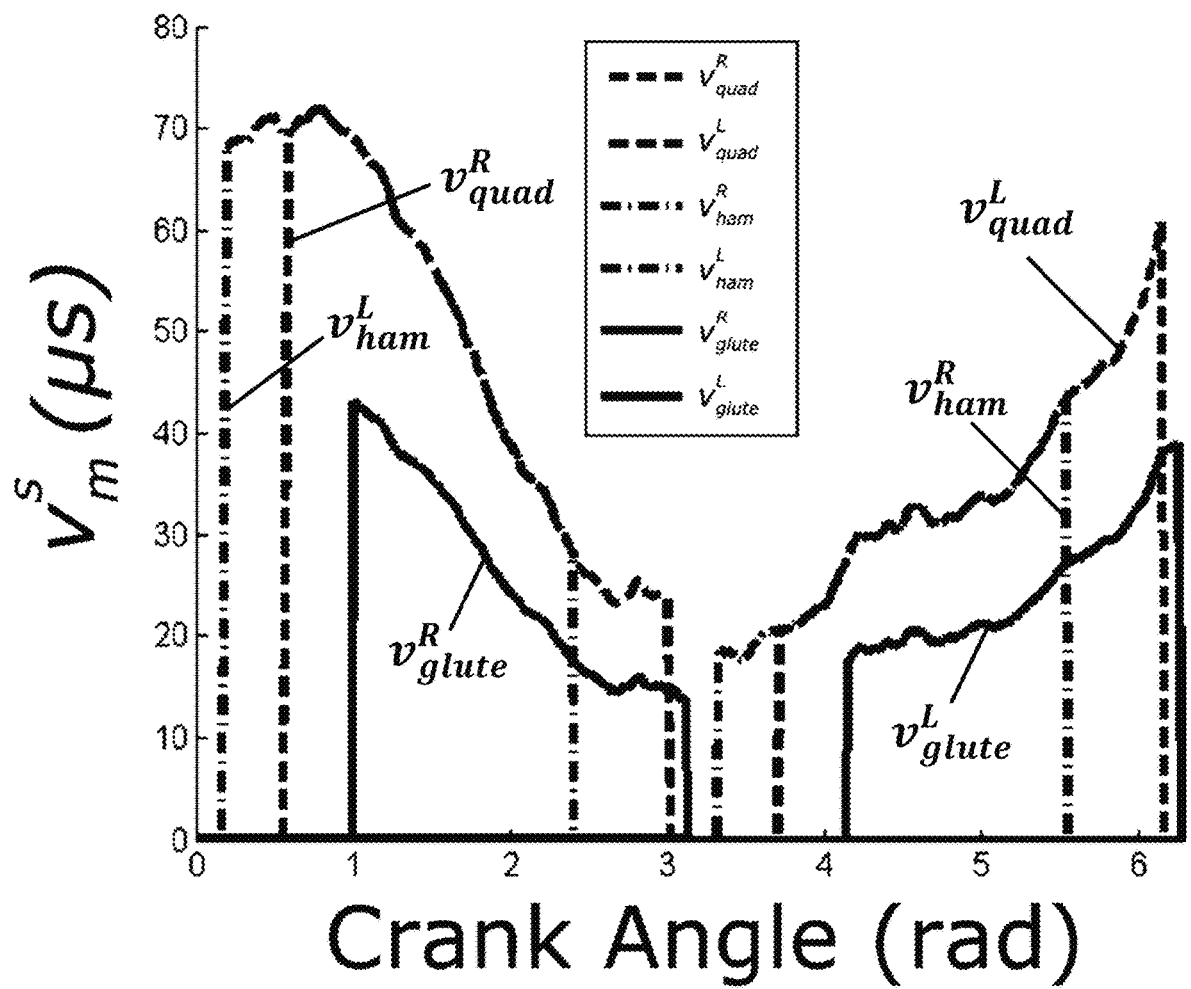
FIG. 16 shows control input over a single crank cycle showing the switching of a controller between the quadriceps femoris, hamstrings, and gluteal muscle groups during an experimental trial, according to some embodiments.
Figure 17:
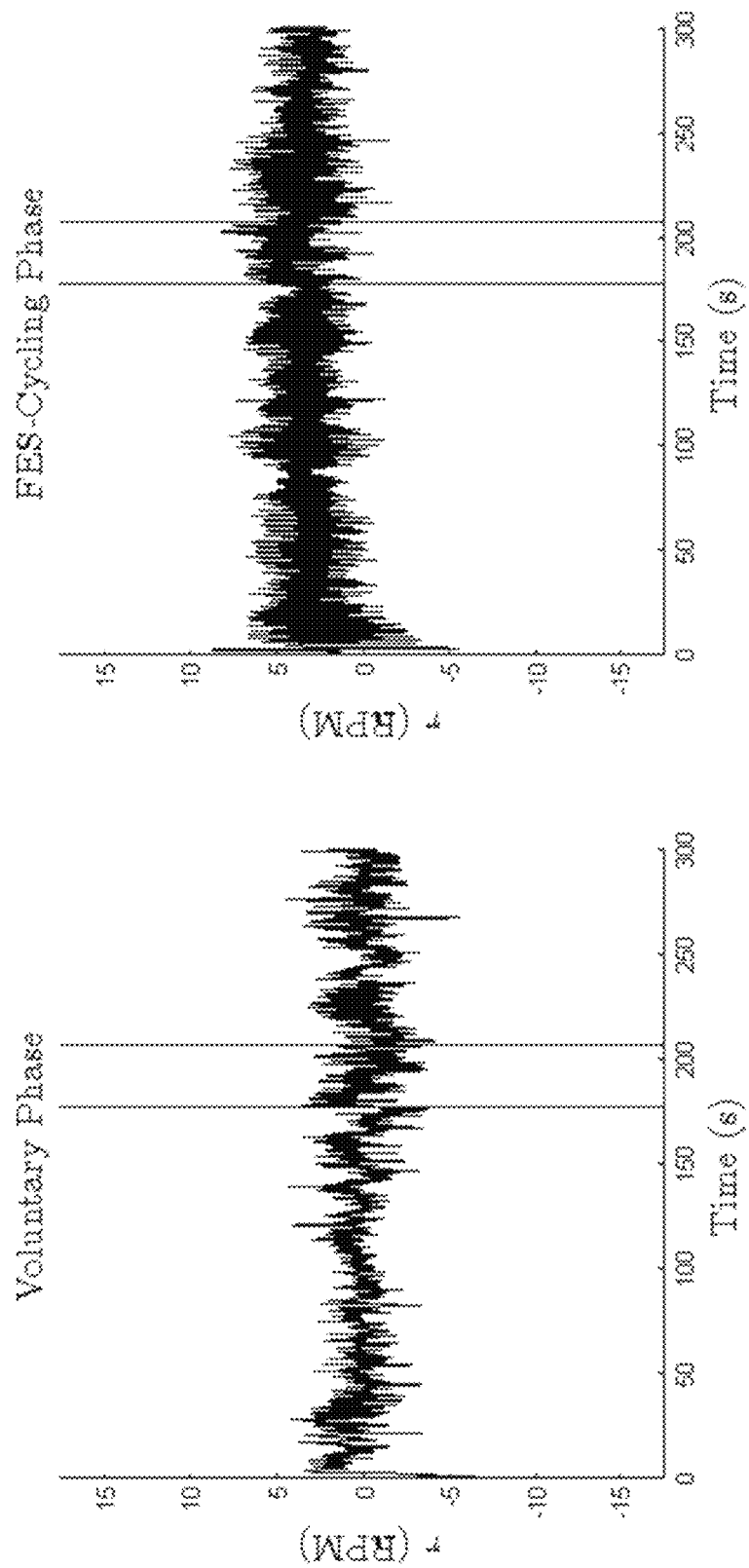
FIG. 17 shows, according to some embodiments, cadence tracking error for an able-bodied subject during voluntary (left) and FES-cycling (right) phases of an experimental trial.

FIG. 15 depicts one subject's tracking performance, quantified by the cadence tracking error r, and the stimulation intensity (pulsewidth) input to each muscle group $v_m^s$ during the FES-cycling phase of Protocol A. FIG. 16 provides an enhanced view of the control input over a single crank cycle to illustrate the controller switching and distribution of the control input across the muscle groups. Table IV compares each subject's volitional and FES-induced tracking performance, quantified by the root mean square mean and standard deviation (st. dev.) of the cadence tracking error in RPM, over the total trial ($t\in[0,300]$ seconds) and during several phases of each trial: the transient phase ($t\in[0,40]$ seconds), the steady state phase ($t\in[40, 175]$ seconds), and the final phase ($t\in[205, 300]$ seconds). FIG. 17 compares another subject's cadence tracking error in the voluntary and FES-induced cycling phases. All trials went to completion.

TABLE IV

| Subject | Phase | Volitional Error (RPM) | FES Error (RPM) |
| --- | --- | --- | --- |
| AB1 | Transient | 1.04 ± 1.58 | 2.41 ± 1.08 |
|  | Steady State | −0.06 ± 1.59 | 3.12 ± 1.04 |
|  | Disturbance | 0.04 ± 2.01 | 3.39 ± 1.61 |
|  | Final | −0.43 ± 1.70 | 3.47 ± 1.21 |
|  | Total Trial | −0.02 ± 1.73 | 3.16 ± 1.22 |
| AB2 | Transient | 0.28 ± 3.26 | 6.03 ± 2.07 |
|  | Steady State | −0.07 ± 1.15 | 9.78 ± 1.58 |
|  | Disturbance | 0.01 ± 1.43 | 14.56 ± 1.78 |
|  | Final | −0.01 ± 1.17 | 12.68 ± 1.21 |
|  | Total Trial | 0.01 ± 1.63 | 10.68 ± 2.92 |
| AB3 | Transient | 0.62 ± 1.68 | 2.31 ± 2.54 |
|  | Steady State | 0.01 ± 1.06 | 3.12 ± 1.70 |
|  | Disturbance | −0.21 ± 1.51 | 4.14 ± 1.52 |
|  | Final | −0.31 ± 1.38 | 3.19 ± 1.63 |
|  | Total Trial | −0.03 ± 1.34 | 3.14 ± 1.85 |
| AB4 | Transient | 1.22 ± 2.72 | 3.51 ± 2.75 |
|  | Steady State | −0.01 ± 1.36 | 3.93 ± 1.78 |
|  | Disturbance | 0.40 ± 1.56 | 4.74 ± 3.52 |
|  | Final | 0.18 ± 1.34 | 4.41 ± 2.97 |
|  | Total Trial | 0.25 ± 1.67 | 4.11 ± 2.57 |

Protocol B Results

Figure 18:
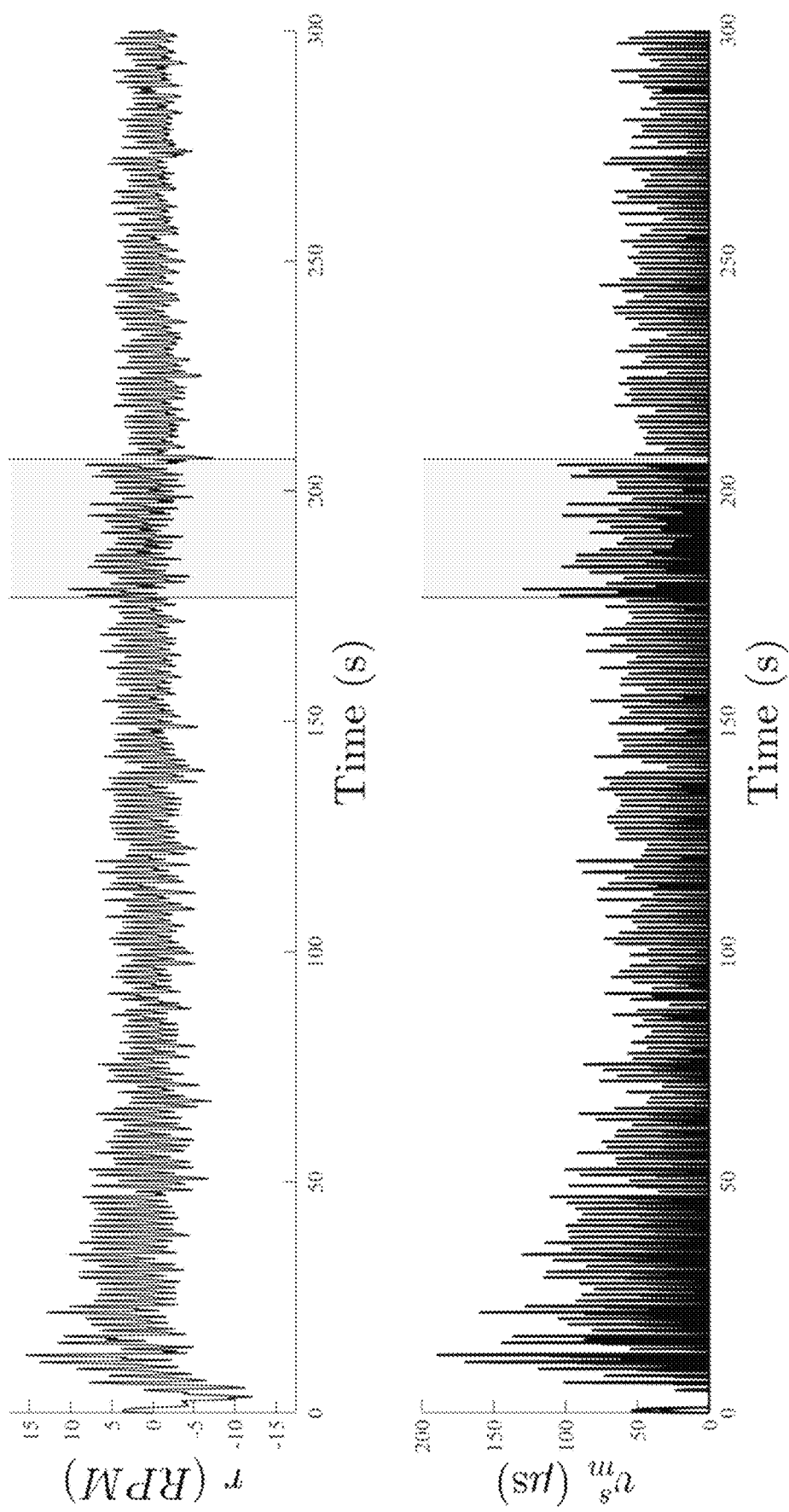
FIG. 18 shows, according to some embodiments, cadence tracking error (top) and control input (bottom) for a subject with Parkinson's disease during an FES-assisted phase of an experimental trial.
Figure 19:
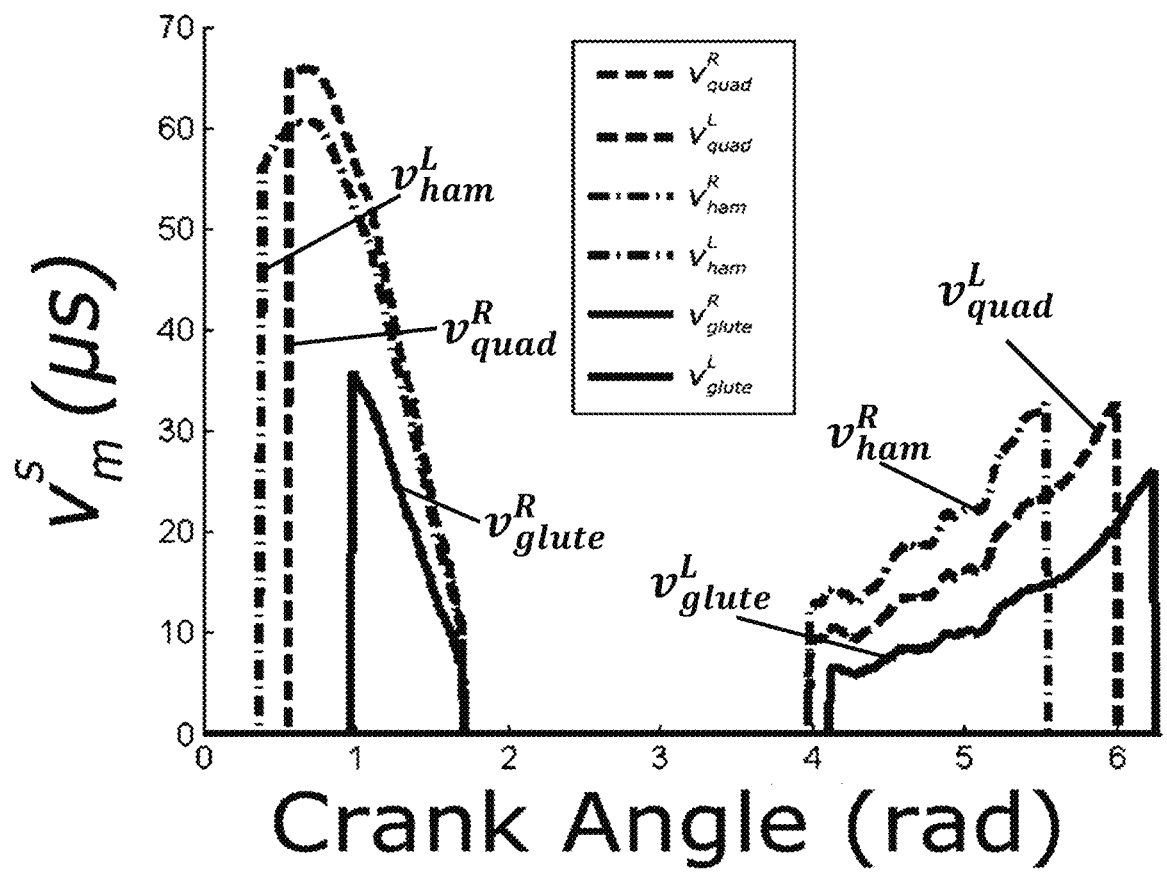
FIG. 19 shows control input over a single crank cycle during an experimental trial, according to some embodiments.
Figure 20:
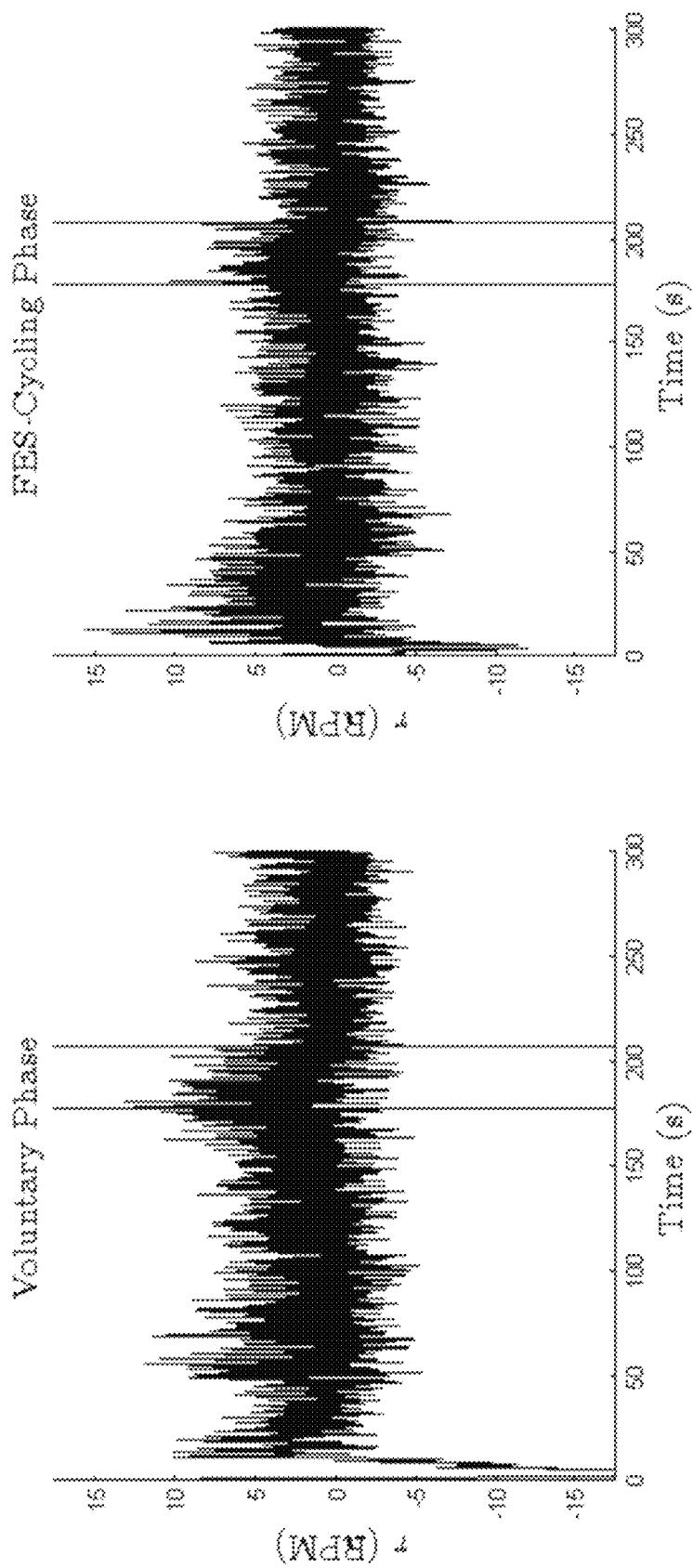
FIG. 20 shows, according to some embodiments, cadence tracking error for a subject with Parkinson's disease during voluntary (left) and FES-assisted (right) phases of an experimental trial.

FIG. 18 depicts the tracking performance of the subject with PD, quantified by the cadence tracking error r, and the stimulation intensity (pulsewidth) input to each muscle group $v_m^s$ during the FES-assisted phase of Protocol B. FIG. 19 provides an enhanced view of the control input over a single crank cycle to illustrate the controller switching and distribution of the control input across the muscle groups. Table V summarizes the volitional and FES assisted cadence tracking performance of the subject with PD using the same metrics as described above in relation to the able-bodied subjects. FIG. 20 compares the subject's cadence tracking error in the voluntary and FES-assisted cycling phases. All trials went to completion.

TABLE V

| Subject | Phase | Volitional Error (RPM) | FES Error (RPM) |
| --- | --- | --- | --- |
| PD | Transient | −1.28 ± 7.41 | 1.28 ± 4.87 |
|  | Steady State | 0.80 ± 3.21 | 0.07 ± 2.82 |
|  | Disturbance | 2.10 ± 3.88 | 1.15 ± 2.91 |
|  | Final | 0.11 ± 2.65 | −0.46 ± 2.32 |
|  | Total Trial | 0.43 ± 4.06 | 0.17 ± 3.11 |

The results of Protocol A successfully demonstrated the ability of the controller in Equation 222, distributed across the muscle groups according to Equation 214, to achieve ultimately bounded tracking of the desired cadence despite parametric uncertainty (e.g., uncertain rider limb mass) and unknown disturbances. Ultimately bounded tracking was achieved even across a range of stimulation patterns. Although the ultimate bound on the tracking error was higher for FES-cycling than volitional cycling by all subjects in Protocol A, this was likely due to the steady state offset in the tracking error and not due to large variations in cycling cadence, as shown in FIG. 17. The cadence tracking error of all able-bodied subjects during voluntary cycling was 0.05±1.59 RPM, and the cadence tracking error of all able-bodied subjects during FES-induced cycling was 5.27±2.14 RPM. The steady state error observed in the FES-cycling phase may have been caused by a lack of adaptation in the FES-cycling controller.

During volitional cycling, riders can learn how to modulate the force output of the muscles involved in cycling to improve tracking performance over time. Therefore, to achieve cadence tracking performance during FES-cycling that is similar to that observed during volitional cycling, motivation arises to use adaptive control methods during the controlled regions. However, this is a challenge because adaptive control methods usually only achieve asymptotic convergence of the tracking error, but stability of a switched system with stable and unstable subsystems can only be guaranteed if the convergence and divergence rates are known (as is the case with exponential convergence, for example).

The results of Protocol B demonstrated the controller's tracking performance despite the presence of an additional unknown disturbance (manifested as volitional effort from the subject with PD). The data given in Table V indicate that the addition of FES assistance to the subject's volitional effort improved cadence tracking performance measurably (60.5% and 23.4% improvement in mean and st. dev. of the cadence tracking error across the total trial). The improvement in tracking performance may have been due to the bias of the stimulation input towards the subject's affected right leg (as depicted in FIG. 19), providing both assistance in activating the appropriate muscle groups and a sensory cue to volitionally pedal faster. The results indicate the potential of FES assistance to improve the ability of a person with PD to pedal at a desired cadence.

VI. Conclusion

An uncertain, nonlinear, time-varying model of a human rider pedaling a stationary cycle by means of FES was developed, and a stimulation pattern for the gluteal, quadriceps femoris, and hamstrings muscle groups was developed based on the system's Jacobian elements. The stimulation pattern, defined in Equations 210-212, was used to distribute the stimulation control input to the muscle groups, switching the muscle groups on and off according to the crank angle. Therefore, the system was further modeled as a switched control system with autonomous, state-dependent switching with uncertain switching times. A common Lyapunov-like function was used to prove that the developed controller, given in Equation 222, yielded ultimately bounded tracking of a desired cadence (i.e., crank velocity), provided the desired cadence, control gains, and stimulation pattern satisfied sufficient conditions. Experiments were conducted on four able-bodied subjects, and the results demonstrated both the robustness and stability of the developed switched controller. Experiments were also conducted on one subject with Parkinson's disease, and the results suggest that FES-assisted cycling using the developed switched controller may improve the ability of people with PD to track a desired cadence.

Example 3

This Example describes a model for FES-cycling with electric motor assistance that included the effects of a switched control input and unknown disturbances.

During cycling induced by functional electrical stimulation, various muscle groups are stimulated according to the cycle crank angle; however, because of kinematic constraints on the cycle-rider system, stimulation is typically only applied in a subsection of the crank cycle. Therefore, these systems can be considered as switched control systems with autonomous, state-dependent switching with potentially unstable modes. However, no previous studies considered the effects of switched control in the stability analysis of a motorized functional electrical stimulation cycling system. In this Example, a model of a motorized cycle-rider system with functional electrical stimulation was developed that included the effects of a switched control input. A novel switching strategy for the electric motor was designed to only provide assistance in the regions of the crank cycle where the kinematic effectiveness of the rider's muscles was low. A switched sliding-mode controller was designed, and global, exponentially stable tracking of a desired crank trajectory was guaranteed via Lyapunov methods for switched systems, despite parametric uncertainty in the nonlinear model and unknown, time-varying disturbances. Experimental results from five able-bodied, passive riders validated the control design, and the developed control system achieved an average cadence tracking error of −0.02±4.76 revolutions per minute for a desired trajectory of 50 revolutions per minute.

Autonomous systems designed for rehabilitation and functional assistance for people with disabilities such as paralysis have the potential to maximize rehabilitative outcomes and improve the quality of life for millions of people. Disorders such as paralysis drastically reduce a person's ability to complete tasks due to a loss of neuromuscular control. Functional electrical stimulation can activate paralyzed muscles, restoring functional ability through automated application of electric current to the neuromuscular system, and, when applied to a task such as cycling, can be both rehabilitative and empowering. However, cycling induced by functional electrical stimulation is limited by the capability of the rider's muscles, so an electric motor may be added to accommodate the rider's ability and to support stability. The response by muscle to electrical stimulation is uncertain, time-varying, and nonlinear, and switching the control input across multiple muscle groups and between the rider and an electric motor make guaranteeing stability and performance challenging.

I. Introduction

Rehabilitative and assistive robotics focus on the design of autonomous systems to accommodate varying levels of functional ability for people with disabilities caused by injury or disease, either during a rehabilitative task or an activity of daily living. Rehabilitative robots typically enable people to perform a repetitive, therapeutic activity that they otherwise could not successfully perform (e.g., locomotor training for people with neurological disorders), while assistive robots enable people to perform activities of daily living outside of a rehabilitative setting (e.g., walking outdoors). These systems should be designed to provide assistance in the regions of the task space where the human is functionally disabled, and should only provide input as needed to maximize efficiency and to ensure the human's participation in completing the task. Such human-centered autonomous systems have the potential to maximize therapeutic outcomes and enhance the quality of life for people with disabilities.

Paralysis is an example of a functional disability that rehabilitative and assistive robotic systems seek to mitigate. Autonomous systems that aid people with paralysis provide substitutionary motor control, typically via a system of artificial actuators (e.g., electric motors, hydraulic pistons) in the form of a robotic exoskeleton or via functional electrical stimulation (FES), which activates paralyzed muscles by directing electric current into the neuromuscular complex and artificially inducing muscle contractions. When FES is used to induce cycling as a functional activity, it can be both rehabilitative and assistive. When an able-bodied individual cycles volitionally, the rider's leg muscles contract rhythmically to produce a pedaling motion. Meanwhile, paralyzed riders are unable to activate and coordinate their muscles to achieve cycling. FES-cycling systems have been designed to stimulate paralyzed muscles according to a predefined stimulation pattern to enable cycling. Stimulation patterns are designed in the joint space for cycling and include mappings from the crank position and velocity (cadence) to activation signals for each of the rider's muscle groups. Within the joint space are kinematic dead points, where only a small percentage of torque produced by the rider's muscles translates to torque about the crank axis. Stimulation patterns are typically designed such that FES is not applied in regions about these dead points. With such stimulation patterns, the nonlinear, uncertain FES-cycling systems become switched control systems with autonomous, state-dependent switching and unstable modes.

FES-cycling systems that include electric motor assistance have been designed to facilitate controllability, as an electric motor has control authority across the entire joint space (i.e., not limited by dead points). However, none of the previous works considered the effects of the switching stimulation pattern on the motorized FES-cycling system's stability. Furthermore, all of the previous studies used the motor throughout the entire crank cycle, which may bias the control input towards the motor, potentially limiting the contribution from the rider's muscles and thereby limiting the therapeutic effects of the activity. Designing switched FES control systems with electric motor assistance that account for these factors may lead to more effective rehabilitative and assistive systems.

A model of the motorized FES-cycling system is presented that includes the effects of switching the control input between an electric motor and FES of multiple muscle groups during cycling. Motivated by the desire to maximize the contribution of the rider's muscles, a novel strategy for electric motor assistance was developed that only provided control input in the regions around the dead points where no FES control input was provided. Based on this model, a switched, sliding-mode controller was developed for both the FES and the motor that yielded global, exponentially stable tracking of a desired crank trajectory, despite the switching effects, uncertainty in the system parameters, and the presence of unknown, bounded disturbances. Experimental results with five able-bodied subjects validated the controller and demonstrated practical application of the theoretical insights.

A. Motorized Cycle-Rider System

A motorized cycle-rider system was modeled as $$M\ddot{q} + V\dot{q} + G - \tau_p - \tau_b - \tau_d = \sum_{m \in \mathcal{M}} B_m u_m + B_e u_e \quad (245)$$

where $q \in Q \subset \mathbb{R}$ denoted the crank angle; $M \in \mathbb{R}$ denoted inertial effects, $V \in \mathbb{R}$ represented centripetal and Coriolis effects, $G \in \mathbb{R}$ represented gravitational effects, $T \in \mathbb{R}$ denoted the torque applied about the crank axis by passive viscoelastic tissue forces, $\tau_b \in \mathbb{R}$ denoted the torque applied about the crank axis by viscous crank joint damping, and $\tau_d \in \mathbb{R}$ denoted the torque applied about the crank axis by disturbances (e.g., spasticity or changes in load); $B_M \in \mathbb{R}$ denoted the control effectiveness for the electrically stimulated muscle group with subscript $m \in \mathcal{M} \triangleq$ {RGlute, RQuad, RHam, LGlute, LQuad, LHam} indicating the right (R) and left (L) gluteal (Glute), quadriceps femoris (Quad), and hamstrings (Ham) muscle groups; $u_m \in \mathbb{R}$ denoted the electrical stimulation intensity applied to each muscle group; $B_e \in \mathbb{R}$ was a constant relating the current in the electric motor's windings to the resulting torque about the crank axis; and $u_e \in \mathbb{R}$ was the control current applied to the electric motor windings.

The passive viscoelastic effects of the tissues surrounding the hip and knee joints were expressed as:

$$\tau_p \triangleq \sum_{j \in \mathcal{J}} T_j \tau_{j,p} \quad (246)$$

where $T_j \in \mathbb{R}$ were the joint torque transfer ratios with subscript $j \in \mathcal{J} \triangleq$ {RHip, RKnee, LHip, LKnee} indicating right and left hip and knee joints, and $\tau_{j,p} \in \mathbb{R}$ denoted the resultant torque about the rider's joint from viscoelastic tissue forces. The joint torque transfer rations were defined as:

$$T_{*Hip} \triangleq -\frac{\partial q_{*Hip}}{\partial q}, \quad T_{*Knee} \triangleq \frac{\partial q_{*Hip}}{\partial q} + \frac{\partial q_{*Knee}}{\partial q} \quad (247)$$

where the notation * indicated an ipsilateral property (i.e., a relationship between *Hip and *Knee held for RHip and RKnee as well as LHip and LKnee). $\tau_{j,p}$ were modelled as:

$$\tau_{j,p} \triangleq k_{j,1} \exp(k_{j,2}\gamma_j)(\gamma_j - k_{j,3}) + b_{j,1} \tan h(-b_{j,2}\dot{\gamma}_j) - b_{j,3}\dot{\gamma}_j \quad (248)$$

for $j \in J$, where $k_{j,i}$, $b_{j,i} \in \mathbb{R}$, $i \in \{1, 2, 3\}$ were unknown constant coefficients, and $\gamma_1 \in \mathbb{R}$ denoted the relative hip and knee joint angles, defined as:

$$\gamma_{*Hip} \triangleq q_{*Hip} - q_t + \pi, \gamma_{*Knee} \triangleq q_{*Hip} - q_{*Knee} \quad (249)$$

where $q_t \in \mathbb{R}$ was the measurable, constant trunk angle.

The control effectiveness for each muscle group was defined as:

$$B_m \triangleq \Omega_m T_m \quad (250)$$

where $\Omega_m \in \mathbb{R}$ denoted the relationship between stimulation intensity and a muscle group's resultant torque about the joint it spanned, and $\tau_m \in \mathbb{R}$ denoted the torque transfer ratio for a muscle group, which was determined according to the primary joint that each muscle group spanned as $T^*_{Glute} = \tau_{*Hip}$, $T_{*Quad} = T_{*Ham} = T_{*Knee}$, given that the following assumption held.

Assumption 1. The biarticular effects of the rectus femoris and hamstring muscles were negligible.

The uncertain function $\Omega_m$ was modeled as:

$$\Omega_m \triangleq \lambda_m \eta_m \cos(a_m) \quad (251)$$

for $m \in \mathcal{M}$, where $\Delta_m \in \mathbb{R}$ denoted the uncertain moment arm of a muscle's output force about the joint it spanned, $\eta_m \in \mathbb{R}$ denoted the uncertain nonlinear function relating stimulation intensity to muscle fiber force, and $a_m \in \mathcal{M}$ denoted the uncertain pennation angle of the muscle fibers.

Property 1. The moment arm of the muscle group about the joint it spanned $\lambda_m^s$, $\forall m \in \mathcal{M}$, depended on the joint angle and was nonzero, and continuously differentiable with a bounded first time derivative.

Property 2. The function relating stimulation voltage to muscle fiber force, $\eta_m^s$, $\forall m \in \mathcal{M}$, depended on the force-length and force-velocity relationships of the muscle being stimulated and was lower and upper bounded by known positive constants $c_{\eta_1}$, $c_{\eta_2} \in \mathbb{R}^+$, respectively, provided the muscle was not fully stretched or contracting concentrically at its maximum shortening velocity.

Property 3. The muscle fiber pennation angle $$a_m \neq \left(n\pi + \frac{\pi}{2}\right), \forall m \in \mathcal{M}^*, \forall n \in \mathbb{Z} \text{ (i.e., } \cos(a_m^s) \neq 0\text{)}.$$

Property 4. Based on Properties 1-3, the function relating voltage applied to a muscle group and the resulting torque about the joint was nonzero and bounded. In other words, $0 < c_\omega < |\Omega_m| \leq c_\Omega \forall m \in \mathcal{M}$, where $c_\omega$, $c_\Omega \in \mathbb{R}_{>0}$, were known positive constants.

The control effectiveness for the electric motor was defined as $B_e \triangleq K_\tau r_g$, where $K_\tau \in \mathbb{R}_{>0}$, was the uncertain, constant coefficient relating armature current to torque, and $r_g \in \mathbb{R}_{>0}$, was the uncertain gear ratio between the motor output and the crank axis. It was assumed that $0 < c_e \leq B_e$, where $c_e \in \mathbb{R}_{>0}$, was a known constant.

B. Switched System Model

The control input was generated by stimulation of the muscle groups or by an electric motor. A common question that arises in human-machine interaction is: How should the person's effort be balanced with the machine to accomplish a task cooperatively? In this case, the person's effort is the electrically stimulated muscle input and the machine's is the electric motor input. For FES-cycling, stimulation is typically applied to each muscle group in a predefined region of the crank cycle where the muscles can contribute to the forward pedaling motion, and the muscles are not stimulated in regions of relatively low kinematic effectiveness (i.e., where the torque transfer ratios are small). On the other hand, an electric motor coupled to the crank shaft is able to provide consistent input throughout the entire crank cycle. In a rehabilitative setting, it is preferred that the muscles exert as much work to complete the cycling task as possible to maximize therapeutic effect; therefore, motivation arises to activate the electric motor only as needed. In the present Example, the human-machine effort was balanced by only activating the muscle groups where they could effectively contribute to pedaling and activating the electric motor everywhere else. Switching the control input in this manner yielded an autonomous, state-dependent, switched control system.

The portion of the crank cycle over which a particular muscle group was stimulated was denoted $Q_m \subset Q$ for $m \in \mathcal{M}$. Similarly, the portion of the crank cycle over which the electric motor actively contributed torque was denoted $Q_e \subset Q$. $Q_m$ was defined for each muscle group as:

$$Q_{*Glute} \triangleq \{q \in Q | T_{*Glute}(q) > \in_{*Glute}\} \quad (252)$$

$$Q_{*Quad} \triangleq \{q \in Q | -T_{*Quad}(q) > \in_{*Quad}\} \quad (253)$$

$$Q_{*Ham} \triangleq \{q \in Q | T_{*Ham}(q) > \in_{*Ham}\} \quad (254)$$

where $\in_m \in (0, \max(T_m)]$ was a time-varying signal defined for $m \in \mathcal{M}$. Defining the stimulation regions as in Equations 252-254 limited stimulation to portions of the crank cycle where the ratio of the torque produced by stimulation of the muscle group and the resultant torque about the crank axis was bounded below by $\in_m$, which was designed a priori, and prevented backpedaling, as the muscle groups were only stimulated when the resultant torque about the crank axis was positive (i.e., forward pedaling). A negative sign was included in Equation 253 because knee extensor torque was defined to be negative. $Q_e \triangleq Q \backslash Q_{FES}$, where $Q_{FES} \triangleq \cup_{m \in m} Q_m$; in other words, the electric motor provided control input where the muscle groups did not. Based on these switching laws, a piecewise constant switching signal was developed for each muscle group, $u_m \in \{0, 1\}$, and for the electric motor, $\sigma_e \in \{0, 1\}$, as:

$$\sigma_m \triangleq \begin{cases} 1 & \text{if } q \in Q_m \\ 0 & \text{if } q \notin Q_m \end{cases}, \quad (255)$$

$$\sigma_e \triangleq \begin{cases} 1 & \text{if } q \in Q_e \\ 0 & \text{if } q \notin Q_e \end{cases}$$

Using these state-dependent switching signals, the stimulation input to the muscle groups and the current input to the motor windings was defined as:

$$u_m \triangleq k_m \sigma_m u, u_e \triangleq k_e \sigma_e u \quad (256)$$

where $k_m$, $K_e \in \mathbb{R}_{>0}$, $m \in \mathcal{M}$ were positive, constant control gains, and $u \in \mathbb{R}$ was the subsequently designed control input. Substituting Equation 256 into Equation 245 and rearranging terms yielded:

$$M\ddot{q} + V\dot{q} + G - \tau_p - \tau_b - \tau_d = B_\sigma u \quad (257)$$

where $B_\sigma \in \mathbb{R}_{>0}$ was the lumped, switched control effectiveness term defined as:

$$B_\sigma \triangleq \sum_{m \in M} B_m k_m \sigma_m + B_e k_e \sigma_e. \quad (258)$$

Given the definitions in Equations 252-256, there were up to 28 different subsystems (i.e., $B_\sigma$ could switch up to 28 times over a crank cycle). An auxiliary switching signal was defined as $\sigma \in \mathcal{P} \triangleq \{1, 2, 3, \ldots, 28\}$, where the first 27 subsystems represented some combination of active muscle groups and the 28$^{th}$ represented only electric motor activation. The switching signal $\sigma$-specified the index of $B_\sigma$ and switched according to the crank position. For example, if only the right and left quadriceps femoris muscle groups were stimulated according to Equation 253 and the electric motor was activated elsewhere, there would be only three subsystems, and $\sigma$ would be defined as $$\sigma \triangleq \begin{cases} 1, & \text{if } q \in Q_{RQuad} \\ 2, & \text{if } q \in Q_{LQuad} \\ 3, & \text{if } q \in Q_e \end{cases} \quad (259)$$

The known sequence of switching states, which were the limit points of $Q_m$, $\forall m \in \mathcal{M}$, was defined as $\{q_n\}, n \in \{0, 1, 2, \ldots\}$, and the corresponding sequence of unknown switching times $\{t_n\}$ was defined such that each $t_n$ denoted the instant when q reached the corresponding switching state q. The switching signal σ was assumed to be continuous from the right (i.e., $\sigma(q)=\lim_{q \to q_{n+}} \sigma(q)$). The switched system in Equation 257 had the following properties.

Property 5. $c_m \leq M \leq c_M$, where $c_m$, $c_M \in \mathbb{R}_{>0}$ were known constants.

Property 6. $|V| \leq c_v |\dot{q}|$, where $c_v \in \mathbb{R}_{>0}$ was a known constant.

Property 7. $|G| \leq c_G$, where $c_G \in \mathbb{R}_{>0}$ was a known constant.

Property 8. $|\tau_d| \leq c_{p1} + c_{p2}|\dot{q}|$, where $c_{p1}$, $c_{p2} \in \mathbb{R}_{>0}$ were known constants.

Property 9. $|T_j^s| \leq c_T$ $\forall s \in \mathcal{S}$, $j \in \mathcal{J}$, where $C_T \in \mathbb{R}_{>0}$ was a known constant.

Property 10. $|\tau_p| \leq C_{p1} + c_{p2}|\dot{q}|$, where $c_{p1}$, $c_{p2} \in \mathbb{R}_{>0}$ were known constants.

Property 11.

$$\frac{1}{2}\dot{M} - V = 0$$

III. Control Development

The control objective was to track a desired crank trajectory with performance quantified by the tracking error signals $e_1$, $e_2 \in \mathbb{R}$, defined as:

$$e_1 \triangleq q_d - q \tag{260}$$

$$e_2 \triangleq \dot{e}_1 + \alpha e_1 \tag{261}$$

where $q_d \in \mathbb{R}$ was the desired crank position, designed so that its derivatives existed and $\dot{q}_d$, $\ddot{q}_d \in \mathcal{L}_\infty$, and $\alpha \in \mathbb{R}_{>0}$, was a selectable constant. Without loss of generality, $q_d$ was designed to monotonically increase (i.e., backpedaling was not desired). Taking the time derivative of Equation 261, multiplying by M, and using Equations 257-261 yielded:

$$M\dot{e}_2 = \chi - e_1 - Ve_2 - B_\sigma u, \tag{262}$$

where the auxiliary term $\Omega \in \mathbb{R}$ was defined as:

$$\chi \triangleq M(\ddot{q}_d + \alpha \dot{e}_1) + V(\dot{q}_d + \alpha e_1) + G - \tau_p - \tau_b - \tau_d + e_1 \tag{263}$$

From Properties 5-10, x was bounded as:

$$|\chi| \leq c_1 + c_2\|z\| + c_3\|z\|^2 \tag{264}$$

where $c_1$, $c_2$, $c_3 \in \mathbb{R}_{>0}$, were known constants, $\|\cdot\|$ denoted the Euclidean norm, and the error vector $z \in \mathbb{R}^2$ was defined as:

$$z \triangleq [e_1 e_2]^T \tag{265}$$

Based on Equation 262 and the subsequent stability analysis, the control input was designed as:

$$u \triangleq k_1 e_2 + (k_2 + k_3\|z\| + k_4\|z\|^2)\text{sgn}(e_2) \tag{266}$$

where sgn (•) denoted the signum function and $k_1$, $k_2$, $k_3$, $k_4 \in \mathbb{R}_{>0}$, were constant control gains. Substituting Equation 266 into Equation 262 yielded:

$$M\dot{e}_2 = \chi - e_1 - Ve_2 - B_\sigma[k_1 e_2 + (k_2 + k_3\|z\| + k_4\|z\|^2)\text{sgn}(e_2)] \tag{267}$$

IV. Stability Analysis $V_L: \mathbb{R}^2 > \mathbb{R}$ denoted a continuously differentiable, positive definite, common Lyapunov function candidate defined as:

$$V_L \triangleq \frac{1}{2}e_1^2 + \frac{1}{2}Me_2^2 \tag{268}$$

The common Lyapunov function candidate $V_L$ satisfied the following inequalities:

$$\lambda_1\|z\|^2 \leq V_L \leq \lambda_2\|z\|^2 \tag{269}$$

where $\lambda_0$, $\Delta_2 \in \mathbb{R}_{>0}$ were known constants defined as:

$$\lambda_1 \triangleq \min\left(\frac{1}{2}, \frac{c_m}{2}\right), \tag{270}$$

$$\lambda_2 \triangleq \max\left(\frac{1}{2}, \frac{c_M}{2}\right)$$

Theorem 1. The closed-loop error system in Equation 267 was globally, exponentially stable in the sense that:

$$\|z\| \leq \sqrt{\frac{\lambda_2}{\lambda_1}}\|z(t_0)\|e^{-\frac{1}{2}\lambda_s(t-t_0)} \tag{271}$$

for all $t \in [t_0, \infty)$, where $t_0 \in \mathbb{R}_{>0}$ was the initial time, and $\lambda_s \in \mathbb{R}_{>0}$ was defined as:

$$\lambda_s \triangleq \frac{1}{\lambda_2}\min(\alpha, c_{B1}k_1) \tag{272}$$

provided the following gain conditions were satisfied:

$$k_2 > \frac{c_1}{c_{B1}}, \tag{273}$$

$$k_3 \geq \frac{c_2}{c_{B1}},$$

$$k_4 \geq \frac{c_3}{c_{B1}}$$

Proof: Consider $\sigma = p$ for some arbitrary $p \in \mathcal{P}$ such that $B_p$ is continuous. Because of the signum function in u, the time derivative of Equation 268 exists almost everywhere (a.e.), i.e., for almost all $t \in [t_1 t_{n+1})$, $n \in \{0, 1, 2, \ldots\}$. Therefore, after substituting Equation 267, utilizing Property 12, and rearranging terms, the time derivative of Equation 268 can be expressed as:

$$\dot{V}_L = \dot{e}_1 e_1 - e_1 e_2 + \chi e_2 - B_p k_1 e_2^2 - B_p(k_2 + k_3\|z\| + k_4\|z\|^2)\text{sgn}(e_2)e_2 \tag{274}$$

Using Equations 261 and 264, and Property 11, it can be demonstrated that:

$$\dot{V}_L \leq -\alpha e_1^2 - c_{B1}k_1 e_2^2 + (c_{B1}k_2 - c_1)|e_2| + (c_{B1}k_3 - c_2)\|z\||e_2| - (c_{B1}k_4 - c_3)\|z\|^2|e_2| \tag{275}$$

Provided the gain conditions in Equation 273 are satisfied, Equation 269 can be used to rewrite Equation 275 as:

$$\dot{V}_L \leq \lambda_s V_L \tag{276}$$

where $\Delta_s$ was defined in Equation 272. The inequality in Equation 276 can be rewritten as $$e^{\lambda_s(t-t_n)}(\dot{V}_L + \lambda_s V_L) \leq 0 \tag{277}$$

for $t \in [t_1 t_{n+1})$, which is equivalent to the following expression:

$$\frac{d}{dt}(V_L e^{\lambda_s(t-t_n)}) \leq 0. \tag{278}$$

Taking the Lebesgue integral of Equation 278 and recognizing that the integrand on the left-hand side is absolutely continuous allows the Fundamental Theorem of Calculus to be used to yield:

$$V_L \leq V_L(t_n) e^{-\lambda_s(t-t_n)} \quad (279)$$

for $t \in [t_n, t_{n+1})$.

Since Equation 279 was proven to hold for an arbitrary $\sigma$, Equation 279 holds for all $\sigma \in \mathcal{P}$. Therefore, $V_L$ is indeed a common Lyapunov function, and Equation 279 holds for all $t \in [t_0, \infty)$. In other words, $$V_L \leq V_L(t_n) e^{-\lambda_s(t-t_0)} \quad (280)$$

Using Equation 269 to bound Equation 280 and performing some algebraic manipulation yields Equation 271.

Figure 21:
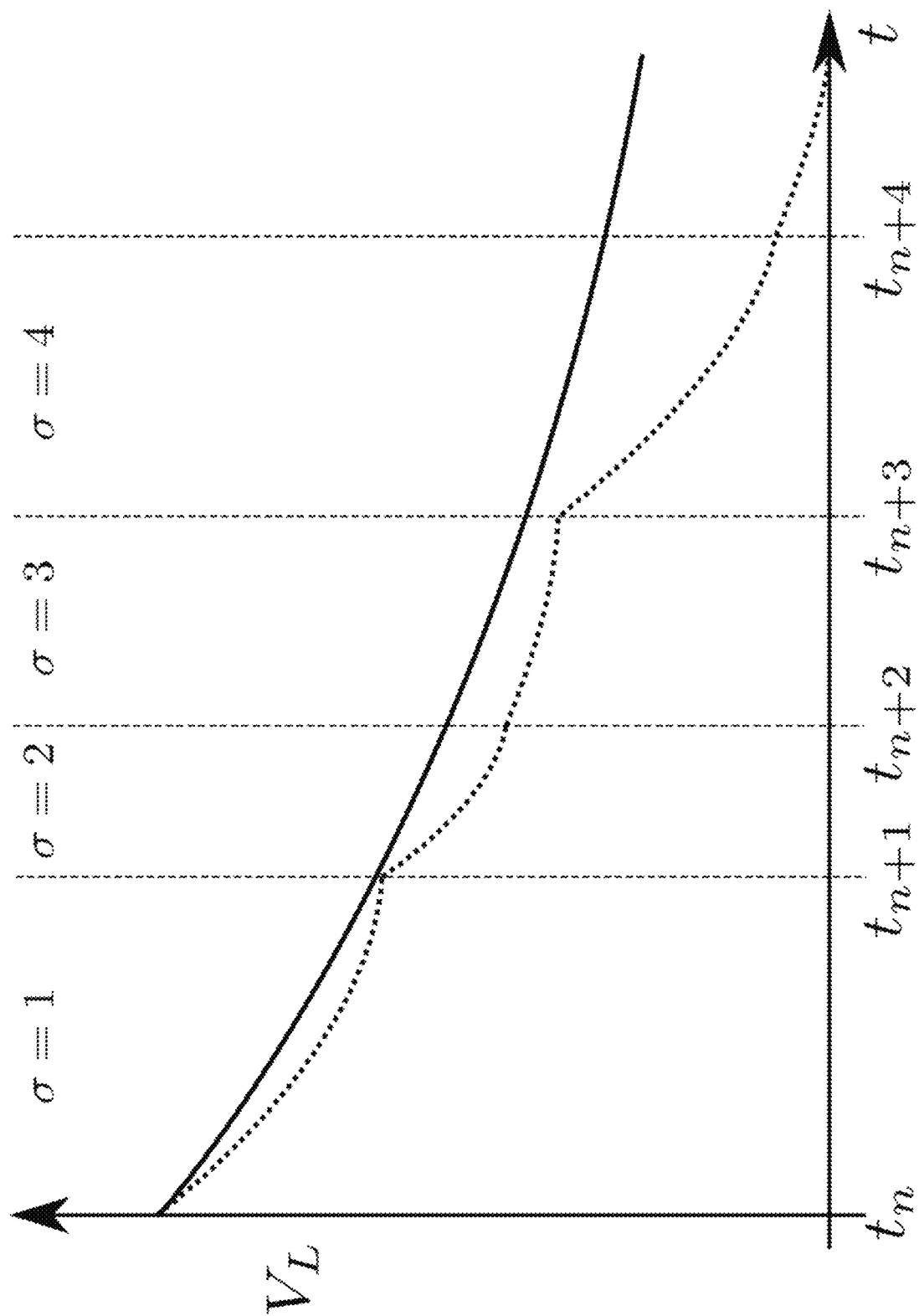
FIG. 21 shows, according to some embodiments, an exemplary plot of the behavior of a continuously differentiable, positive definite, common Lyapunov function $V_L$.

Remark 1. The exponential decay rate $\lambda_s$ represented the most conservative (i.e., smallest) decay rate for the closed-loop, switched error system. In practice, each subsystem had its own decay rate dependent on the lower bound of the corresponding $B_\sigma$, but in the preceding stability analysis, $c_{B1}$ was used as the lower bound on $B_\sigma$ for all $\sigma \in \mathcal{P}$. FIG. 21 illustrates how $V_L$ may behave in practice versus the conservative bound given in Equation 280.

V. Experiments

Experiments were conducted with the primary objective of evaluating the performance of the controller given in Equation 266 and distributed as FES and electric motor current according to Equations 252-256. Five able-bodied male subjects 21-31 years old participated in the experiments. Each subject gave written informed consent approved by the University of Florida Institutional Review Board. During the subsequent experiments, the subjects were instructed to relax and make no volitional effort to either assist or inhibit the FES or the electric motor input (i.e., passive riders).

A commercially available, stationary, motorized cycle (Exerpeutic Mini ACTIVCycle) with a 60 W brushed DC motor was modified for the purposes of the FES-cycling experiments. Cleats were added to a pair of orthotic boots (Aircast SP), which allowed them to be affixed to clipless pedals (MSW RP-200). These orthotic pedals served to fix the rider's feet to the pedals, prevent dorsiflexion and plantarflexion of the ankles, and maintain sagittal alignment of the lower legs. A 10-bit analog absolute encoder (US Digital MA3) was coupled to the cycle crank via 3D-printed spur gears to measure the crank position. A frame was constructed to ensure that the cycle did not move relative to the cycling seat (stationary desk chair). Current control of the cycle's motor was enabled by a general purpose linear amplifier (AE Techron LVC 5050) interfacing with the data acquisition hardware (Quanser Q8-USB), which also measured the encoder signal. The controller was implemented on a personal computer running real-time control software (QUARC, MATLAB/Simulink, Windows 7) at a sampling rate of 500 Hz.

A current-controlled stimulator (RehaStim, Hasomed, GmbH, Germany) delivered biphasic, symmetric, rectangular pulses to the subject's muscle groups via bipolar, self-adhesive, PALS® electrodes. The stimulation amplitudes were fixed at 90 mA for the quadriceps and 80 mA for the hamstrings muscle groups, and the stimulation pulse width for each muscle group was determined by $u_m$ and commanded to the stimulator by the control software. Stimulation frequency was fixed at 60 Hz. For safety, an emergency stop switch was attached to the cycling seat that enabled the subject to stop the experiment immediately if necessary, though no subjects found it necessary.

Electrodes were placed over the subjects' quadriceps femoris and hamstrings muscle groups according to Axelgaard's electrode placement manual. In these experiments, only the quadriceps and hamstrings muscle groups were stimulated to better demonstrate the balance between the FES and motor inputs. Each subject's legs were measured to obtain the distance from the greater trochanter to the lateral femoral condyle and from the lateral femoral condyle to the sole of the foot while the ankle was held in the anatomically neutral position. Subjects were then seated on the stationary cycle, and their feet were inserted securely into the orthotic pedals. The cycle seat position was adjusted for each subject's comfort while ensuring that full extension of the knees could not be achieved while cycling, and the distance from the cycle crank to the subject's left greater trochanter was measured. These measurements were used to calculate the torque transfer ratios for the subjects' muscle groups and to thereby determine the stimulation pattern.

The desired crank velocity $\dot{q}_d$ and position $q_d$ were designed as:

$$\dot{q}_d \triangleq \frac{5\pi}{3}\left\{1 - \exp\left[-\frac{2}{5}(t-t_0)\right]\right\} \quad (281)$$

$$q_d \triangleq \frac{5\pi}{3}(t-t_0) - \frac{5}{2}\dot{q}_d + q(t_0) \quad (282)$$

where $t_0 = 0$ seconds. Each trial lasted 180 seconds. The trajectories in Equations 281 and 282 ensured that the desired cadence started at 0 rpm and smoothly approached 50 rpm. The signals $\in_m$ were designed for $m \in \mathcal{M}$ as:

$$\in_m \triangleq \max(T_m)\gamma \quad (283)$$

where $\gamma \in \mathbb{R}$ was a scaling factor designed as:

$$\gamma \triangleq \begin{cases} 1 & t < 16 \\ 1.4 - \dfrac{t}{40} & 16 \leq t < 26 \\ 0.75 & t \geq 26 \end{cases} \quad (284)$$

The definitions in Equations 283-284 determined the stimulation pattern and FES-to-motor switching according to Equations 252-256, so that only the motor was active during the first 16 seconds of each trial (i.e., while the desired trajectory rose to 50 rpm). Then the stimulation of the muscle groups was added and the stimulation regions increased in size for 10 seconds until they reached the desired steady state stimulation pattern. This method for defining the stimulation pattern was selected because large muscle forces were required to pedal at low speeds, so the motor was used to bring the system to the desired cadence before FES was added. A constant input of 60 mA was added to the motor current input to mitigate the effect of friction in the motor gearbox. The control gains, introduced in Equations 256 and 266, and the constant $\alpha$, introduced in Equation 261, were tuned to yield acceptable tracking performance for each subject in preliminary testing and ranged as follows: $\alpha \in [1,7]$, $k_m = 0.25$ $\forall m \in \mathcal{M}$, $k_e \in [1.7 \times 10^{-4}, 3.5 \times 10^{-4}]$, $k_1 \in [200, 440]$, $k_2 = 40$, $k_3 \in [0.04, 0.08]$, $k_4 \in [0.004, 0.008]$.

Figure 22:
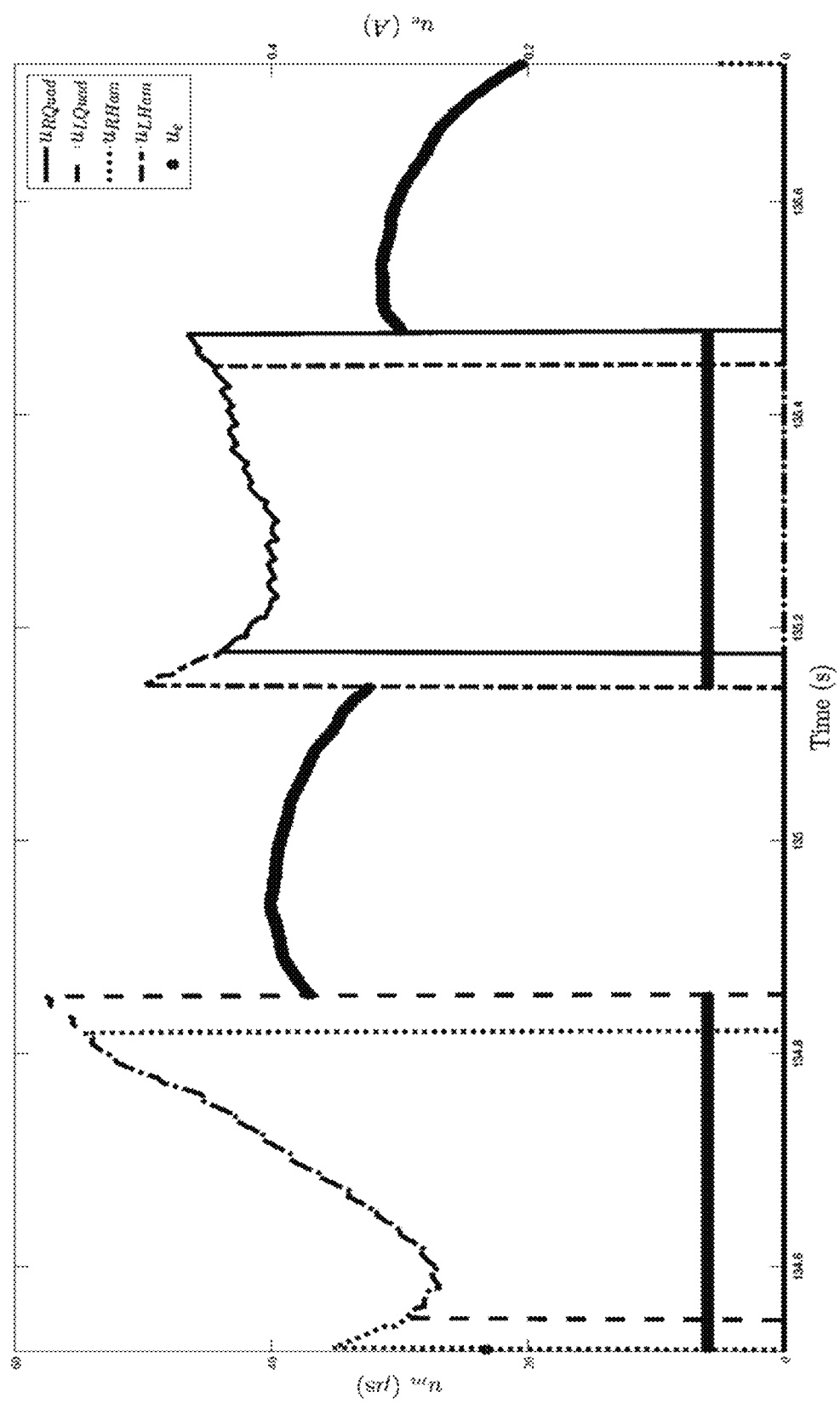
FIG. 22 shows, according to some embodiments, position tracking error, cadence tracking error, FES control input, and electric motor current input, for a subject in an experimental trial.
Figure 23:
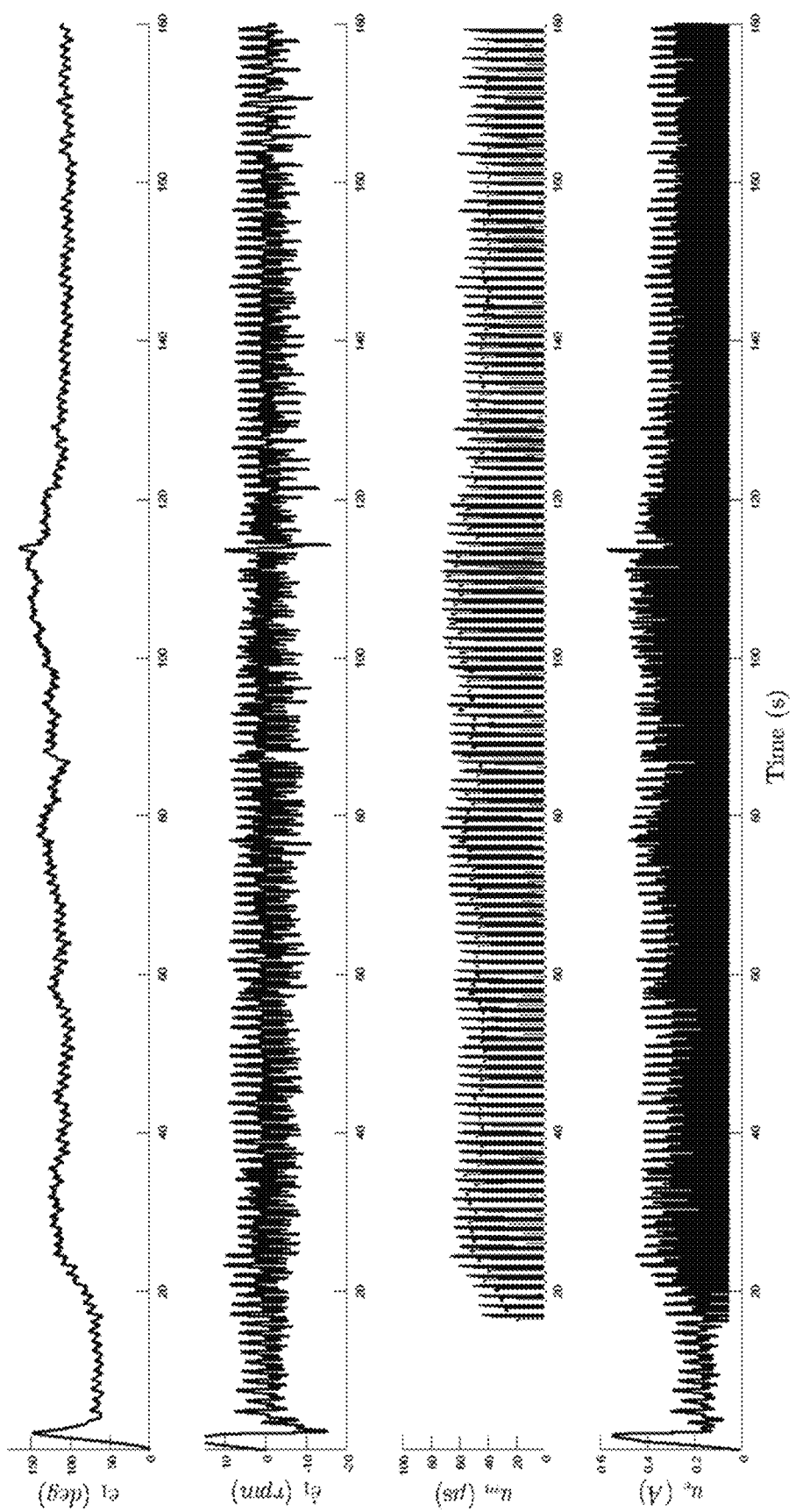
FIG. 23 shows, according to some embodiments, FES control inputs and motor current input from an experimental trial over a single crank cycle.

FIG. 22 depicts one subject's tracking performance, quantified by position tracking error $e_1$, cadence tracking error $\dot{e}_1$, the stimulation intensity input to each muscle group $u_m$, and the electic motor current input $u_e$. FIG. 23 provides an enhanced view of the distribution of the FES control inputs $u_m$ and the motor current input $u_e$ across one crank cycle in an experimental trial. Table VI summarizes the position and cadence tracking performance for each subject during the motor-only ($t \in [0,16)$ seconds), transitory ($t \in [16,26)$ seconds), and FES/motor ($t \in [26,180]$ seconds) periods of the trials.

TABLE VI

| | | Motor-only | | Transitory | | FES/Motor | |
|---|---|---|---|---|---|---|---|
| | | Mean | St. Dev. | Mean | St. Dev. | Mean | St. Dev. |
| Subject 1 | e1 (deg.) | 27.58 | 17.50 | 32.09 | 6.18 | 37.91 | 6.21 |
| | ė1 (rpm) | 0.34 | 7.81 | −0.01 | 4.36 | −0.01 | 4.74 |
| Subject 2 | e1 (deg.) | 29.99 | 8.10 | 25.90 | 4.52 | 38.45 | 7.85 |
| | ė1 (rpm) | 0.30 | 3.20 | 0.05 | 2.86 | 0.00 | 3.66 |
| Subject 3 | e1 (deg.) | 70.24 | 27.50 | 91.90 | 17.61 | 120.57 | 24.12 |
| | ė1 (rpm) | 0.67 | 6.04 | 0.77 | 3.65 | −0.03 | 4.83 |
| Subject 4 | e1 (deg.) | 69.61 | 22.45 | 90.06 | 16.67 | 116.33 | 13.25 |
| | ė1 (rpm) | 0.73 | 6.15 | 0.79 | 4.57 | −0.02 | 4.48 |
| Subject 5 | e1 (deg.) | 61.87 | 29.36 | 67.07 | 7.93 | 74.18 | 12.59 |
| | ė1 (rpm) | 0.58 | 7.07 | 0.41 | 5.43 | −0.04 | 6.12 |

The experimental results successfully demonstrated the ability of the controller in Equation 266, distributed between FES of the rider's muscle groups and electric motor current according to Equation 256, to achieve exponentially stable tracking performance despite parametric uncertainty (e.g., uncertain rider limb mass) and unknown disturbances. However, the results indicated exponential convergence to an ultimate bound on the tracking error, instead of convergence to zero, which could be due to unmodeled effects such as electromechanical delay between muscle activation and force production. The results for Subject 4, presented in FIG. 22, demonstrated typical performance during the motorized FES-cycling task, as corroborated by the data in Table VI. Of particular note were the mean and standard deviation of the cadence tracking error during the FES/motor period for all subjects, where the average cadence tracking error across all five subjects was −0.02±4.76 rpm (i.e., the actual cadence was centered about the desired cadence with less than 5 rpm in standard deviation). As indicated in the experimental data plotted in FIG. 23, the electric motor provided assistance as needed in the regions of the FES-cycling joint space where the rider's torque transfer ratios were small, and stability was maintained throughout the trial despite the discontinuous switching in the torque input to the system. The subjects reported that the cycling motion felt comfortable and natural and that they perceived their muscles as contributing significantly to the cycling task, though neither metabolic nor relative torque contribution (i.e., comparing FES torque input to muscle torque input) measurements were available to quantify these effects.

VI. Conclusion

A model for FES-cycling with electric motor assistance was presented that included the effects of a switched control input and unknown disturbances. Based on this model, a novel switching strategy was developed that applied FES to the rider's muscle groups in regions of the crank cycle where the rider's muscles contributed significantly to the cycling task and utilized an electric motor for assistance only as needed (i.e., in regions of poor kinematic efficiency). A switched sliding-mode controller was designed to yield global, exponentially stable tracking of a desired crank trajectory, provided sufficient gain conditions were satisfied. The control design was validated in experiments with five able-bodied subjects, where an average cadence tracking error of −0.02±4.76 rpm (−0.00±9.52% error) was demonstrated. The FES-cycling systems described in this Example have the potential to enhance therapeutic outcomes in a rehabilitative setting and to improve the performance of assistive cycling devices.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention.

For example, embodiments are described in which stimulation is applied to individuals with healthy legs. Portions of the limbs of a human to which muscle stimulation is applied may be prosthetic.

As another example, various controllers and control algorithms were described. These controllers and control algorithms may be used together or separately, in any suitable combination. Those controllers and algorithms may be implemented in any suitable way, including as programs, stored in a computer readable medium, executed by a microcontroller or other suitable processing circuitry (such as an ASIC, FPGA or the like). When used together, these controllers may be implemented separately, with one serving to provide inputs to, or process outputs from, the other. Alternatively, they may be combined mathematically or logically, such that control equations, representing the combined controllers and algorithms, are derived before programming or implementation in control circuitry. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An exercise device, comprising:
   a crank, configured for rotation by at least one limb of a human;
   at least one sensor adapted to measure position and velocity of the crank;
   a controller, coupled to the at least one sensor, wherein the controller is programmed to generate functional electrical stimulation to a person using the exercise device, by:
   for each of at least one limb of the person using the exercise device, determining a torque transfer ratio between a portion of the limb and the crank based on position and velocity of the crank measured by the at least one sensor;
   for each of the at least one limb, dynamically generating a control signal to control delivery of electrical stimulation to the at least one limb based on the determined torque transfer ratio being above a predetermined threshold.

2. The exercise device of claim 1, wherein the at least one limb comprises a first leg and a second leg, and the controller is configured such that:
   for each of the at least one limb, dynamically generating a control signal to control delivery of electrical stimulation comprises generating a control signal to:
   deliver a first amount of electrical stimulation to at least one electrode configured for coupling to at least a portion of a first set of quadriceps femoris muscles on the first leg, such that the first amount of electrical stimulation is delivered based on the determined torque transfer ratio between a knee of the first leg and the crank being negative; and
   deliver a second amount of electrical stimulation to at least one electrode configured for coupling to at least a portion of a second set of quadriceps femoris muscles on the second leg, such that the second amount of electrical stimulation is delivered based on the determined torque transfer ratio between a knee of the second leg and the crank being negative.

3. The exercise device of claim 1, further comprising an electric motor connected to the crank.

4. The exercise device of claim 1, wherein:
   the controller is further programmed to access at least one geometric parameter of the at least one limb, and
   the determining the torque transfer ratio comprises computing the torque transfer ratio based on the at least one geometric parameter of the at least one limb.

5. A method of providing functional electrical stimulation to a person, comprising:
   delivering a first amount of electrical stimulation to at least a portion of a first set of muscles on a first leg of the person, wherein the first amount of electrical stimulation is delivered based on a first torque transfer ratio between a joint of the first leg and a crank of a cycling device being negative, wherein a stimulation intensity of the first amount of electrical stimulation varies with a crank angle of the cycling device; and
   delivering a second amount of electrical stimulation to at least a portion of a second set of muscles on a second leg of a person, wherein the second amount of electrical stimulation is delivered based on a second torque transfer ratio between a joint of the second leg and the crank being negative, wherein a stimulation intensity of the second amount of electrical stimulation varies with the crank angle; and wherein the electrical stimulation causes the person to pedal the cycling device.

6. The method of claim 5, further comprising calculating the first amount of electrical stimulation and/or second amount of electrical stimulation using a control method.

7. The method of claim 6 wherein the control method is a switched sliding mode control method.

8. The method of claim 6, wherein the control method is exponentially stable.

9. The method of claim 5, wherein:
the first amount of electrical stimulation is delivered during a first part of a trajectory of the crank;
the second amount of electrical stimulation is delivered during a second part of the trajectory of the crank; and
the first and second parts of the crank trajectory do not overlap.

10. The method of claim 9, further comprising providing an amount of power to the crank from a motor during a third part of a crank trajectory, wherein the first, second, and third parts of the crank trajectory do not overlap.

11. The method of claim 5, further comprising calculating the first amount of electrical stimulation and/or second amount of electrical stimulation using a control method that compensates for electromechanical delay.

12. The method of claim 11, wherein the control method comprises an adaptive feedforward method.

13. The method of claim 12, wherein the adaptive feedforward method comprises a neural network-based method.

14. The method of claim 5, wherein the electrical stimulation causes the person to pedal the cycling device substantially continuously for at least 10 minutes.

15. The method of claim 5, further comprising:
determining a third torque transfer ratio for gluteal muscles on the first leg;
determining a fourth torque transfer ratio for gluteal muscles on the second leg;
delivering a third amount of electrical stimulation to at least a portion of a first set of gluteal muscles on the first leg of the person, wherein the third amount of electrical stimulation is delivered only when the third torque transfer ratio is positive; and
delivering a fourth amount of electrical stimulation to at least a portion of a second set of gluteal muscles on the second leg of the person, wherein the fourth amount of electrical stimulation is delivered only when the fourth torque transfer ratio is positive.

16. The method of claim 5, further comprising:
determining a fifth torque transfer ratio for hamstring muscles on the first leg;
determining a sixth torque transfer ratio for hamstring muscles on the second leg;
delivering a fifth amount of electrical stimulation to at least a portion of a first set of hamstring muscles on the first leg of the person, wherein the fifth amount of electrical stimulation is delivered only when the fifth torque transfer ratio is positive; and
delivering a sixth amount of electrical stimulation to at least a portion of a first set of hamstring muscles on the second leg of the person, wherein the sixth amount of electrical stimulation is delivered only when the sixth torque transfer ratio is positive.

17. The method of claim 5, further comprising:
measuring a crank velocity with a sensor;
comparing the measured crank velocity with a desired cadence to derive a mean cadence tracking error, wherein the mean cadence tracking error is in the range of about 0 rpm to about 1 rpm.

18. The method of claim 5, further comprising:
measuring a crank velocity with a sensor;
comparing the measured crank velocity with a desired cadence to derive a mean cadence tracking error, wherein the mean cadence tracking error is in the range of about 0 rpm to about 0.1 rpm.

19. The method of claim 5, wherein:
the first set of muscles on the first leg of the person are quadriceps femoris muscles on the first leg of the person;
the second set of muscles on the second leg of the person are quadriceps femoris muscles on the second leg of the person; and
the joint of the first leg is a knee of the first leg; and
the joint of the second leg is a knee of the second leg.

20. The method of claim 5, wherein:
the first set of muscles on the first leg of the person are gluteal muscles on the first leg of the person;
the second set of muscles on the second leg of the person are gluteal muscles on the second leg of the person; and
the joint of the first leg is a hip of the first leg; and
the joint of the second leg is a hip of the second leg.

21. The method of claim 5, wherein:
the first set of muscles on the first leg of the person are hamstring muscles on the first leg of the person;
the second set of muscles on the second leg of the person are hamstring muscles on the second leg of the person; and
the joint of the first leg is a knee of the first leg; and
the joint of the second leg is a knee of the second leg.

* * * * *